(12) United States Patent
Matsushima et al.

(10) Patent No.: US 8,377,938 B2
(45) Date of Patent: *Feb. 19, 2013

(54) PHENOXYPYRIDINE DERIVATIVE SALTS AND CRYSTALS THEREOF, AND PROCESS FOR PREPARING THE SAME

(75) Inventors: Tomohiro Matsushima, Tsukuba (JP); Shuji Shirotori, Tsukuba (JP); Keiko Takahashi, Tsukuba (JP); Atsushi Kamada, Tsukuba (JP); Kazunori Wakasugi, Tsukuba (JP); Takahisa Sakaguchi, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 6 days.

This patent is subject to a terminal disclaimer.

(21) Appl. No.: 12/031,568

(22) Filed: Feb. 14, 2008

(65) Prior Publication Data

US 2008/0318924 A1 Dec. 25, 2008

Related U.S. Application Data

(60) Provisional application No. 60/890,769, filed on Feb. 20, 2007.

(30) Foreign Application Priority Data

Feb. 16, 2007 (JP) ................. P2007-036690

(51) Int. Cl.
*A61K 31/496* (2006.01)
*A61K 31/4427* (2006.01)
*C07D 401/12* (2006.01)

(52) U.S. Cl. ............ 514/253.13; 514/340; 544/364; 546/268.1

(58) Field of Classification Search .......... None
See application file for complete search history.

(56) References Cited

U.S. PATENT DOCUMENTS

| | | |
|---|---|---|
| 6,790,852 B2 | 9/2004 | Brandt et al. |
| 7,253,286 B2 | 8/2007 | Funahashi et al. |
| 7,425,564 B2 | 9/2008 | Fujiwara et al. |
| 7,531,532 B2 | 5/2009 | Matsushima et al. |
| 7,652,022 B2 | 1/2010 | Floersheimer et al. |
| 7,790,885 B2 | 9/2010 | Nagai et al. |
| 7,855,290 B2 | 12/2010 | Matsushima et al. |
| 8,288,538 B2 | 10/2012 | Matsushima et al. |
| 2003/0199691 A1 | 10/2003 | Brandt et al. |
| 2004/0053908 A1 | 3/2004 | Funahashi et al. |
| 2004/0214874 A1 | 10/2004 | Brandt et al. |
| 2004/0242603 A1 | 12/2004 | Fujiwara et al. |
| 2005/0009840 A1 | 1/2005 | Cui et al. |
| 2005/0009842 A1 | 1/2005 | Zemlicka et al. |
| 2005/0014753 A1 | 1/2005 | Ding et al. |
| 2005/0245530 A1 | 11/2005 | Borzilleri et al. |
| 2005/0277652 A1 | 12/2005 | Matsushima et al. |
| 2006/0252777 A1* | 11/2006 | Kim et al. ............ 514/264.1 |
| 2007/0023768 A1 | 2/2007 | Konno et al. |
| 2007/0153894 A1 | 7/2007 | Nagai et al. |

(Continued)

FOREIGN PATENT DOCUMENTS

| EP | 1 411 046 A1 | 4/2004 |
|---|---|---|
| EP | 1 415 987 A1 | 5/2004 |

(Continued)

OTHER PUBLICATIONS

Berge et al. J. of Pharmaceutical Sciences, vol. 66 p. 1-19 (1977).*
Naran et al. Expert Opin.Ther. Targets p. 569-581 (2009).*
Cancer Drug Design and Discovery, Neidle, Stephen,ed. (Elsevier/Academic Press), pp. 427-431 (2008).*
Nakagawa et al.Cancer Sci. vol. 101, p. 210-215 (2010).*
"E7050: A novel orally active c-Met and VEGFR-2 tyrosine kinase inhibitor exhibited potent antitumor effect and prolongation of survival in preclinical mice model.", Nakagawa et al., Proceedings of the American Association for Cancer Research, vol. 49, p. 1154, #4845, 2008.
"E7050: A novel small molecule inhibitor the c-Met and VEGFR-2 tyrosine kinases.", Obaishi et al., Proceedings of the American Association for Cancer Research, vol. 49, p. 1154, #4846, 2008.

(Continued)

*Primary Examiner* — Emily Bernhardt
(74) *Attorney, Agent, or Firm* — Birch, Stewart, Kolasch & Birch, LLP

(57) ABSTRACT

The invention provides acid addition salts of the compounds represented by formula (1) or (2), or crystals thereof, and processes for preparing the same. The salts or crystals have HGFR inhibitory activity and excellent physical properties (solubility, safety, etc.) and are therefore useful as anti-tumor agents, angiogenesis inhibitors and inhibitors for metastasis for a various types of tumor.

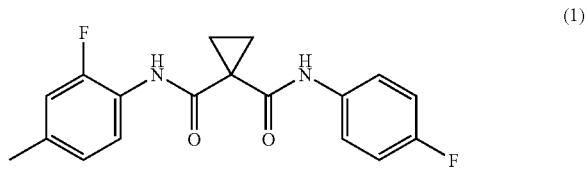

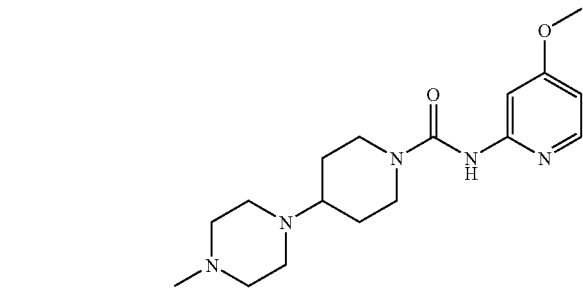

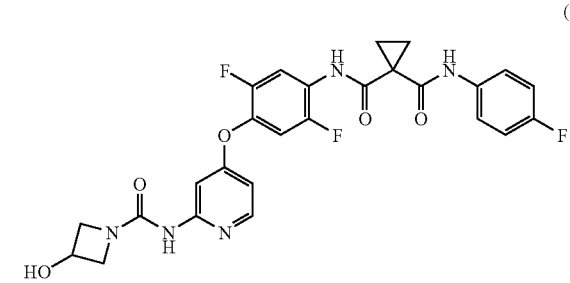

21 Claims, 14 Drawing Sheets

U.S. PATENT DOCUMENTS

| | | | |
|---|---|---|---|
| 2008/0102870 | A1 | 5/2008 | Gothard et al. |
| 2008/0214815 | A1 | 9/2008 | Nagai et al. |
| 2008/0300273 | A1 | 12/2008 | Christensen et al. |
| 2008/0318924 | A1 | 12/2008 | Matsushima et al. |
| 2008/0319188 | A1 | 12/2008 | Matsushima et al. |
| 2009/0176797 | A1 | 7/2009 | Obaishi et al. |
| 2009/0227556 | A1 | 9/2009 | Obaishi |
| 2010/0075944 | A1 | 3/2010 | Matsushima et al. |
| 2010/0311972 | A1 | 12/2010 | Nagai |

FOREIGN PATENT DOCUMENTS

| | | |
|---|---|---|
| EP | 1 473 043 A1 | 11/2004 |
| EP | 1 506 962 A2 | 2/2005 |
| EP | 1 719 762 A1 | 11/2006 |
| EP | 1 719 763 A1 | 11/2006 |
| EP | 1 889 836 A1 | 2/2008 |
| EP | 2058302 A1 | 5/2009 |
| EP | 2 119 706 A1 | 11/2009 |
| JP | 2007-153894 | 6/2007 |
| WO | WO-02/32872 A1 | 4/2002 |
| WO | WO-02/096361 A2 | 12/2002 |
| WO | WO-03/000660 A1 | 1/2003 |
| WO | WO-03/087026 A1 | 10/2003 |
| WO | WO-03/099771 A2 | 12/2003 |
| WO | WO 2004/030524 A2 | 4/2004 |
| WO | WO-2004/076412 A2 | 9/2004 |
| WO | WO-2004/089286 A2 | 10/2004 |
| WO | WO-2005/004607 A1 | 1/2005 |
| WO | WO-2005-004808 A2 | 1/2005 |
| WO | WO-2005/005378 A2 | 1/2005 |
| WO | WO-2005/005389 A2 | 1/2005 |
| WO | WO-2005/010005 A1 | 2/2005 |
| WO | WO-2005/016920 A1 | 2/2005 |
| WO | WO-2005/030140 A2 | 4/2005 |
| WO | WO-2005/040154 A1 | 5/2005 |
| WO | WO-2005/082854 A1 | 9/2005 |
| WO | WO-2005/082855 A1 | 9/2005 |
| WO | WO 2005/115478 A2 | 12/2005 |
| WO | WO-2005/117867 A2 | 12/2005 |
| WO | WO-2006/004636 A1 | 1/2006 |
| WO | WO-2006/004636 A2 | 1/2006 |
| WO | WO-2006/014325 A2 | 2/2006 |
| WO | WO-2007/023768 A1 | 3/2007 |
| WO | WO-2008/102870 A1 | 8/2008 |

OTHER PUBLICATIONS

Obaishi et al., "E7050: a novel smal moledule inhibitor of the c-Met and and VEGFR-2 tyrosine kinases," Proceedings of the American Asociation for Cancer Research, vol. 9, pp. 1154, #4846, 2008.

Vippagunta et al., "Crystalline Solids," Advanced Drug Delivery Reviews, vol. 48, 2001, pp. 3-26.

Ulrich, "Crystallization-4," Crystal Characteristics, Kirk-Othmer Encyclopedia of Chemical Technology, 2002, pp. 1-7.

West, "Solid Solutions, Solid State Chemistry and its applicationss," 1988, p. 358 & 365.

Rosen et al., "Scatter Factor and Angiogenesis," Advances in Cancer Research, 1995, pp. 257-279.

Maehara et al., "NK4, a four-kringle antagonist of HGF, inhibits spreading and invasion of human pancreatic cancer cells," British Journal of Cancer, 2001, vol. 84, No. 6, pp. 864-873.

Matsumoto et al., "NK4 (HGF-antagonist/angiogenesis inhibitor) in cancer biology and therapeutics," Cancer Sci, Apr. 2003, vol. 94, No. 4, pp. 321-327.

"MET tyrosine kinase inhibitors," Nature Reviews, Drug Discovery, Nature Publishing Group, vol. 7, Jun. 2008, p. 469.

Miller et al., "Genomic amplification of MET with boundaries within fragile site FRA7G and upregulation of MET pathways in esophageal adenocarcinoma," Oncogene, 2006, vol. 25, pp. 409-418.

To et al., "The roles of hepatocyte growth factor/scatter factor and Met receptor in human cancers (Review)," Oncology Reports 5: pp. 1013-1024, 1998.

Nakagawa et al., "E7050: A novel orally active c-Met and VEGFR-2 tyrosine kinase inhibitor exhibited potent antitumor effect and prolongation of survival in preclinical mice model," Proceedings of the American Assocation for Cancer Research, vol. 49, 2008, #4845, p. 1154.

"E7050: a novel small molecule inhibitor of the c-Met and VEGFR-2 tyrosine kinases," Obaishi et al., Abstract of P1-7 in Japanese Association for Molecular Target Therapy of Cancer, 2008; "E7050: a novel orally active c-Met and VEGFR-2tyrosine kinase inhibitor exhibited potent antitumor effect and prolongation of survival in preclinical mice model," Nakagawa et al., Abstract of P1-8 in Japanese Association for Molecular Target Therapy of Cancer 2008.

Kolibaba et al., "Protein tyrosine kinases and cancer", B. B. A., 1333, F217-F248, (Jul. 1997), Portland, OR.

Scheijen et al., "Tyrosine kinase oncogenes in normal hematopoiesis and hematological disease", Oncogene, 21, 3314-3333, (2002), Boston, MA.

Blume-Jensen et al., "Activation of the human c-kit product by ligand-induced dimerization mediates circular actin reorganization and chemotaxis", The EMBO Journal, 10, 4121-4128, (1991), Thousand Oaks, CA and Sweden.

Lev et al., "A specific combination of substrates is involved in signal transduction by the kit-encoded receptor" The EMBO Journal, 10, 647-654, (1991), Isreal.

Wang et al., "The Expression of the Proto-Oncogene C-Kit in the Blast Cells of Acute Myeloblastic Leukemia", Leukemia, 3, 699-702, (1989), Toronto, Canada and Cambridge, MA.

Kanakura et al., "Expression, Function and Activation of the Protooncogen c-kit Product in Human Leukemia Cells", Leukemia and Lymphoma, 10, 35-41, (1993), Osaka, Japan.

Ikeda et al., "Expression and Functional Role of the Proto-oncogene c-kit in Acute Myeloblastic Leukemia Cells", Blood, 78, 2962-2968, (1991).

Ikeda et al., "Changes in phenotype and proliferative potential of human acute myeloblastic leukemia cells in culture with stem cell factor", Experimental Hematology, 21, 1686-1694, (Aug. 1993), Osaka, Japan.

Furitsu et al., "Identification of Mutations in the Coding Sequence of the Proto-oncogene c-kit in a Human Mast Cell Leukemia Cell Line Causing Ligand-independent Activation of c-kit Product", J. Clin. Invest., 92, 1736-1744, (1993), Osaka, Japan; Rochester, MN and Adelaide, South Australia.

Hibi et al., "Coexpression of the stem cell factor and the c-kit genes in small-cell lung cancer", Oncogene, 6, 2291-2296, (1991), Nagoya, Japan.

Sekido et al., "Preferential Expression of c-kit Protooncogene Transcripts in Small Cell Lung Cancer", Cancer Research, 51, 2416-2419, (May 1, 1991), Nagoya, Japan.

Lasota et al., "Mutations in Exons 9 and 13 of KIT Gene Are Rare Events in Gastrointestinal Stromal Tumors", American Journal of Pathology, 157, 1091-1095, (Oct. 2000), Washington, D.C.; Helsinki, Finland and Krakow, Poland.

Taniguchi et al., Éffect of c-kit Mutation on Prognosis of Gastrointestinal Stromal Tumors, Cancer Research, 59, 4297-4300, (Sep. 1, 1999), Japan.

Strohmeyer et al., "Expression of the hst-1 and c-kit Protooncogenes in Human Testicular Germ Cell Tumors", Cancer Research, 51, 1811-1816, (Apr. 1, 1991), CA and Germany.

Tian et al., "Activating c-kit Gene Mutations in Human Germ Cell Tumors", American Journal of Pathology, 154, 1643-1647, (Jun. 1999), VA.

Tonary et al., "Lack of Expression of c-Kit in Ovarian Cancers is Associated With Poor Prognosis", Int. J. Cancer (Pred. Oncol.), 89, 242-250, (2000), Ottawa, Canada.

Natali et al., "Breat Cancer is Associated With Loss of the c-kit Ikit Oncogene Product". Int. J. Cancer, 52, 713-717, (1992), Rome, Italy.

Hines et al., "Coexpression of the c-kit and Stem Cell Factor Genes in Breast Carcinomas", Cell Growth & Differentiation, 6, 769-779, (Jun. 1995), Richmond, VA.

Berdel et al., "Recombinant Human Stem Cell Factor Stimulates Growth of a Human Glioblastoma Cell Line Expressing c-kit Protooncogene", Cancer Research, 52, 3498-3502, (Jun. 15, 1992), Germany.

Cohen et al., "Expression of Stem Cell Factor and c-kit in Human Neuroblastoma", Blood, 84, 3465-3472, (1994).

Bellone et al., "Growth Stimulation of Colorectal Carcinoma Cells Via the c-Kit Receptor Is Inhibited by TGF-β1", Journal of Cellular Physiology, 172, 1-11, (1997), Torino, Italy and Philadelphia, PA.

Hamel et al., "The road less travelled: c-kit and stem cell factor", Journal of Neuro-Oncology, 35, 327-333, (1997), Hamburg, Germany and San Francisco, CA.

Kitamura et al., "Regulation of Development, Survival and Neoplastic Growth of Mast Cells through the c-kit Receptor", Int. Arch. Allergy Immunol., 107, 54-56, (1995), Osaka, Japan.

Metcalfe, "Classification and Diagnosis of Mastocytosis: Current Status", J. Invest. Derm., 96, 2S-4S, (1991), Bethesda, MD.

Golkar et al., "Mastocytosis", The Lancet, 349, 1379-1385, (1997).

Nagata et al., "Elevated expression of the proto-oncogene c-kit in patients with mastocytosis", Leukemia, 12, 175-181, (1998), Bethesda, MD.

Longley et al., "Altered Metabolims of Mast-Cell Growth Factor (c-kit Ligand) in Cutaneous Mastocytosis", New England Journal of Medicine, 328, 1302-1307, (May 6, 1993).

Longley et al., "Somatic c-Kit activating mutation in urticaria pigmentosa and aggressive mastocytosis: establishment of clonality in a human mast cell neoplasm", Nature Genetics, 12, 312-314, (Mar. 1996).

Thomas et al., "The Eosinophil and its Role in Asthma", Gen. Pharmac., 27, 593-597, (1996), Southampton, UK.

Metcalfe et al., "Mast Cells", Physiological Reviews, 77, 1033-1079, (Oct. 1997), Tel Aviv, Israel.

Naclerio et al., "Rhinitis and Inhalant Allergens", JAMA, 278, 1842-1848, (Dec. 10, 1997).

Meltzer, "The pharmacological basis for the treatment of perennial allergic rhinitis and non-allergic rhinitis with topical corticosteroids", Allergy, 52, 33-40, (1997), San Diego, CA.

Okayama et al., "Activation of Eosinophils with Cytokines Produced by Lung Mast Cells", International Archives of Allergy and Immunology, 114, 75-77, (1997), Maebashi, Japan; Southampton, UK and Adelaide, Australia.

Okayama et al., "Human lung mast cells are enriched in the capacity to produce granulocyte-macrophage colony-stimulating factor in response to IgE-dependent stimulation", Eur. J. Immunol., 28, 708-715, (1998), Maebashi, Japan, Adelaide, Australia and Southampton, GB.

Metcalf, "Lineage commitment in the progeny of murine hematopoietic preprogenitor cells: Influence of thrombopoietin and interleukin", Proc. Natl. Acad. Sci., 95, 6408-6412, (May 1998), Victoria, Australia.

Kay et al., "Eosinophils and Eosinophil-Associated Cytokines in Allergic Inflammation", International Archives of Allergy and Immunology, 113, 196-199, (1997), London, UK.

Hogaboam et al., "Novel Role of Transmembrane SCF for Mast Cell Activation and Eotaxin Production in Mast Cell-Fibroblast Interactions", The Journal of Immunology, 160, 6166-6171, Feb. 17, 1998), Ann Arbor, MI and Frederick, MD.

Luckas et al., "Stem Cell Factor (c-kit Ligand) Influences Eosinophil Recruitment and Histamine Levels in Allergic Airway Inflammation", The Journal of Immunology, 156, 3945-3951, (Feb. 28, 1996), Ann Arbor, MI; Frederick, MD and New Haven, CT.

Folkman et al., "Angiogenesis", The Journal of Biological Chemistry, 267, 10931-10934, (1992), Boston, MA.

Folkman, "Clinical Applications of Research on Angiogenesis", The New England Journal of Medicine, 333, 1757-1763, (Dec. 28, 1995).

Folkman, "What Is the Evidence That Tumors Are Angiogenesis Dependent?", Journal of the National Cancer Institute, 82, 4-6, (Jan. 3, 1990), Boston, MA.

Ferrara et al., "Molecular and Biological Properties of the Vascular Endothelial Growth Factor Family of Proteins", Endocrine Reviews, 13, 18-32, (1992), San Francisco, CA.

Plate et al., "Vascular endothelial growth factor is a potential tumour angiogenesis factor in human gliomas in vivo", Letter to Nature, 359, 845-848, (1992), Germany.

Plate et al., "Up-Regulation of Vascular Endothelial Growth Factor and Its Cognate Receptors in a Rat Glioma Model of Tumor Angiogenesis", Cancer Research, 53, 5822-5827, (Dec. 1, 1993), Germany.

Berkman et al., "Expression of the Vascular Permeability Factor/Vascular Endothelial Growth Factor Gene in Central Nervous System Neoplasms", The Journal of Clinical Investigation, 91, 153-159, (Jan. 1993), Bethesda, MD and Memphis, TN.

Nakamura et al., "Vascular Endothelial Growth Factor Is a Potent Angiogenic Factor in AIDS-Associated Kaposi's Sarcoma-Derived Spindle Cells", The Journal of Immnology, 158, 4992-5001, (Feb. 12, 1997), Germany and CA.

Mustonen et al., "Endothelial Receptor Tyrosine Kinases Involved in Angiogenesis", The Journal of Cell Biology, 129, 895-898, (May 1995), Helsinki, Finland.

Bardella et al., "Truncated RON Tyrosine Kinase Drives Tumor Cell Progression and Abrogates Cell-Cell Adhesion Through E-Cadherin Transcriptional Repression", Cancer Research, 64, 5154-5161, (Aug. 1, 2004), Italy.

O'Toole et al., "Therapeutic Implications of a Human Neutralizing Antibody to the Macrophage-Stimulating Protein Receptor Tyrosine Kinase (RON), a c-MET Family Member", Cancer Research, 66, 9162-9170, (2006), Stonybrook, NY and Cincinnati, OH.

Carlomagno et al., "ZD6474, an Orally Available Inhibitor of KDR Tyrosine Kinase Activity, Efficiently Blocks Oncogenic RET Kinases", Cancer Research, 62, 7284-7290, (Dec. 15, 2002), Italy and UK.

Carlomagno et al., "BAY 43-9006 Inhibition of Oncogenic RET Mutants", Journal of National Cancer Institute, 98, 326-334, (Mar. 1, 2006).

Terman et al., "Identification of a new endothelial cell growth factor receptro tyrosine kinase", Oncogene, 6, 1677-1683, (1991), NY.

Park et al., "Homogeneous Proximity Tyrosine Kinase Assays: Scintillation Proximity Assay versus Homogeneous Time-Resolved Fluorescence", Analytical Biochemistry, 269, 94-104, (1999), Rahway, NJ.

Watson et al., "Inhibition of c-Met as a Therapeutic Strategy for Esophageal Adenocarcinoma," Neoplasia, vol. 8, No. 11, Nov. 2006, pp. 949-955.

English Translation of International Search Report and Written Opinion for PCT/IB2008/003880 issued Aug. 11, 2009.

Office Action dated Dec. 3, 2008 in related Russian patent application No. 2008110932, with English translation.

Office Action dated Nov. 5, 2007 in related patent application No. 184/2006/4959 in Bangladesh, in English.

Office Action (dated Oct. 21, 2008 and Dec. 12, 2007) in related patent application No. 1024/2006 in Pakistan, in English.

Office Action (dated Oct. 21, 2008) in related patent application No. 375/2008 in Pakistan, in English.

US Office Action dated May 29, 2009 issued in U.S. Appl. No. 11/508,322.

US Office Action dated Dec. 18, 2008 issued in U.S. Appl. No. 11/508,322.

Hiroki Kuniyasu et al.; Frequent amplification . . . , Biochemical and Biophysical Research Communications, vol. 189, No. 1, pp. 227-232, Nov. 30, 1992.

Chi Liu et al., Overexpression of *c-met* . . . , Oncogene, 7, pp. 181-185, 1992.

Rola A. D. Ghoussoub et al.; Expression of *c-met* . . . , Cancer, 82, pp. 1513-1520, 1998.

Louis L. Pisters et al., C-met Proto-Oncogene Expression, The Journal of Urology, vol. 154, pp. 293-298, Jul. 1995.

Iwao Takanami et al., Hepatocyte Growth Factor . . . , Oncology, 53, pp. 392-397, 1996.

Laura Schmidt et al., Novel mutations of the Met . . . , Oncogene, 14, pp. 2343-2350, 1999.

Shahriar Koochekpour et al., Met and Hepatocyte Growth . . . , Cancer Research, 57, pp. 5391-5398, 1997.

Janos Tanyi et al., Evaluation of the Tyrosine . . . , Pathology Oncology Research, 5, pp. 187-191, 1999.

Yoshitaka Imaizumi et al., Expression of the c-Met . . . , Clinical Cancer Research, vol. 9, pp. 181-187, 2003.

H. Saeki et al., "Concurrent overexpression of Ets-1 and c-Met correlates with a phenotype of high cellular motility in human esophageal cancer", International Journal of Cancer, vol. 98, No. 1, pp. 8-13, 2002.

Matthias Ebert et al., "Coexpression of the *c-met* Proto-oncogene and Hepatocyte Growth Factor in Human Pancreatic Cancer", Cancer Research 54, pp. 5775-5778, 1994.

Extended European Search Report, dated Nov. 16, 2010, for European Application No. 07805959.9.

International Preliminary Report on Patentability, dated Feb. 24, 2009, for Application No. PCT/JP2007/066185.
International Search Report, dated Mar. 10, 2009, for Application No. PCT/JP2009/052401.
US Office Action, dated Jan. 12, 2011, for U.S. Appl. No. 12/315,291.
US Office Action, dated Jun. 7, 2010, for U.S. Appl. No. 12/315,291.
Jakeman et al., "Developmental Expression of Binding Sites and Messenger Ribonucleic Acis for Vascular Endothelial Growth Factor Suggests a Role for This Protein in Vasculogenesis and Angiogenesis", Endocrinology, 133, 848-859, (1993), San Francisco, CA.
Mitsui, Yoji, et al., "Cell Culture Technique", Lectures on New Biochemical Experiments, 18, 197-202, with English language translation.
English translation of WO 2008/102870 published Aug. 28, 2008.
English translation of International Preliminary Report on Patentability (IPRP-Chapter 100 issued in International Application No. PCT/JP2007/066185 dated Mar. 5, 2009 (6 pages).
Carlomagno et al., "ZD6474, An Orally Available Inhibitor of KDR Tyrosine Kinase Activity, Efficiently Blocks Oncogenic RET Kiinases", Cancer Research, vol. 62, Dec. 15, 2002, pp. 7284-7290.
Matsushima et al., "Preparation of Pyridine and Pyrimidine Derivatives as Inhibitors of Hepatocyte Growth Factor Receptor (HGFR)".
Non-Final Office Action for U.S. Appl. No. 12/031,568, dated Feb. 5, 2010.
Notice of Allowance and Fees Due for U.S. Appl. No. 11/508,322, dated Sep. 15, 2009.
Notice of Allowance and Fees Due for U.S. Appl. No. 11/892,785, dated Apr. 5, 2010.
Pakistani Office Action for Application No. 1024-2006, dated Oct. 21, 2008 and Dec. 12, 2007.
Pakistani Office Action for Application No. 375-2008, dated Oct. 21, 2008.
Smolen, "Amplification of MET May Identify a Subset of Cancers With Extreme Sensitivity to the Selective Tyrosine Kinase Inhibitor PHA-665752", PNAS, vol. 103, No. 7, Feb. 14, 2006.
Translation for WO 2005/082854 (Sep. 2005).
International Preliminary Report on Patentability and Written Opinion of the International Searching Authority mailed Oct. 14, 2010 for International Application No. PCT/JP2009/052401 (Forms PCT/ISA/237, PCT/IB/338 and PCT/IB/373).
International Preliminary Report on Patentability and Written Opinion of the International Searching Authority mailed Jul. 14, 2011 for International Application No. PCT/JP2008/071881 (Forms PCT/ISA/237, PCT/IB/338 and PCT/IB/373).
European Search Report for Application No. 09713617.0, dated Apr. 28, 2011.
U.S. Office Action, dated Aug. 29, 2011, for U.S. Appl. No. 12/558,982.
Indonesian Office Action dated Jan. 13, 2012, for Application No. WO0200800601.
Israeli Notice of Deficiencies in Patent Application No. 197141 and an English translation thereof dated Feb. 22, 2012.
Notice of Allowability dated on Feb. 29, 2012 for PH Patent Application No. 1-2007-502319.
Response to Office Action filed Feb. 6, 2012 for PH Patent Application No. 1-2007-502319.
Advanced Automated Peptide Protein Technologies, The Spirit of Innovation, "Coupling Reagents." published Aug. 3, 2007, 4 pages, http://www.aapptec.com.
U.S. Notice of Allowance, dated Apr. 26, 2011, for U.S. Appl. No. 12/315,291.
U.S. Notice of Allowance, dated Jan. 2, 2009, for U.S. Appl. No. 11/065,631.
U.S. Notice of Allowance, dated Sep. 9, 2008, for U.S. Appl. No. 11/065,631.
U.S. Office Action (Advisory Action), dated Mar. 24, 2011, for U.S. Appl. No. 12/315,291.
U.S. Office Action, dated Apr. 5, 2011, for U.S. Appl. No. 12/558,982.
U.S. Office Action, dated Feb. 28, 2008, for U.S. Appl. No. 11/065,631.
U.S. Office Action, dated Oct. 26, 2011, for U.S. Appl. No. 12/867,646.
Varvoglis, "Chemical Transformations Induced by Hypervalent Iodine Reagents,"Tetrahedron, vol. 53, No. 4, 1997, pp. 1179-1255.
Australian Office Action dated Dec. 22, 2011, for Application No. 2007288793.
Chinese Notice of Allowance dated Jan. 11, 2012, for Application No. 200680021939.X.
European Notice of Allowance dated Feb. 6, 2012, for Application No. 05719973.9.
European Search Report dated Sep. 7, 2011, for Application No. 06796594.7.
Indonesian Office Action dated Jan. 13, 2012, for Application No. W00200800601.
Australian Notice of Acceptance, dated Mar. 16, 2012, for Australian Patent Application No. 2007289787.
Australian Office Action dated Dec. 22, 2011, for Australian Application No. 2007288793.
Australian Voluntary Amendment, dated Nov. 18, 2009, for Australian Patent Application No. 2008217931.
Canadian Voluntary Amendment, dated Aug. 20, 2009, for Canadian Patent Application No. 2679602.
Chinese Amendment, filed Aug. 7, 2009, for Chinese Patent Application No. 200880004511.3, with partial English translation.
Chinese Notice of Allowance for Chinese Application No. 200680021939.X, mailed Jan. 11, 2012, with English translation.
Chinese Office Action, dated Jul. 5, 2011, for Chinese Patent Application No. 200880004511.3, with English translation.
European Amendment, dated Apr. 19, 2012, for European Application No. 06796594.7.
European Amendment, filed Sep. 8, 2009, for European Patent Application No. 08711837.8.
European Notice of Allowance dated Feb. 6, 2012 for European Patent Application No. 05719973.9.
Extended European Search Report, dated Mar. 28, 2011, for European Patent Application No. 08711837.8.
Extended European Search Report, dated Sep. 7, 2011, for European Application No. 06796594.7.
Indian Response to First Examination Report, dated Jan. 16, 2012, for Indian Application No. 1424/CHENP/2008 dated Jan. 18, 2012.
Indian Voluntary Amendment (Complete Specification). dated Sep. 23, 2009, for Indian Patent Application No. 5625/CHENP/2009.
Indonesian Office Action for Indonesian Application No. W-00200800601, mailed Jan. 13, 2012, with English translation.
Israeli Amendment, filed Aug. 18, 2009, for Israel Patent Application No. 200466 (English version only provided).
Israeli Notice Prior to Examination, dated Jun. 22, 2010, for Israel Patent Application No. 200486, with English translation.
Israeli Office Action, dated Feb. 22, 2012, for Israeli Application No. 197141, with English translation.
Korean Amendment, dated Aug. 10, 2009, for Korean Patent Application No. 10-2009-7013723 with English translation.
Korean Notice of Final Rejection, dated Jul. 29, 2011, for Korean Patent Application No. 10-2009-7013723, with English translation.
Korean Office Action, dated May 19, 2011, for Korean Patent Application No. 10-2009-7013723, with English translation.
Supplementary European Search Report, dated Apr. 14, 2011, for European Application No. 08711837.8.
U.S. Notice of Allowance, dated Apr. 3, 2012, for U.S. Appl. No. 12/558,982.
Australian Amendment dated Jan. 25, 2008 for AU Application No. 2006282456.
Australian Amendment dated May 29, 2009 for AU Application No. 2007288793.
Australian Notice of Acceptance dated Aug. 17, 2009 for AU Application No. 2006282456.
Australian Office Action dated Jun. 12, 2009 for AU Application No. 2006282456.
Bangladeshi Amendment dated May 6, 2008 for BD Application No. 184/2006.
Bangladeshi Amendment dated Sep. 26, 2007 for BD Application No. 184/2006.

Bangladeshi Letter dated Feb. 2, 2012 for BD Application No. 184/2006.
Bangladeshi Office Action dated Nov. 5, 2007 for BD Application No. 184/2006.
Brazilian Amendment dated May 29, 2009 for BR Application No. PI0616799-3 (with partial English translation).
Canadian Amendment dated Oct. 23, 2007 for CA Application No. 2605854.
Canadian Notice of Allowance dated Apr. 7, 2010 for CA Application No. 2605854.
Canadian Office Action dated Jul. 29, 2009 for CA Application No. 2605854.
Chinese Amendment dated Dec. 18, 2007 for CN Application No. 200680021939.X (with English translation).
Chinese Office Action dated Mar. 30, 2011 for CN Application No. 200680021939.X (with English translation).
Chinese Office Action dated May 27, 2010 for CN Application No. 200680021939.X (with English translation).
Chinese Office Action dated Sep. 2, 2010 for CN Application No. 200680021939.X (with English translation).
European Amendment dated Jan. 11, 2008 for EP Application No. 06796594.7.
European Amendment dated Nov. 16, 2007 for EP Application No. 06796594.7.
European Decision to Grant dated Nov. 4, 2011 for EP Application No. 07805959.9.
European Invitation to Remedy Deficiencies dated Mar. 10, 2008 for EP Application No. 06796594.7.
European Office Action dated Dec. 3, 2010 for EP Application No. 07805959.9.
European Office Action dated Jun. 21, 2011 for EP Application No. 07805959.9.
European Office Action dated Sep. 26, 2011 for EP Application No. 06796594.7.
Filipino Office Action dated Dec. 16, 2011 for PH Application No. 12007502319.
Indian Amendment dated Mar. 24, 2008 for IN Application No. 1424/CHENP/2008.
Indian Office Action dated Sep. 19, 2011 for in Application No. 1424/CHENP/2008, including Response thereto dated Nov. 18, 2011.
Israeli Notice Prior to Allowance dated Sep. 12, 2011 for IL Application No. 188670 (with English translation).
Israeli Notice Prior to Examination dated Aug. 13, 2009 for IL Application No. 188670 (with English translation).
Israeli Notice Prior to Examination dated Mar. 23, 2010 for IL Application No. 197141 (with English translation).
Israeli Office Action dated Jul. 3, 2011 for IL Application No. 188670 (with English translation).
Japanese Amendment dated Dec. 25, 2007 for JP Application No. 2007-532099 (with English translation).
Japanese Amendment dated Sep. 25, 2007 for JP Application No. 2007-532099.
Japanese Decision to Grant dated Jan. 8, 2008 for JP Application No. 2007-532099 (with English translation)..
Japanese Petition dated Dec. 25, 2007 for JP Application No. 2007-532099 (with English translation).
Japanese Petition dated Sep. 25, 2007 for JP Application No. 2007-532099 (with English translation).
Jordanian Amendment dated Oct. 19, 2007 for JO Application No. 280/2006 (with partial English translation).
Korean Amendment dated Dec. 27, 2007 for KR Application No. 10-2007-7026886 (with partial English translation).
Korean Amendment dated Nov. 21, 2007 for KR Application No. 10-2007-7026886 (with partial English translation).
Korean Amendment dated Oct. 27, 2009 for KR Application No. 10-2007-7026886 (with partial English translation).
Korean Argument Brief dated Oct. 27, 2009 for KR Application No. 10-2007-7026886 (with partial English translation).
Korean Notice of Decision to Grant dated Dec. 31, 2009 for KR Application No. 10-2007-7026886 (with English translation).
Korean Office Action dated Aug. 27, 2009 for KR Application No. 10-2007-7026886 (with English translation).
Malaysian Amendment dated Jul. 17, 2008 for MY Application No. PI20071922.
Malaysian Office Action dated Jan. 15, 2010 for MY Application No. PI20071922.
Maltese Registration Letter dated Oct. 29, 2007 for MT Application No. 3723.
Maltese Registration Letter dated Sep. 29, 2007 for MT Application No. 3723.
Mexican Notice of Allowance dated Oct. 15, 2010 for MX Application No. MX/a/2008/002156 (with English translation).
New Zealand Notice of Acceptance dated Feb. 12, 2010 for NZ Application No. 566793.
New Zealand Office Action dated Dec. 4, 2009 for NZ Application No. 566793.
Pakistani Notice of Acceptance dated Nov. 2, 2010 for PK Application No. 1024/2006.
Pakistani Notice of Acceptance dated Nov. 2, 2010 for PK Application No. 375/2008.
Pakistani Office Action dated Feb. 24, 2009 for PK Application No. 1024/2006.
Pakistani Office Action dated Jul. 20, 2009 for PK Application No. 375/2008.
Response to Australian Office Action dated Jul. 16, 2009 for AU Application No. 2006282456.
Response to Australian Office Action dated Mar. 30, 2012 for Application No. 2007288793.
Response to Bangladeshi Office Action dated Dec. 13, 2007 for BD Application No. 184/2006.
Response to Canadian Office Action dated Oct. 8, 2009 for CA Application No. 2605854.
Response to Chinese Office Action dated Jul. 27, 2010 for CN Application No. 200680021939.X (with English translation).
Response to Chinese Office Action dated May 20, 2011 for CN Application No. 200680021939.X (with English translation).
Response to Chinese Office Action dated Oct. 28, 2010 for CN Application No. 200680021939.X (with English translation).
Response to European Invitation to Remedy Deficiencies dated Mar. 31, 2008 for EP Application No. 06796594.7.
Response to European Office Action dated Dec. 21, 2011 for EP Application No. 06796594.7.
Response to European Office Action dated Mar. 29, 2011 for EP Application No. 07805959.9.
Response to Israeli Notice Prior to Examination dated Jun. 1, 2010 for IL Application No. 197141 (with English translation).
Response to Israeli Notice Prior to Examination dated Nov. 22, 2009 for IL Application No. 188670 (with English translation).
Response to Israeli Office Action dated Aug. 15, 2011 for IL Application No. 188670 (with English translation).
Response to Israeli Office Action dated Oct. 25, 2011 for IL Application No. 188670 (with English translation).
Response to New Zealand Office Action dated Jan. 27, 2010 for NZ Application No. 566793.
Response to Pakistani Office Action dated Apr. 20, 2009 for PK Application No. 1024/2006.
Response to Pakistani Office Action dated Apr. 7, 2008 for PK Application No. 1024/2006.
Response to Pakistani Office Action dated Apr. 8, 2009 for PK Application No. 375/2008.
Response to Pakistani Office Action dated Jan. 29, 2009 for PK Application No. 1024/2006.
Response to Pakistani Office Action dated Sep. 1, 2009 for PK Application No. 375/2008.
Response to Russian Office Action dated Jan. 26, 2009 for RU Application No. 2008110932/04 (with English translation).
Response to Vietnamese Office Action dated May 10, 2010 for VN Application No. 1-2008-00723 (with English translation).
Russian Decision on Grant dated Feb. 6, 2009 for RU Application No. 2008110932/04 (with English translation).
Russian Office Action for dated Dec. 3, 2008 for RU Application No. 2008110932/04 (with English translation).
Saudi Arabian Amendment dated Oct. 22, 2007 for SA Application No. 06270287 (with partial English translation).

Saudi Arabian Appeal dated Jun. 23, 2010 for SA Application No. 06270287 (with English translation).
Singaporean Amendment dated on Aug. 24, 2010 for SG Application No. 200718614-1.
South African Notification of Acceptance dated Mar. 12, 2009 for ZA Application No. 2007/09572.
Sri Lankan Amendment dated Mar. 31, 2011 for LK Application No. 14703.
Taiwanese Amendment dated Mar. 20, 2009 for TW Application No. 95130665 (with English translation).
Thai Amendment dated on Sep. 25, 2007 for TH Application No. 0601004017 (with English translation).
Vietnamese Intention to Grant dated Aug. 19, 2010 for VN Application No. 1-2008-00723 (with English translation).
Vietnamese OfficeOffice Action dated Mar. 11, 2010 for VN Application No. 1-2008-00723 (with English translation).
Israeli Office Action and an English translation thereof dated Feb. 8, 2012, for Application No. 197002.
Chinese Office Action for Application No. 200780019200.X dated Apr. 6, 2012 (with English translation).
Israel Amendment filed May 2, 2012 for IL Patent Application No. 188670 (w/ English Translation).
TW Office Action dated Mar. 2, 2012 for Appl. No. 095130665 (w/ English translation).
Australian Notice of Acceptance for AU Patent Application No. 2007288793 dated Apr. 10, 2012.
Australian Second Statement of Proposed Amendments for AU Patent Application No. 2006282456 filed Apr. 26, 2012.
India Amendment for in Patent Application No. 1424/CHENP/2008 filed Apr. 27, 2012.
Norwegian Amendment for NO Patent Application No. 20080460 filed May 14, 2012 (w/ English translation).
Philippines Amendment for PH Patent Application No. 1-2007-502319 filed May 14, 2012.
European Decision to Grant a Patent, dated Jun. 1, 2012, for European Application No. 05719973.9.
Israeli Response to Notice of Defects, dated Jun. 10, 2012, for Israeli Application No. 197141.
US Notice of Allowance, dated May 25, 2012, for U.S. Appl. No. 12/558,982.
Request for Examination dated Jun. 26, 2012 for Canadian Patent Application No. 2661702.
Response to the Result of Substantative Examination Stage I filed on Jun. 11, 2012 for Indonesian Patent Application No. W-00200800601 (w/ English translation).
Submission Document(s) Before the Patent Office dated May 29, 2012 for Brazilian Patent Application No. PI0616799-3 (w/ English translation).
Australian Office Action dated Jun. 28, 2012 for AU Patent Application No. 2008217931.
English translation of Notification of Reasons for Rejection dated Sep. 29, 2009 for Japanese Patent Application No. 2006-510543.
European Office Action dated Feb. 11, 2012 for European Patent Application No. 05719973.9.
International Preliminary Report on Patentability dated Feb. 26, 2008 for PCT/JP2006/316331.
Nicolaus, B.J.R., "Symbiotic Approach to Drug Design," Decision Making in Drug Research, ed. Franz Gross. New York: Raven Press, 1983.
Response to Chinese Office Action dated Jul. 24, 2012 for Chinese Patent Application No. 200780019200.X, with English translation.
US Office Action dated Aug. 13, 2012 for U.S. Appl. No. 12/527,633.
European Notice of Allowance mailed Sep. 25, 2012 for European Patent Application No. 06796594.7.
Indian Amendment dated Sep. 11, 2012 for IN Patent Application No. 1424/CHENP/2008.
Tawainese Notice of Allowance mailed Sep. 7, 2012 for TW Patent Application No. 095130665, with English translation.
Official Notification dated Sep. 24, 2012 for Australian Patent Application No. 2006282456.
Indonesian Notice of Allowance dated Oct. 17, 2012, for Indonesian Application No. W-00200800601.
European Intention to grant, dated Nov. 9, 2012, for European Application No. 07793075.8.
Haleblian, J.K., "Characterization of Habits and Crystalline Modification of Solids and Their Pharmaceutical Applications", Journal of Pharmaceutical Sciences, vol. 64, No. 8, Aug. 1975, pp. 1269-1288.
Israeli Notice Prior to Allowance, dated Oct. 28, 2012, for Israeli Application No. 197002.
Japanese Notice of Reasons for Rejection, dated Oct. 23, 2012, for Japanese Application No. P2008-530917.
Japanese Notice of Decision to Grant a Patent dated Nov. 13, 2012 for JP Patent Application No. P2008-532065 with English translation.

* cited by examiner

PHENOXYPYRIDINE DERIVATIVE SALTS AND CRYSTALS THEREOF, AND PROCESS FOR PREPARING THE SAME

RELATED APPLICATIONS

This application claims priority to U.S. Provisional Application 60/890,769 filed on Feb. 20, 2007 as well as Japanese Patent Application 2007-36,690 filed on Feb. 16, 2007, all of which are herein incorporated by reference in their entirety.

BACKGROUND OF THE INVENTION

1. Field of the Invention

The present invention relates to phenoxypyridine derivative salts and crystals thereof that have inhibiting activity against hepatocyte growth factor receptor (hereinafter abbreviated as "HGFR") and are useful as anti-tumor agents and inhibitors for cancer metastasis, and to processes for preparing the same.

More specifically, it relates to acid addition salts of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (formula (1) below, hereinafter referred to as "Compound 1") or crystals thereof and to salts of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (formula (2) below, hereinafter referred to as "Compound 2") or crystals thereof, and to processes for preparing them.

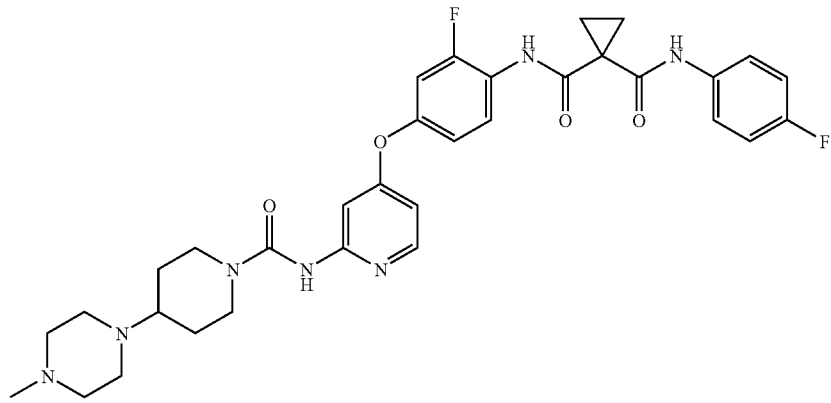

(1)

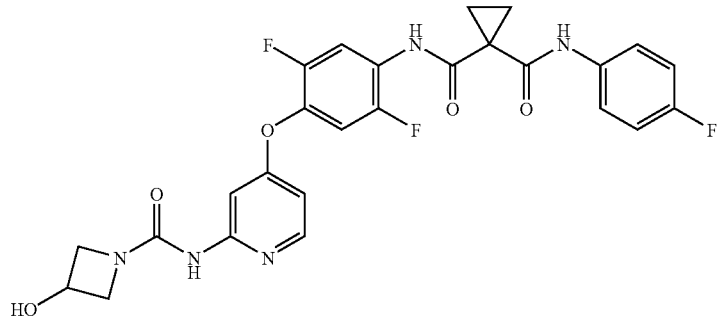

(2)

2. Related Background Art

Overexpression of HGFR is reported in various kinds of tumors such as a pancreatic cancer, a gastric cancer, a colorectal cancer, a breast cancer, a prostate cancer, a lung cancer, a renal cancer, a brain tumor, an ovarian cancer and an esophageal cancer (Non-patent documents 1 and 5). HGFR expressed in these cancer cells is considered to be involved in cancer malignancy (aberrant growth, invasion or enhanced metastasis), because HGFR causes autophosphorylation of intracellular tyrosine kinase constitutively or upon stimulation by hepatocyte growth factor (hereafter referred to as "HGF").

It is also reported that HGFR is expressed in vascular endothelial cells and is involved in tumor angiogenesis since HGF stimulates HGFR to facilitate proliferation and migration of vascular endothelial cells (non-patent document 2).

Furthermore, NK4, an antagonistic peptide for HGF, is reported to block HGF-HGFR signal to inhibit invasion of cancer cells and tumor angiogenesis (non-patent documents 3 and 4).

Therefore, a compound having inhibitory activity against HGFR is expected to be useful as an anti-tumor agent, an angiogenesis inhibitor or an inhibitor for cancer metastasis.

Incidentally, Patent document 1 discloses phenoxypyridine derivatives having inhibitory activity against HGFR and processed for preparing the same, but neither discloses nor suggests Compound 1 and Compound 2, nor salts of Compound 1 and Compound 2 or crystals thereof, nor processes for preparing the same.

[Patent document 1] WO 2005/082855
[Non-patent document 1] Oncology Reports, 5, 1013-1024 (1998)
[Non-patent document 2] Advances in Cancer Research, 67, 257-279 (1995)
[Non-patent document 3] British Journal of Cancer, 8, 864-873 (2001)
[Non-patent document 4] Cancer Sci., 94, 321-327 (2003)
[Non-patent document 5] Oncogene, 25(3), 409-418 (2006)

SUMMARY OF THE INVENTION

It is an object of the present invention to provide phenoxypyridine derivative salts or crystals thereof, which exhibit inhibitory activity against HGFR, are useful as anti-tumor agents and inhibitors for cancer metastasis, have excellent physical properties and are highly useful as medicaments, as well as processes for preparing the same.

In order to achieve the object stated above, the invention provides the following:

<1> An acid addition salt of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, wherein the acid is selected, from the group consisting of hydrochloric acid, hydrobromic acid, sulfuric acid, fumaric acid, succinic acid, malic acid, maleic acid and tartaric acid;

<2> Crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide malate;

<3> Crystals according to <2>, which have diffraction peaks at diffraction angles (2θ±0.2°) of 17.7°, 19.0° and 23.5° in an X-ray powder diffraction;

<4> Crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide tartrate;

<5> Crystals according to <4>, which have diffraction peaks at diffraction angles (2θ±0.2°) of 12.2°, 17.7° and 23.4° in an X-ray powder diffraction;

<6> Crystals according to <4>, which have peaks at chemical shifts (+0.5 ppm) of 175.7 ppm, 166.7 ppm, 154.9 ppm and 45.7 ppm in a $^{13}$C solid nuclear magnetic resonance spectrum;

<7> An acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, wherein the acid is selected from the group consisting of hydrochloric acid, hydrobromic acid, sulfuric acid, methanesulfonic acid, ethanesulfonic acid, benzenesulfonic acid and 4-methylbenzenesulfonic acid;

<8> Crystals of an acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, wherein the acid is selected from the group consisting of hydrochloric acid, hydrobromic acid, sulfuric acid, ethanesulfonic acid and benzenesulfonic acid;

<9> Crystals of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide methanesulfonate.

<10> Crystals according to <9>, which have diffraction peaks at diffraction angles (2θ±0.2°) of 17.7°, 20.4° and 21.7° in an X-ray powder diffraction;

<11> Crystals of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1'-dicarboxyamide 4-methylbenzenesulfonate;

<12> Crystals according to <11>, which have diffraction peaks at diffraction angles (2θ±0.2°) of 7.2°, 17.31 and 23.6° in an X-ray powder diffraction;

<13> A process for preparing crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide malate, characterized by mixing N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, a solvent selected from ketones and alcohols, and malic acid to form a solution, and then depositing crystals;

<14> A process for preparing crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide tartrate, characterized by mixing N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, a solvent selected from ketones and alcohols, water, and tartaric acid to form a solution, and then depositing crystals;

<15> A process for preparing crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide tartrate, characterized by mixing N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, water and tartaric acid to form a solution, and then adding a solvent selected from ketones and alcohols to deposit crystals;

<16> A process for preparing crystals of an acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, characterized by mixing. N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, a solvent selected from ketones and alcohols and an acid selected from the group consisting of hydrochloric acid, hydrobromic acid, sulfuric acid, methanesulfonic acid, ethanesulfonic acid, benzenesulfonic acid and 4-methylbenzenesulfonic acid to form a solution, and then depositing crystals;

<17> A pharmaceutical composition comprising crystals according to any one of <2> to <6>;

<18> An anti-tumor agent comprising crystals according to any one of <2> to <6>;

<19> An inhibitor for cancer metastasis comprising crystals according to any one of <2> to <6>;

<20> A pharmaceutical composition comprising crystals according to any one of <8> to <12>;

<21> An anti-tumor agent comprising crystals according to any one of <8> to <12>;

<22> An inhibitor for cancer metastasis comprising crystals according to any one of <8> to <12>;

<23> A method for preventing or treating cancer comprising administering to a patient, a pharmacologically effective dose of crystals according to any one of <2> to <6>;

<24> Use of crystals according to any one of <2> to <6> for the manufacture of a prophylactic or therapeutic agent for cancer;

<25> A method for preventing or treating cancer comprising administering to a patient, a pharmacologically effective dose of crystals according to any one of <8> to <12>; and <26> Use of crystals according to any one of <8> to <12> for the manufacture of a prophylactic or therapeutic agent for cancer.

Effect of the Invention

The phenoxypyridine derivative salts and crystals thereof according to the invention have excellent physical properties (solubility, stability, etc.) and are useful as anti-tumor agents, angiogenesis inhibitors and inhibitors for cancer metastasis for various types of tumors including a pancreatic cancer, a gastric cancer, a colorectal cancer, a breast cancer, a prostate cancer, a lung cancer, a renal cancer, a brain tumor, an ovarian cancer and an esophageal cancer.

DESCRIPTION OF THE PREFERRED EMBODIMENTS

Figure 1:
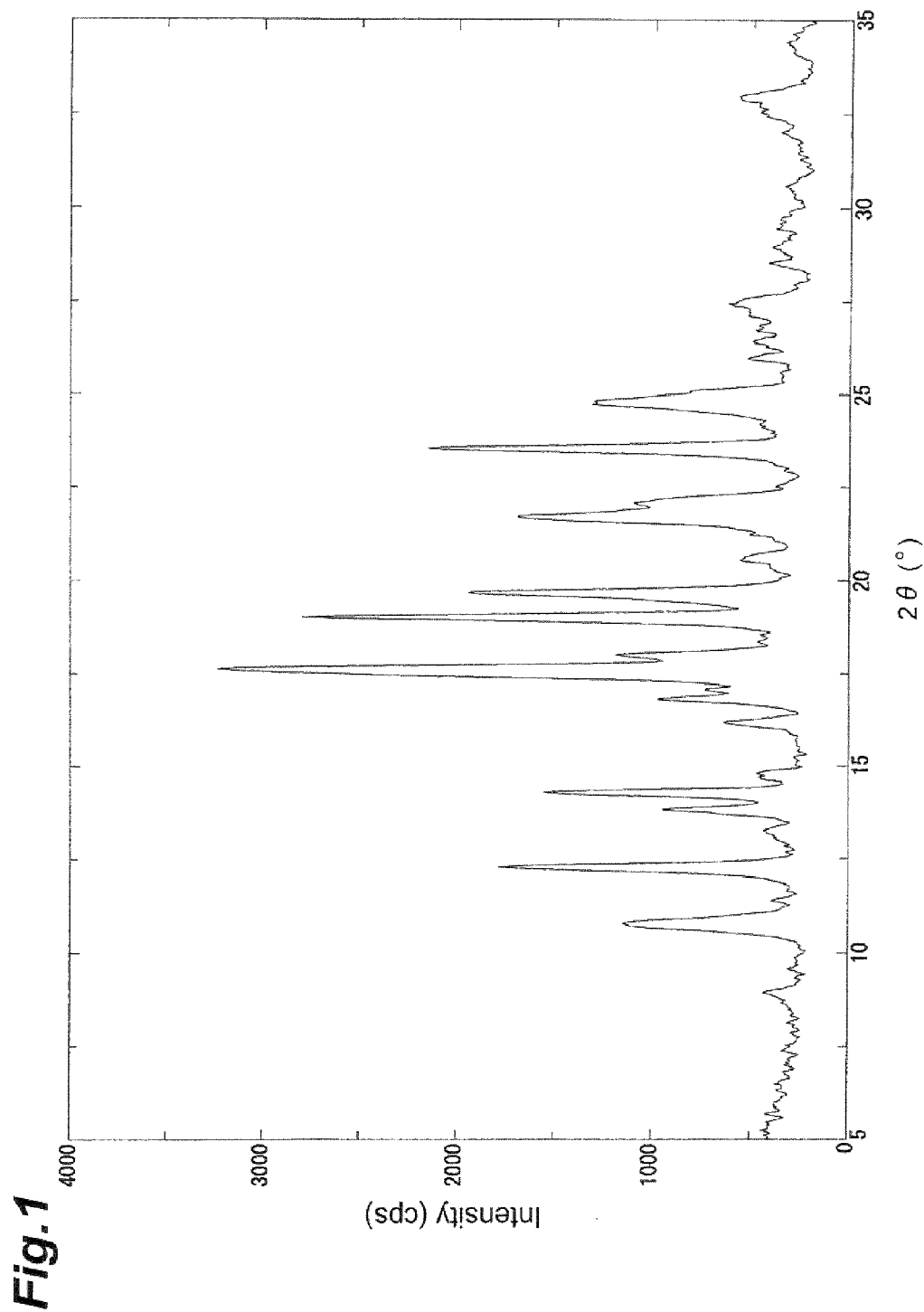
FIG. 1 shows an X-ray powder diffraction pattern for crystals of the malate of Compound 1 obtained in Example 1-7 (Method 1).
Figure 2:
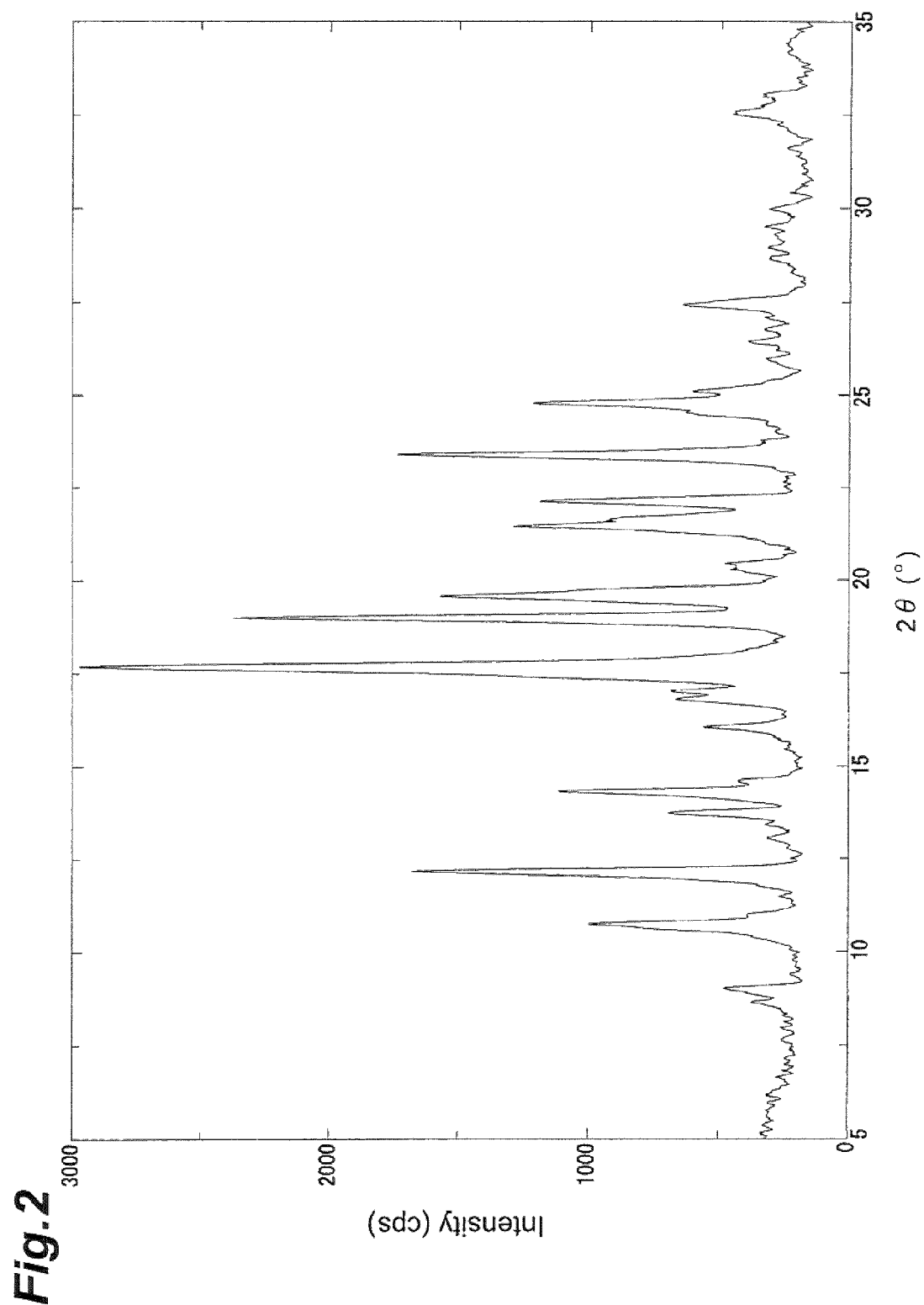
FIG. 2 shows an X-ray powder diffraction pattern for crystals of the tartarate of Compound 1 obtained in Example 1-8 (Method 1).
Figure 3:
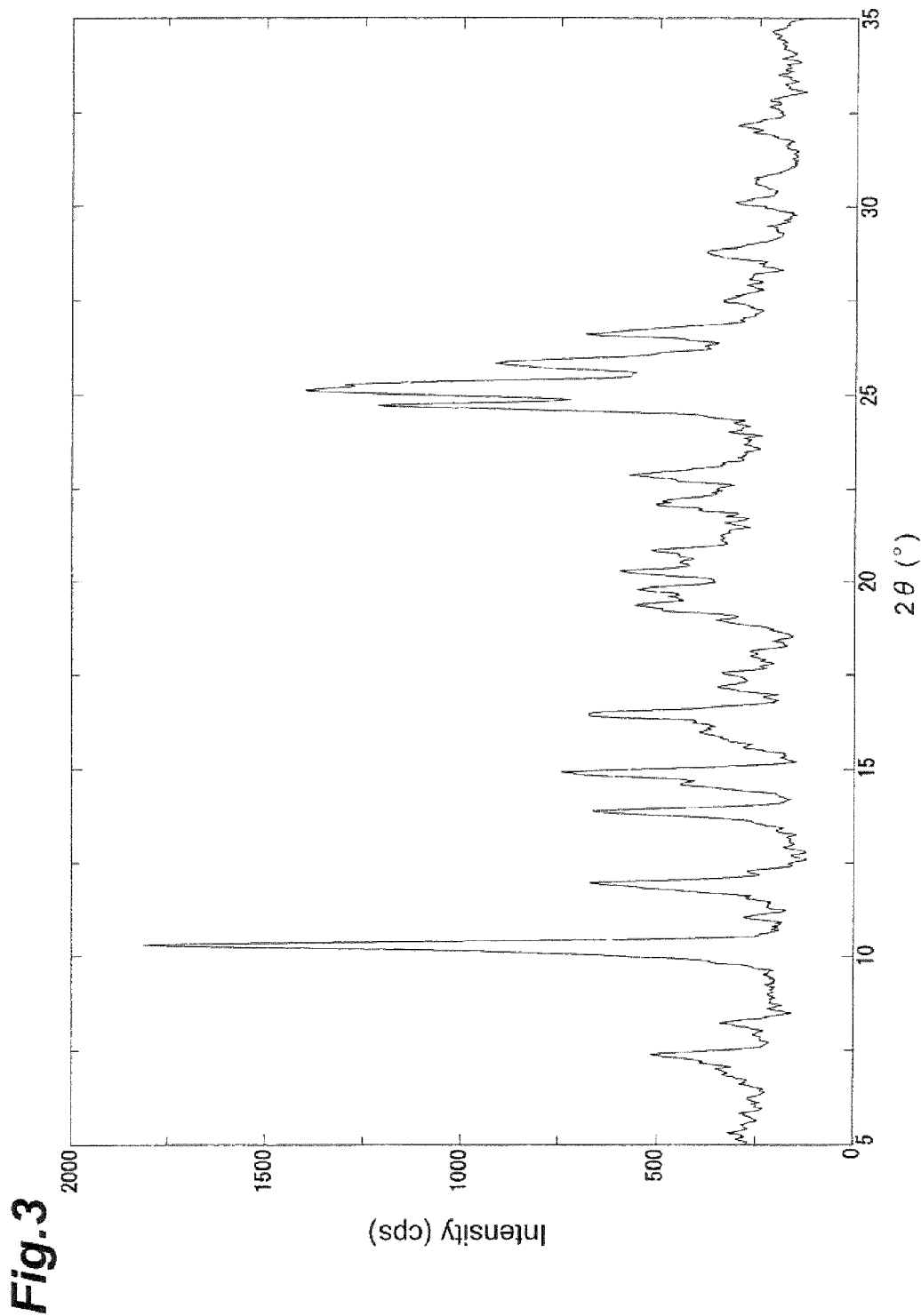
FIG. 3 shows an X-ray powder diffraction pattern for crystals of the hydrochloride of Compound 2 obtained in Example 2-1.
Figure 4:
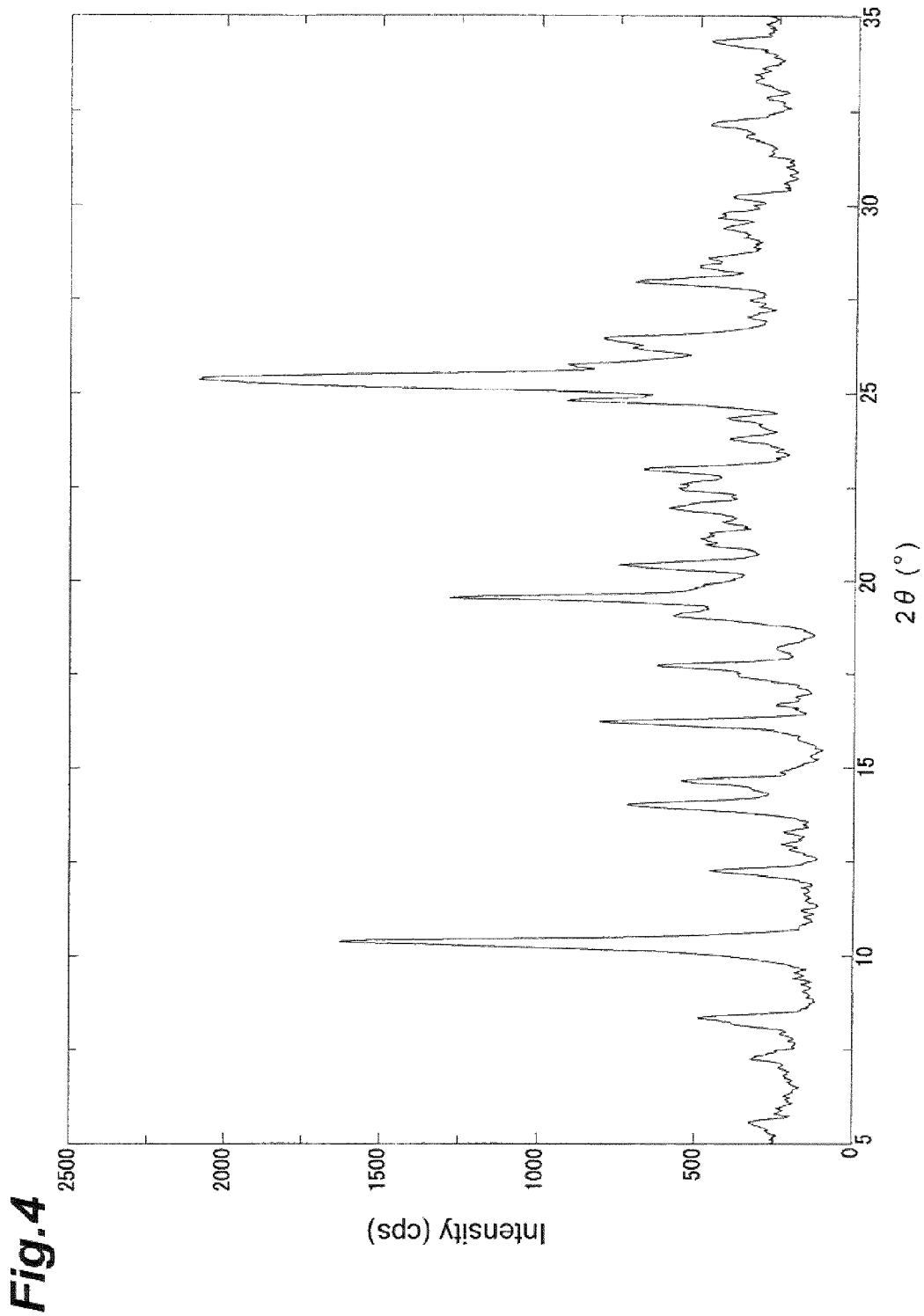
FIG. 4 shows an X-ray powder diffraction pattern for crystals of the hydrobromide of Compound 2 obtained in Example 2-2.
Figure 5:
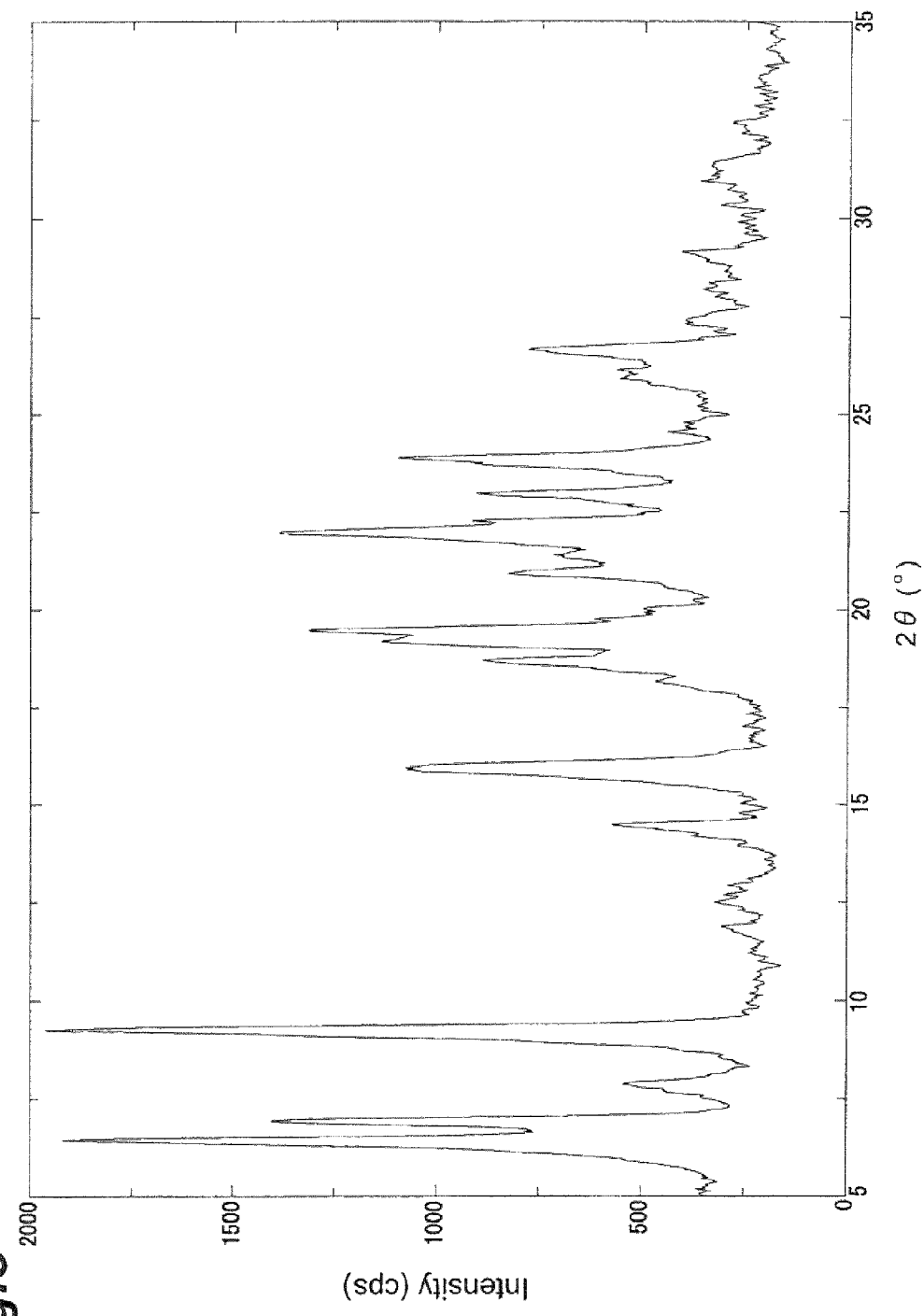
FIG. 5 shows an X-ray powder diffraction pattern for crystals of the ½ sulfate of Compound 2 obtained in Example 2-3.
Figure 6:
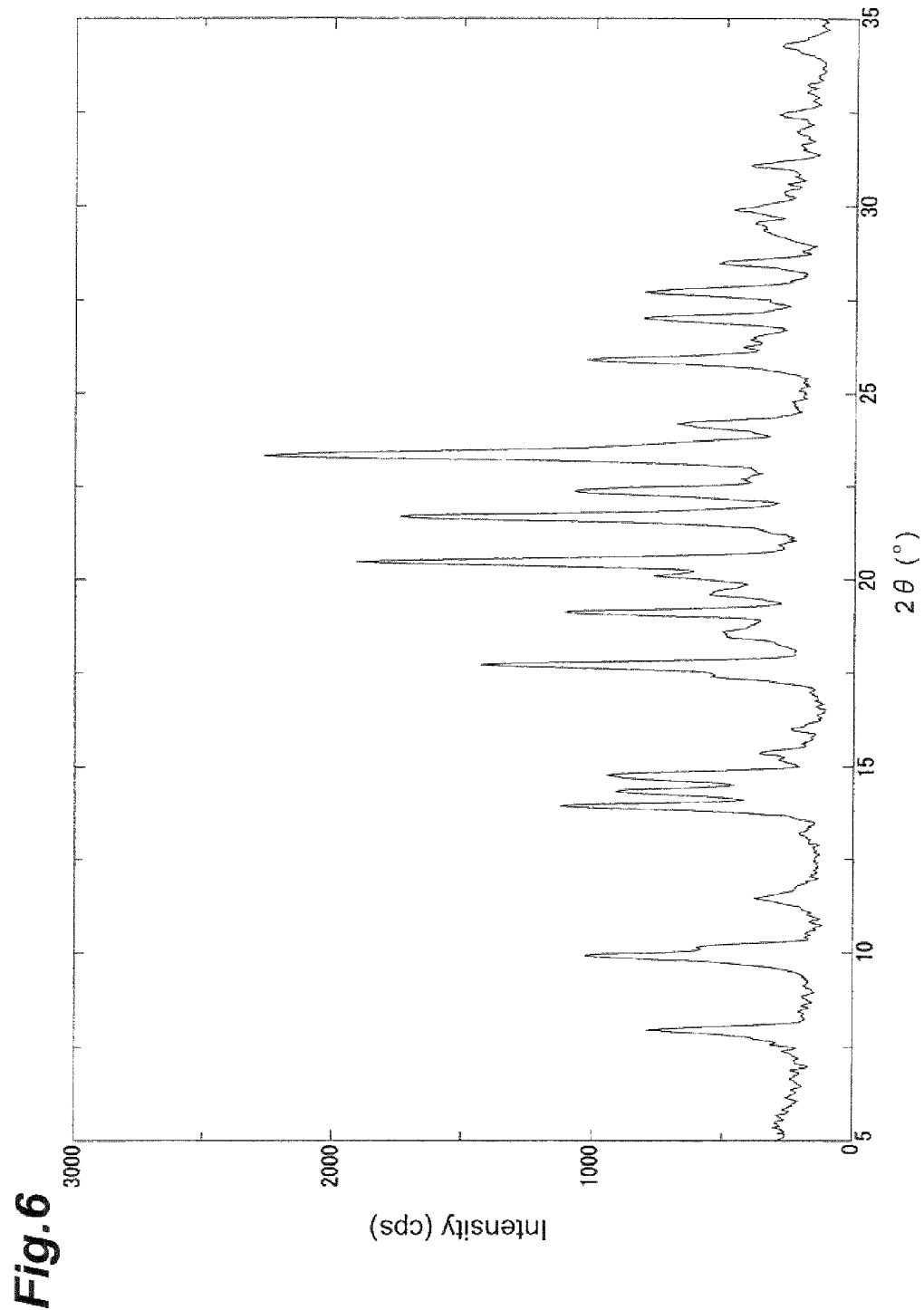
FIG. 6 shows an X-ray powder diffraction pattern for crystals of the methanesulfonate of Compound 2 obtained in Example 2-4 (Method 1).
Figure 7:
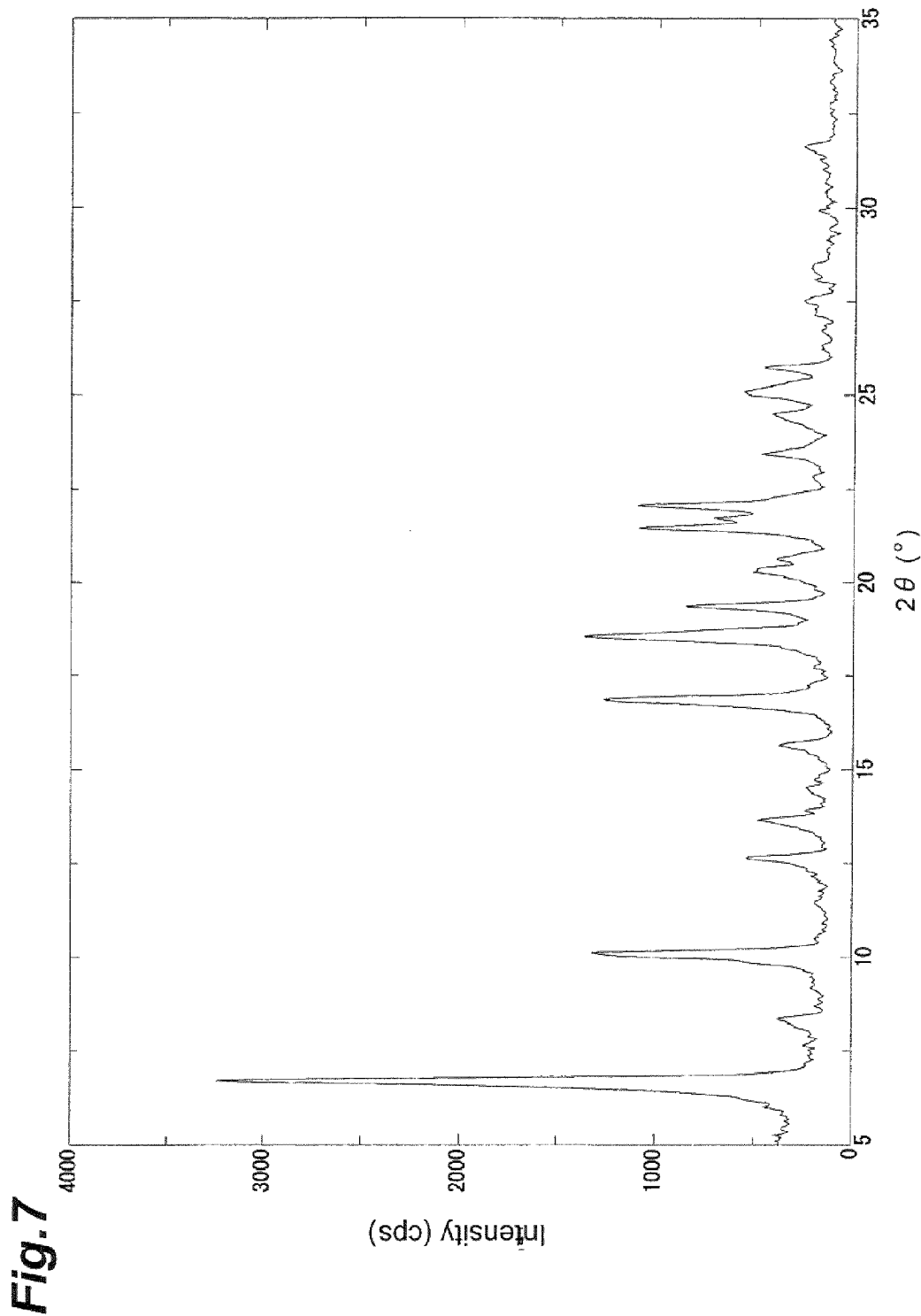
FIG. 7 shows an X-ray powder diffraction pattern for crystals of the ethanesulfonate of Compound 2 obtained in Example 2-5.
Figure 8:
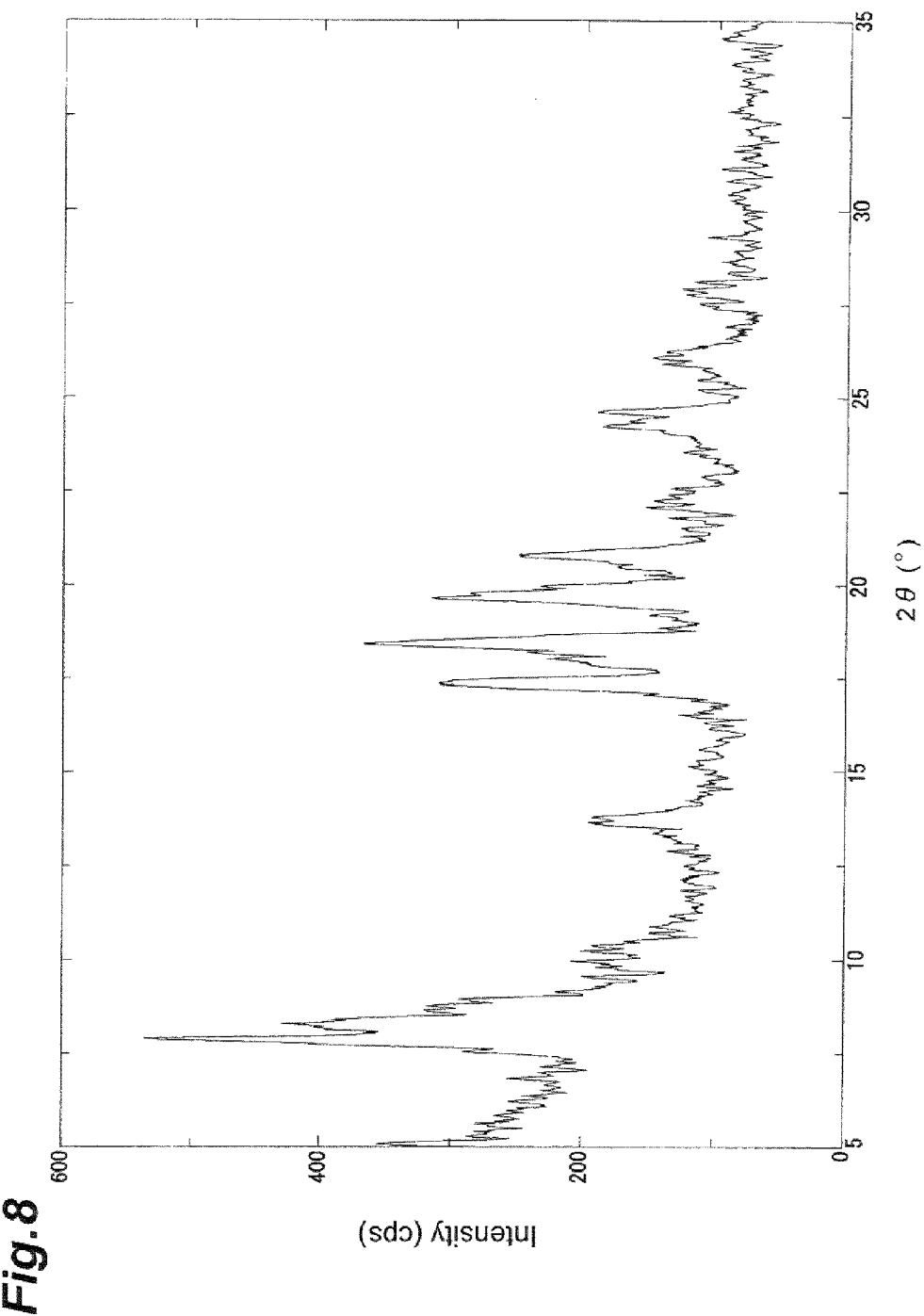
FIG. 8 shows an X-ray powder diffraction pattern for crystals of the benzenesulfonate of Compound 2 obtained in Example 2-6.
Figure 9:
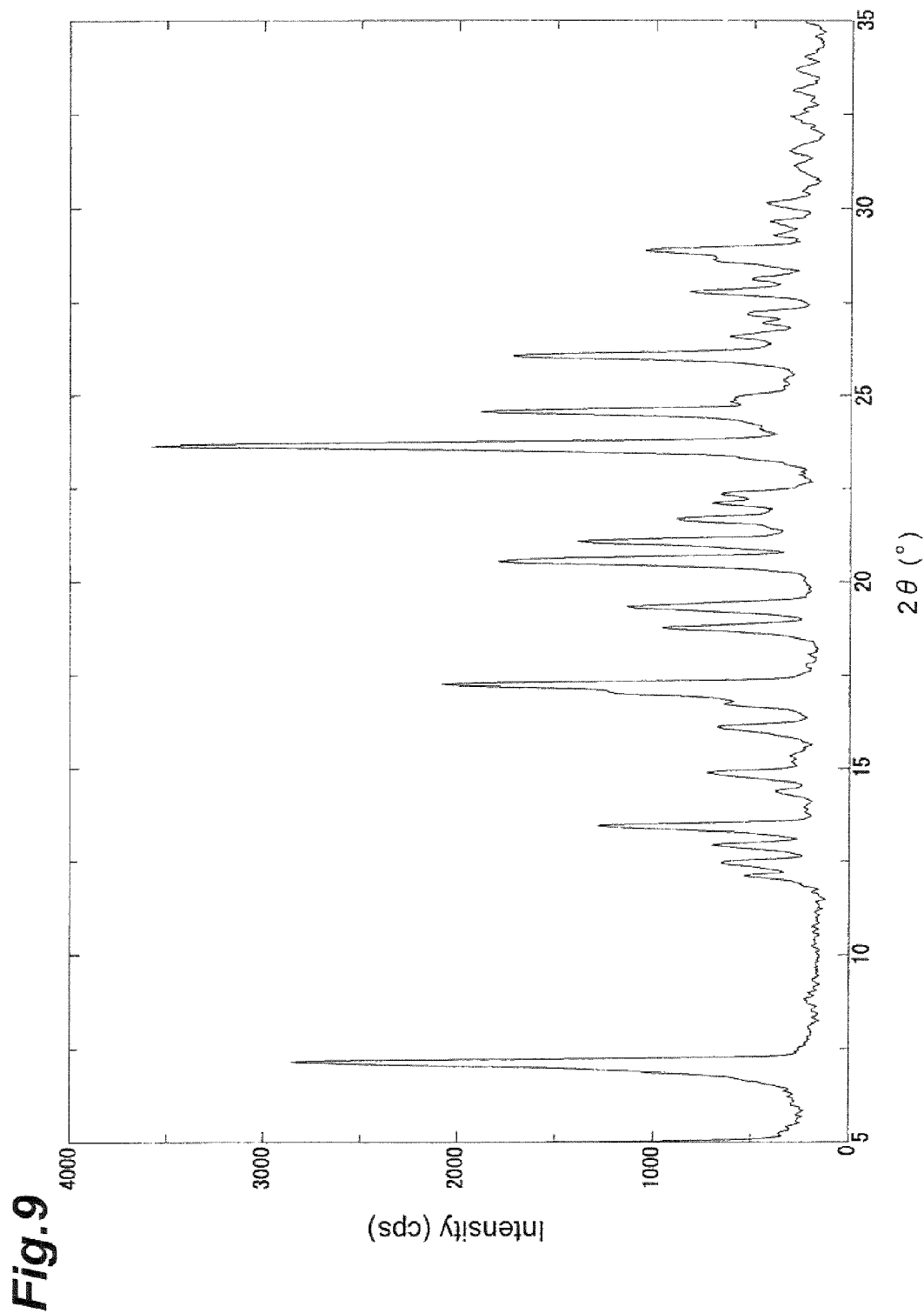
FIG. 9 shows an X-ray powder diffraction pattern for crystals of the 4-methylbenzenesulfonate of Compound 2 obtained in Example 2-7 (Method 1).
Figure 10:
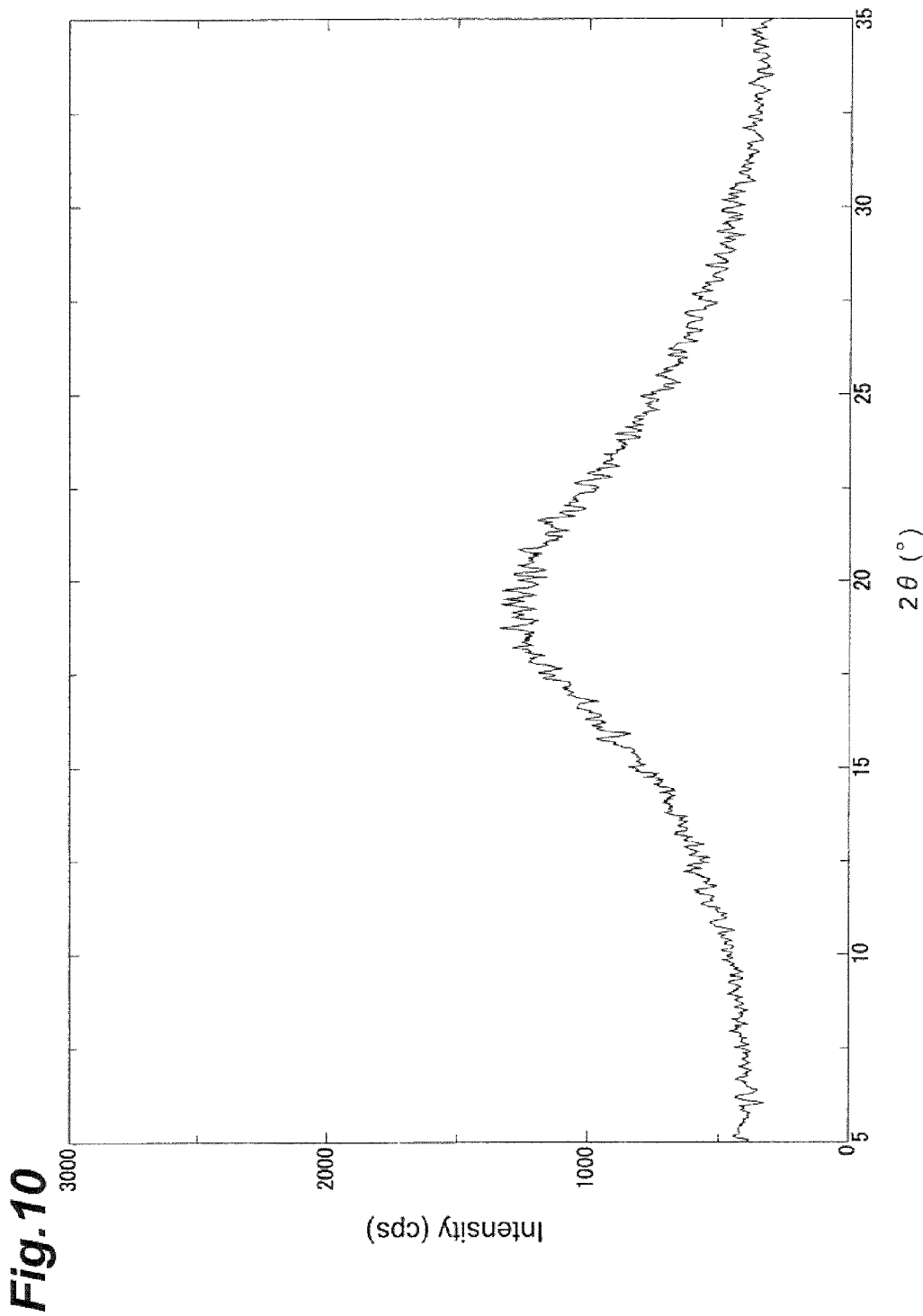
FIG. 10 shows an X-ray powder diffraction pattern for the amorphous malate of Compound 1 obtained in Example 1-7 (Method 2).
Figure 11:
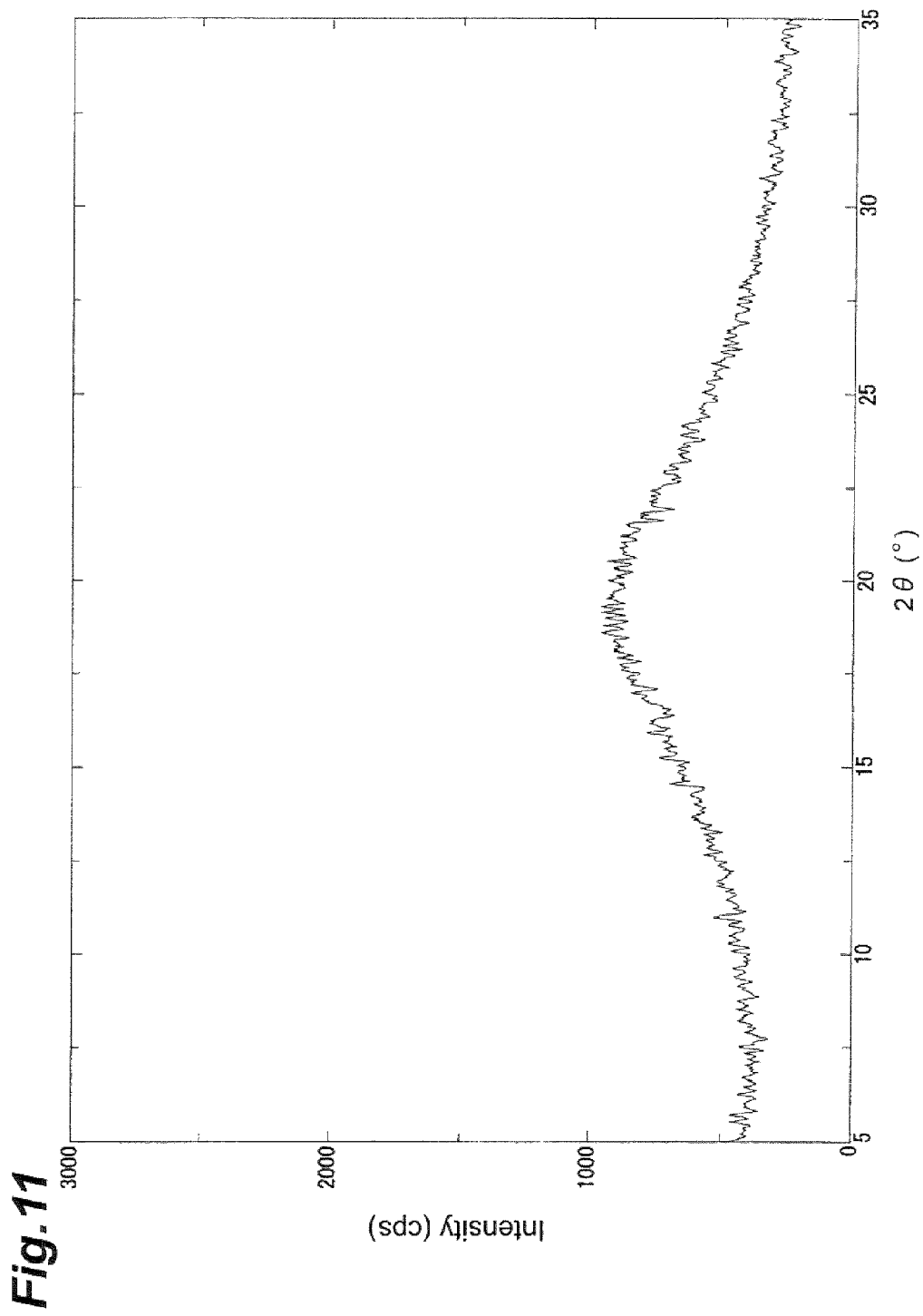
FIG. 11 shows an X-ray powder diffraction pattern for the amorphous tartarate of Compound 1 obtained in Example 1-8 (Method 5).
Figure 12:
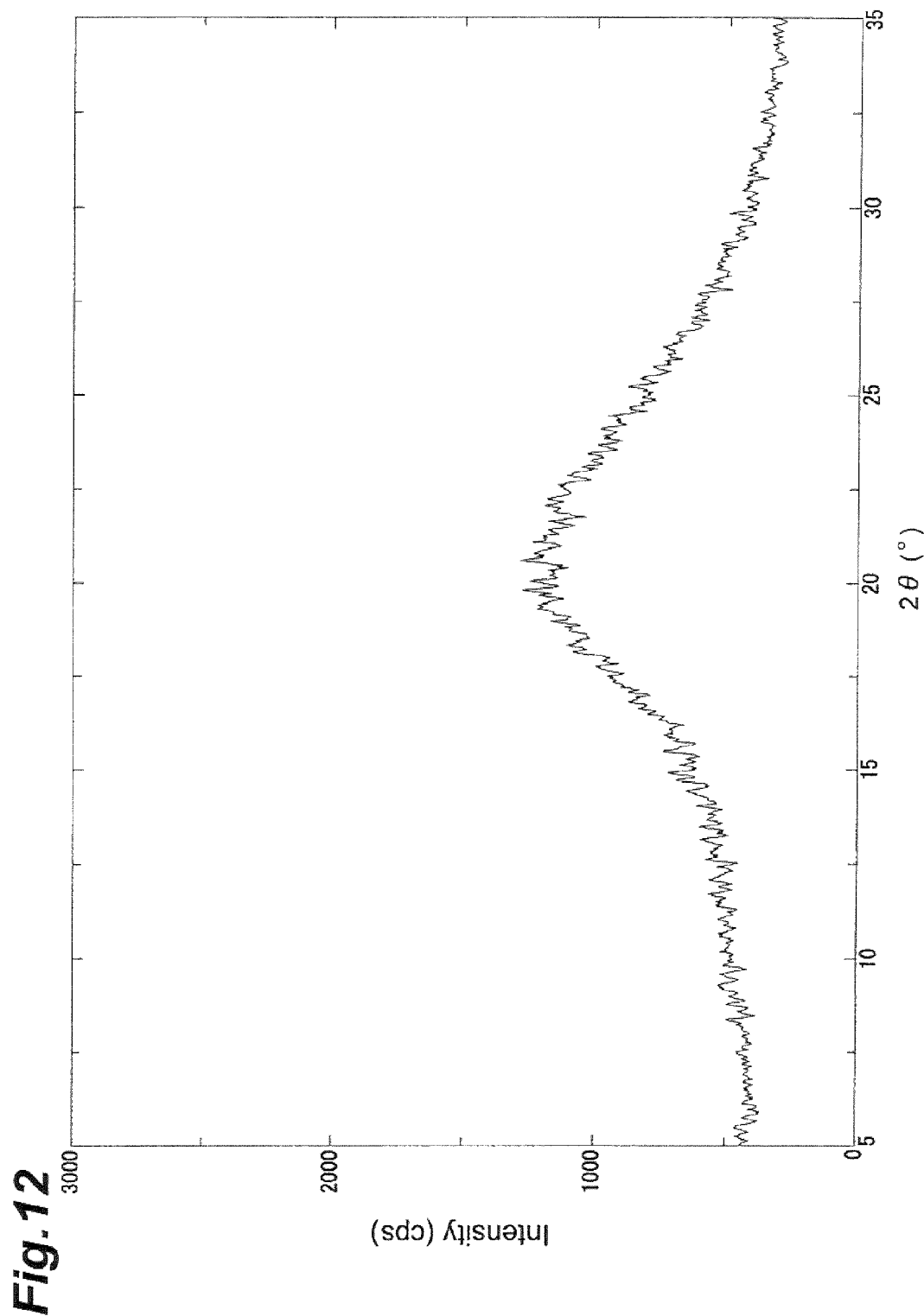
FIG. 12 shows an X-ray powder diffraction pattern for the amorphous methanesulfonate of Compound 2 obtained in Example 2-4 (Method 2).
Figure 13:
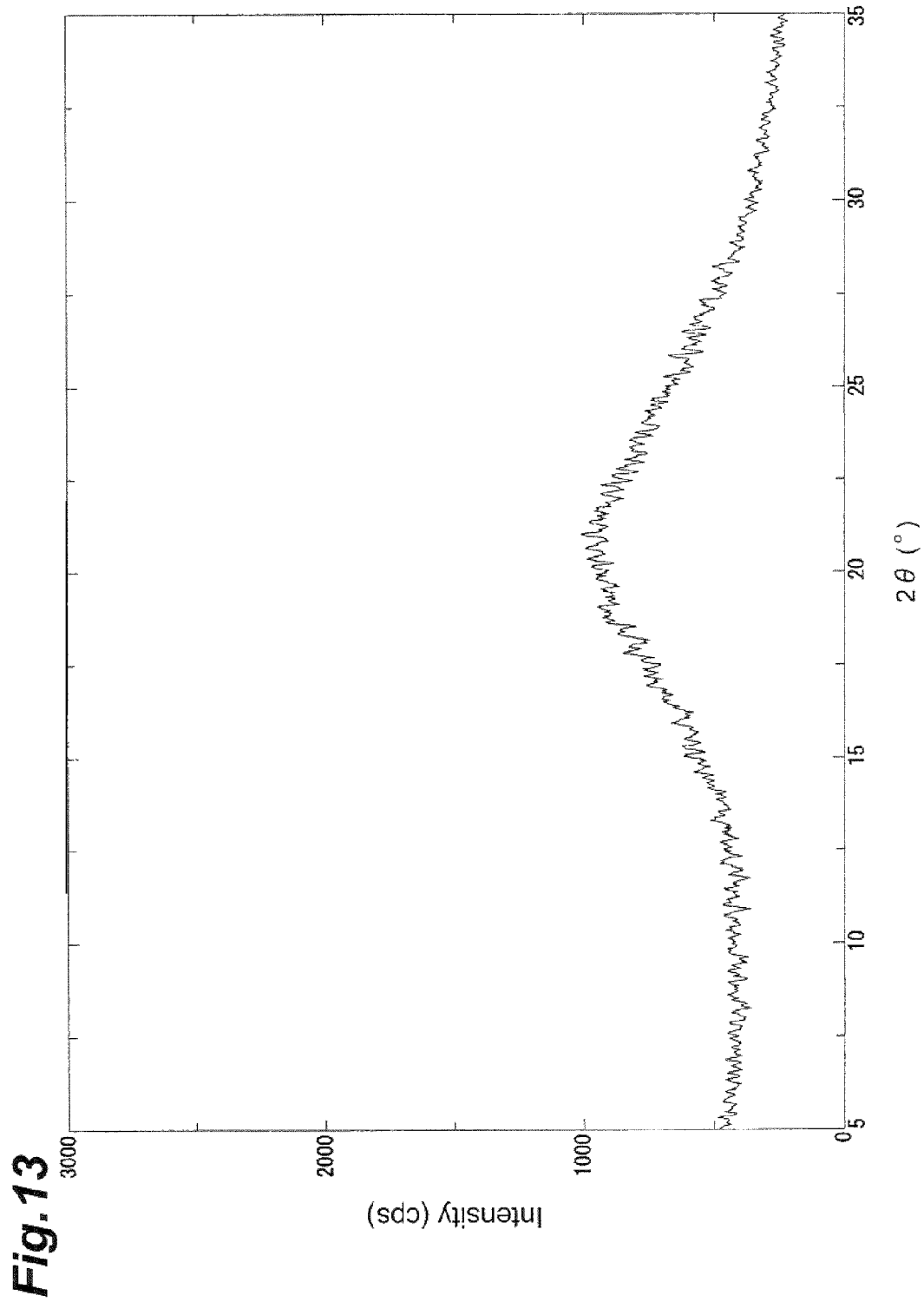
FIG. 13 shows an X-ray powder diffraction pattern for crystals of the 4-methylbenzenesulfonate of Compound 2 obtained in Example 2-7 (Method 2).

The present invention will now be explained in greater detail.

The acid addition salt of the invention is 1) an acid addition salt of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (Compound 1) wherein the acid is selected from the group consisting of hydrochloric acid, hydrobromic acid, sulfuric acid, fumaric acid, succinic acid, malic acid, maleic acid and tartaric acid, or 2) an acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (Compound 2) wherein the acid is selected from the group consisting of hydrochloric acid, hydrobromic acid, sulfuric acid, methanesulfonic acid, ethanesulfonic acid, benzenesulfonic acid and 4-methylbenzenesulfonic acid. An acid addition salt of the invention may be a nonsolvate or a solvate such as a hydrate, and there is no limitation to the number of molecules in the added acid. Acid addition salts according to the invention include not only the following crystals of the invention, but also amorphous acid addition salts of Compound 1 and amorphous acid addition salts of Compound 2.

The crystals according to the invention are 1) crystals of malate of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (Compound 1), 2) crystals of tartarate of Compound 1, 3) crystals of hydrochloride of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (Compound 2), 4) crystals of hydrobromide of Compound 2, 5) crystals of ½ sulfate of Compound 2, 6) crystals of methanesulfonate of Compound 2, 7) crystals of ethanesulfonate of Compound 2, 8) crystals of benzenesulfonate of Compound 2 and 9) crystals of 4-methylbenzenesulfonate of Compound 2. The crystals of malate of Compound 1 include crystals of D-malate and crystals of L-malate of Compound 1, and crystals of tartarate of Compound 1 include crystals of D-tartarate and crystals of L-tartarate of Compound 1.

Crystals of malate of Compound 1 have diffraction peaks at diffraction angles (2θ±0.2°) of 17.7°, 19.0° and 23.5° in an X-ray powder diffraction, and preferably diffraction peaks at 10.8°, 12.3°, 14.3°, 17.7°, 19.0°, 19.7°, 21.7°, 22.0°, 23.5° and 24.7°.

Crystals of tartarate of Compound 1 have diffraction peaks at diffraction angles (2θ±0.2°) of 12.2°, 17.7° and 23.4° in an X-ray powder diffraction, and preferably diffraction peaks at 10.7°, 12.2°, 14.3°, 17.7°, 19.0°, 19.6°, 21.4°, 22.1°, 23.4° and 24.8°.

Crystals of hydrochloride of Compound 2 have diffraction peaks at diffraction angles (2θ±0.2°) of 7.4°, 10.3°, 12.0°, 13.9°, 15.0°, 16.5°, 24.7°, 25.1°, 25.9° and 26.6° in an X-ray powder diffraction.

Crystals of hydrobromide of Compound 2 have diffraction peaks at diffraction angles (2θ±0.2°) of 8.3°, 10.4°, 12.2°, 14.0°, 16.2°, 17.7°, 19.5°, 20.4°, 25.3° and 28.0° in an X-ray powder diffraction.

Crystals of ½ sulfate of Compound 2 have diffraction peaks at diffraction angles (2θ±0.2°) of 6.5°, 6.9°, 9.3°, 16.0°, 18.7°, 19.5°, 22.0°, 22.9°, 23.9° and 26.7° in an X-ray powder diffraction.

Crystals of methanesulfonate of Compound 2 have diffraction peaks at diffraction angles (2θ±0.2°) of 17.7°, 20.4° and 21.7° in an X-ray powder diffraction, and preferably diffraction peaks at 7.9°, 9.9°, 13.9°, 17.7°, 19.1°, 20.4°, 21.7°, 22.4°, 23.3° and 25.8°.

Crystals of ethanesulfonate of Compound 2 have diffraction peaks at diffraction angles (2θ±0.2°) of 6.7°, 10.1°, 12.7°, 13.7°, 16.9°, 18.5°, 19.4°, 21.5°, 22.1° and 23.4° in an X-ray powder diffraction.

Crystals of benzenesulfonate of Compound 2 have diffraction peaks at diffraction angles (2θ±0.2°) of 7.8°, 8.3°, 8.8°, 13.7°, 17.4°, 18.5°, 19.7°, 20.8°, 24.3° and 24.6° in an X-ray powder diffraction.

Crystals of 4-methylbenzenesulfonate of Compound 2 have diffraction peaks at diffraction angles (2θ±0.2°) of 7.2°, 17.3° and 23.6° in an X-ray powder diffraction, and preferably diffraction peaks at 7.2°, 13.4°, 17.3°, 18.8°, 19.3°, 20.6°, 21.1°, 23.6°, 24.6° and 26.1°.

Since an error within a range of ±0.2° can occur for a diffraction angle (2θ) in an X-ray powder diffraction in general, it is necessary that the above diffraction angle values are understood to also include numerical values within a range of ±0.2° thereof. Therefore, the present invention encompasses crystals for which diffraction angles match within an error range of ±0.2° in X-ray powder diffraction, as well as crystals for which diffraction angles completely match in an X-ray powder diffraction.

Crystals of tartarate of Compound 1 have peaks at chemical shifts (±0.5 ppm) of 175.7 ppm, 166.7 ppm, 154.9 ppm and 45.7 ppm in a $^{13}C$ solid nuclear magnetic resonance spectrum (hereunder referred to as $^{13}C$ solid NMR spectrum).

Since some degree of error can occur for a chemical shift (ppm) in a $^{13}C$ solid NMR spectrum in general, the invention encompasses not only crystals for which peaks (chemical shifts) in a $^{13}C$ solid NMR spectrum completely match, but also crystals having peaks substantially equivalent to chemical shifts when a $^{13}C$ solid NMR spectrum is measured under normal measuring conditions or under substantially the same conditions as described in the present specification, and specifically it is interpreted as including values in a range of about ±0.5 ppm. Specifically, for example, the present invention encompasses crystals for which peaks (chemical shifts) match within an error range of about ±0.5 ppm in a $^{13}C$ solid NMR spectrum, as well as crystals for which peaks completely match.

[General Process for Preparation]

Processes for preparing, crystals of salts of Compound 1 and Compound 2 according to the invention will now be described.

1. Process for Preparing Crystals of Malate of Compound 1

Crystals of malate of Compound 1 can be prepared by mixing Compound 1, a solvent and malic acid to form a solution and then allowing the crystals to deposit.

More specifically, for example, Crystals of malate of Compound 1 can be prepared by mixing Compound 1 and a solvent at room temperature and adding malic acid at room temperature or under heated conditions to form a solution, then allowing the solution to slowly cool to between around 4° C. and room temperature to deposit the crystal. The solution is preferably stirred while being allowed to slowly cool.

The solvent used may be ketones such as acetone or alcohols such as ethanol, 1-propanol or 2-propanol, with ethanol being preferred.

The solvent volume is not particularly restricted but is preferably 5-30 times the volume of Compound 1.

The amount of malic acid used may be 1.0-1.5 equivalents with respect to Compound 1.

The heating temperature is not particularly restricted but is preferably 40° C.-60° C.

The slow cooling from heating: temperature to room temperature (or around 4° C.) may be carried out in a period between 5 minutes and 24 hours.

2. Process for Preparing Crystals of Tartarate of Compound 1

Crystals of tartarate of Compound 1 can be prepared by mixing Compound 1, a solvent and tartaric acid to form a solution, and then allowing the crystals to deposit.

More specifically, for example, 1) Crystals of tartarate of Compound 1 can be prepared by mixing Compound 1 and a solvent at room temperature and adding water and tartaric acid at room temperature or under heated, conditions to form a solution, then allowing the solution, to slowly cool to between around 4° C. and room temperature to deposit crystals. The solution is preferably stirred while being allowed to cool. Alternatively, 2) Crystals of tartarate of Compound 1 can be prepared by mixing Compound 1 and water at room temperature and adding tartaric acid at room temperature to form an aqueous solution, then adding a solvent to the aqueous solution while stirring to deposit crystals. Alternatively, 3) Crystals of tartarate of Compound 1 can be prepared by adding a solution of Compound 1 to an aqueous solution of tartaric acid and adding a solvent to the solution while stirring to deposit crystals.

As the solvents there may be used, for example, ketones such as acetone and alcohols such as ethanol, 1-propanol and 2-propanol, among which acetone and ethanol are preferred.

The solvent volume is not particularly restricted but is preferably 5-30 times the volume of Compound 1.

The amount of tartaric acid used may be 1.0-1.5 equivalents with respect to Compound 1.

The heating temperature is not particularly restricted but is preferably 40° C.-60° C.

The slow cooling from heating temperature to room temperature (or around 4° C.) may be carried out for 5 minutes-24 hours.

3. Process for Preparing Crystals of an Acid Addition Salt of Compound 2

Crystals of an acid addition salt of Compound 2 can be prepared by mixing Compound 2, a solvent and an acid to form a solution, and then allowing the crystals to deposit.

More specifically, for example, Crystals of an acid addition salt of Compound 2 can be prepared by mixing Compound 2 and a solvent at room temperature, and adding an acid selected from the group consisting of hydrochloric acid, hydrobromic acid, sulfuric acid, methanesulfonic acid, ethanesulfonic acid, benzenesulfonic acid and 4-methylbenzenesulfonic acid at room temperature or under heated conditions to form a solution, then allowing the solution to slowly cool to between around 4° C. and room temperature to deposit the crystals. The solution is preferably stirred while being allowed to slowly cool.

The solvent used may be ketones such as acetone or alcohols such as ethanol, 1-propanol or 2-propanol, with ethanol being preferred. Water may also be added to the solvent in some cases.

The solvent volume is not particularly restricted but is preferably 10-20 times the volume of Compound 2.

The amount of acid used may be 1.0-1.5 equivalents with respect to Compound 2.

The heating temperature is not particularly restricted but is preferably 40° C.-60° C.

The slow cooling from heating temperature to room temperature (or around 4° C.) may be carried out for 5 minutes-24 hours.

When crystals of the invention are used as medicaments, the crystals of the invention will usually be combined with appropriate additives and formulated for use. However, this does not negate the use of the crystals of the invention in bulk forms as medicaments.

Such additives may include: excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like which are commonly used in medicaments, and they may be added in appropriate combinations as desired.

As examples of such excipients there may be mentioned lactose, white soft sugar, glucose, corn starch, mannitol, sorbitol, starch, pregelatinized starch, dextrin, crystalline cellulose, soft silicic anhydride, aluminum silicate, calcium silicate, magnesium aluminometasilicate, calcium hydrogenphosphate, and the like.

As examples of binders there may be mentioned polyvinyl alcohol, methylcellulose, ethylcellulose, gum Arabic, tragacanth, gelatin, shellac, hydroxypropylmethylcellulose, hydroxypropylcellulose, carboxymethylcellulose sodium, polyvinylpyrrolidone, macrogol, and the like.

As examples of lubricants there may be mentioned magnesium stearate, calcium stearate, sodium stearyl fumarate, talc, polyethylene glycol, colloidal silica, and the like.

As examples of disintegrators, there may be mentioned crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch, and carboxymethyl starch sodium, and the like.

As coloring agents there may be mentioned those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

As taste correctives there may be mentioned cocoa powder, menthol, aromatic powders, *mentha* oil, borneol, powdered cinnamon bark, and the like.

As emulsifiers or surfactants there may be mentioned stearyl triethanolamine, sodium lauryl sulfate, lauryl aminopropionic acid, lecithin, glycerin monostearate, sucrose fatty acid esters, glycerin fatty acid esters, and the like.

As dissolving aids there may be mentioned polyethylene glycol, propylene glycol, benzyl benzoate, ethanol, cholesterol, triethanolamine, sodium carbonate, sodium citrate, polysorbate 80, nicotinamide, and the like.

As suspending agents there may be mentioned the surfactants referred to above, as well as hydrophilic polymers such as polyvinyl alcohol, polyvinylpyrrolidone, methylcellulose, hydroxymethylcellulose, hydroxyethylcellulose, hydroxypropylcellulose and the like.

As isotonizing agents there may be mentioned glucose, sodium chloride, mannitol, sorbitol and the like.

As buffering agents there may be mentioned buffering solutions of phosphate, acetate, carbonate, citrate and the like.

As antiseptic agents there may be mentioned methylparaben, propylparaben, chlorobutanol, benzyl alcohol, phenethyl alcohol, dehydroacetic acid, sorbic acid, and the like.

As antioxidants there may be mentioned sulfite, ascorbic acid, α-tocopherol, and the like.

As formulations there may be mentioned oral forms such as tablets, powders, granules, capsules, syrups, lozenges and inhalants; external forms such as suppositories, ointments, eye salves, tapes, eye drops, nose drops, ear drops, poultices, lotions, and the like; and injections.

The aforementioned oral forms may be formulated with appropriate combinations of the additives mentioned above. Their surfaces may also be coated if necessary.

The aforementioned external forms may be formulated with appropriate combinations of the additives mentioned above, and especially excipients, binders, taste correctives, emulsifiers, surfactants, dissolving aids, suspending agents, isotonizing agents, antiseptic agents, antioxidants, stabilizers and absorption accelerators.

Injections may also be formulated with appropriate combinations of the additives mentioned above, and especially emulsifiers, surfactants, dissolving aids, suspending agents, isotonizing agents, buffering agents, antiseptic agents, antioxidants, stabilizers and absorption accelerators.

When crystals of the invention are used as medicaments, their daily dosage will depend on the symptoms and age of the patient but will normally be 0.1 mg to 10 g (preferably 1 mg to 2 g) for an oral formulation, 0.01 mg to 10 g (preferably 0.1 mg to 2 g) for an external preparation and 0.01 mg to 10 g (preferably 0.1 mg to 2 g) for an injection, either at once or divided into 2 to 4 doses.

The crystals of the invention are useful as anti-tumor agents, angiogenesis inhibitors or inhibitors for cancer metastasis.

When crystals of the invention are used as an antitumor agent, the tumor may be a pancreatic cancer, a gastric cancer, a colorectal cancer, a breast cancer, a prostate cancer, a lung cancer, a renal cancer, a brain tumor, an ovarian cancer or an esophageal cancer, with a gastric cancer or an esophageal cancer being the preferred target.

EXAMPLES

The salts of compounds according to the invention or crystals thereof may be prepared by the methods described by the following production examples and examples. However, these specific examples are merely illustrative and the compounds of the invention are in no way restricted by these specific examples.

Throughout the production examples, unless otherwise specified, YMC SIL-60-400/230W was used as the silica gel for purification.

Production Example 1-1

Ethyl 4-chloropyridine-2-carboxylate

A mixture of 4-chloropyridine-2-carboxylic acid (39.4 g) and thionyl chloride (64 ml) was stirred and heated at 100° C. under a nitrogen atmosphere for 6 hours. The reaction mixture was cooled to room temperature. The mixture was concentrated under reduced pressure and azeotropically distilled with toluene. The residue was gradually added to ethanol being, stirred on ice. The reaction mixture was stirred at room temperature for 25.5 hours. The reaction mixture was then concentrated under reduced pressure. A saturated aqueous solution of sodium hydrogencarbonate was added to the residue and the mixture was extracted with ethyl acetate. The organic layer was washed with brine and dried over anhydrous sodium sulfate. The dried organic layer was concentrated under reduced pressure to give the title compound as a brown oil (38.8 g, 83.6%).

$^1$H-NMR Spectrum (CDCl$_3$) δ (ppm): 1.46 (3H, t, J=7.2 Hz), 4.50 (2H, q, J=7.2 Hz), 7.49 (1H, dd, J=2.0, 5.2 Hz), 8.15 (1H, d, J=2.0 Hz), 8.67 (1H, d, J=5.2 Hz).

Production Example 1-2

Ethyl 4-(3-fluoro-4-nitrophenoxy)pyridine-2-carboxylate

To ethyl 4-chloropyridine-2-carboxylate (19.4 g) were added 3-fluoro-4-nitrophenol (24.7 g) and chlorobenzene (7.0 ml), and the % mixture was stirred and heated at 120° C. under a nitrogen atmosphere for 4 hours. The reaction mixture was cooled to room temperature. After adding ethyl acetate (400 ml) and a saturated aqueous solution of sodium carbonate (400 ml), the mixture was further stirred at room temperature for 27 hours. Stirring was suspended and the aqueous layer was separated off. A saturated aqueous solution of sodium carbonate was further added to the organic layer and the mixture was, stirred at room temperature for 2 days. Stirring was suspended, and the aqueous layer was separated off. The aqueous layer was extracted with ethyl acetate (300 ml). The organic layers were combined and washed with brine. The organic layer was dried over anhydrous sodium sulfate and concentrated under reduced pressure. The residue was purified by silica gel column chromatography (eluent: heptane:ethyl acetate=2:1 to 1:1, then ethyl acetate). The fractions containing the target compound were concentrated to give the title compound as a brown oil (12.9 g, 40.2%).

$^1$H-NMR Spectrum (CDCl$_3$) δ (ppm): 1.45 (3H, t, J=7.2 Hz), 4.49 (2H, q, J=7.2 Hz), 6.97-7.01 (2H, m), 7.16 (1H, dd, J=2.4, 5.6 Hz), 7.79 (1H, d, J=2.4 Hz), 8.20 (1H, m), 8.716 (1H, d, J=5.6 Hz).

ESI-MS (m/z): 329 [M+Na]$^+$.

Production Example 1-3

4-(4-Benzyloxycarbonylamino-3-fluorophenoxy) pyridine-2-carboxylic acid

To a solution of ethyl 4-(3-fluoro-4-nitrophenoxy)pyridine-2-carboxylate (8.56 g) in ethanol (150 ml) was added 20% palladium hydroxide on carbon (1.0 g), and the reaction mixture was stirred for 9.5 hours at room temperature under a hydrogen atmosphere. The catalyst was removed by filtration. After adding a 4N solution of hydrochloric acid in ethyl acetate (14 ml) to the filtrate, the mixture Was concentrated. Concentrating was suspended before the mixture dried to dryness. Water (75 ml), acetone (150 ml) and sodium hydrogencarbonate (11.8 g) were then added. The mixture was stirred while cooling on ice and benzyloxycarbonyl chloride (6.00 ml) was added. The reaction mixture was stirred at room temperature for 4 hours. The mixture was then concentrated under reduced pressure, and the residue was extracted with ethyl acetate. The organic layer was washed with brine and dried over anhydrous sodium sulfate. It was then concentrated under reduced pressure and the residue was purified by silica gel column chromatography (eluent: heptane:ethyl acetate=1:1 to 1:2, then ethyl acetate). The fractions containing the target compound were concentrated under reduced pressure. The obtained solid was suspended by adding hexane. After allowing the suspension to stand for a while, the supernatant was removed with a pipette. The residue was dried to give ethyl 4-(4-benzyloxycarbonylamino-3-fluorophenoxy)pyridine-2-carboxylate as a pale yellow solid (7.51 g, 65.4%).

$^1$H-NMR Spectrum (CDCl$_3$) δ (ppm): 1.43 (3H, m), 4.45-4.52 (2H, m), 5.24 (2H, s), 6.87-6.92 (2H, m), 6.99 (1H, dd, J=2.4, 5.6 Hz), 7.35-7.45 (6H, m), 7.65 (1H, d, J=2.4 Hz), 8.19 (1H, m), 8.60 (1H, d, J=5.6 Hz).

Ethyl 4-(4-benzyloxycarbonylamino-3-fluorophenyl)pyridine-2-carboxylate (7.95 g) was dissolved in ethanol (120 ml), and water (25 ml) was added. Lithium hydroxide (783 mg) was added while stirring at room temperature, and stirring was continued at room temperature for 1 hour. After adding 1N hydrochloric acid (60 ml) to the reaction mixture, it was concentrated under reduced pressure. After concentration, the precipitated crystals in the reaction mixture were collected by filtration and washed with water. The crystals were dissolved in ethyl acetate-tetrahydrofuran and dried over anhydrous sodium sulfate. The dried solution was concentrated under reduced pressure. The obtained crystals were suspended in hexane and collected by filtration. The crystals were dried to give the target compound as pale yellow crystals (5.04 g, 72.0%).

$^1$H-NMR Spectrum (DMSO-d$_6$) δ (ppm): 5.18 (2H, s), 7.08 (1H, m), 7.23 (1H, m), 7.24-7.46 (8H, m), 7.75 (1H, m), 8.59 (1H, d, J=5.6 Hz), 9.59 (1H, s).

Production Example 1-4 tert-Butyl [4-(4-benzyloxycarbonylamino-3-fluorophenoxy)pyridin-2-yl]carbamate

To a suspension of 4-(4-benzyloxycarbonylamino-3-fluorophenoxy)pyridine-2-carboxylic acid (5.04 g) in tert-butanol (50 ml) was added triethylamine (4.6 ml) at room temperature, and the mixture was stirred. Diphenylphosphoryl azide (3.13 ml) was then added at room temperature and stirring was continued for 30 minutes at room temperature under a nitrogen atmosphere. Heated stirring was then carried out at 90° C. for 30 minutes and at 100° C. for 4 hours. The reaction mixture was cooled to room temperature. Ethyl acetate (25 ml) was added, and the reaction mixture was stirred for 30 minutes while cooling on ice. The precipitated crystals were collected by filtration and washed with diethyl ether. The crystals were then dried under aeration for 1 hour at room temperature to give the title compound as colorless crystals (3.92 g; 65.5%).

¹H-NMR Spectrum (DMSO-d₆) δ (ppm): 1.42 (9H, s), 5.17 (2H, s), 6.62 (1H, dd, J=2.4, 5.6 Hz), 7.01 (1H, dd, J=2.2, 8.8 Hz), 7.21 (1H, dd, J=2.2, 11.2 Hz), 7.35-7.42 (6H, m), 7.70 (1H, m), 8.14 (1H, d, J=5.6 Hz), 9.53 (1H, s), 9.83 (1H, s).

Production Example 1-5

Benzyl [4-(2-aminopyridin-4-yloxy)-2-fluorophenyl]carbamate

A 4N solution of hydrochloric acid in ethyl acetate solution (120 ml) was cooled in an ice bath. To this was added tert-butyl [4-(4-benzyloxycarbonylamino-3-fluorophenoxy)pyridin-2-yl]carbamate (3.92 g) while stirring and the mixture was further stirred for 10 minutes in an ice bath. The reaction mixture was then further stirred for 3.5 hours at room temperature. The reaction mixture was concentrated under reduced pressure. Ethyl acetate (150 ml) and a saturated aqueous solution of sodium hydrogencarbonate (70 ml) were then added and partitioned. The aqueous layer was extracted with ethyl acetate (50 ml). The combined organic layers were washed with brine and dried over anhydrous sodium sulfate. The dried organic layer was concentrated under reduced pressure. The obtained crystals were suspended in a mixed solvent of hexane and ethyl acetate (5:1). The crystals were collected by filtration and washed with a mixed solvent of hexane and ethyl acetate (5:1). The crystals were then suction-dried at room temperature to give the title compound as pale yellow crystals (2.93 g, 95.9%).
¹H-NMR Spectrum (CDCl₃) δ (ppm): 4.49 (2H, m), 5.23 (2H, s), 5.95 (1H, d, J=2.0 Hz), 6.26 (1H, dd, J=2.0, 6.0 Hz), 6.84-6.90 (2H, m), 7.00 (1H, m), 7.34-7.42 (5H, m), 7.94 (1H, d, J=6.0 Hz), 8.10 (1H, m).
ESI-MS (m/z): 354 [M+H]⁺.

Production Example 1-6

Phenyl N-[4-(3-fluoro-4-{[1-(4-fluorophenylcarbamoyl)cyclopropanecarbonyl]amino}phenoxy)pyridin-2-yl]-N-phenoxycarbonylcarbamate To a solution of benzyl [4-(2-aminopyridin-4-yloxy)-2-fluorophenyl]carbamate (1.25 g) in tetrahydrofuran (100 ml) were added triethylamine (1.48 ml) and phenyl chloroformate (1.11 ml), and the mixture was stirred at room temperature for 1 hour. The reaction mixture was partitioned between ethyl acetate and a 1N aqueous solution of sodium hydroxide. The organic layer was washed with brine and dried over anhydrous sodium sulfate. The solvent was distilled away to give a crude product of phenyl N-[4-(4-benzyloxycarbonylamino-3-fluorophenoxy)pyridin-2-yl]-N-phenoxycarbonylcarbamate as a brown oil (ESI-MS (m/z): 616 [M+Na]⁺). This was dissolved in tetrahydrofuran (200 ml), 20% palladium hydroxide (497 mg) was added, and the mixture was stirred at room temperature for 4 hours under a hydrogen atmosphere. The catalyst was removed by filtration. It was subsequently washed with tetrahydrofuran. The filtrate was concentrated to 20 ml to give a solution of phenyl N-[4-(4-amino-3-fluorophenoxy)pyridin-2-yl]-N-phenoxycarbonylcarbamate (ESI-MS (m/z): 482 [M+Na]⁺, 941 [2M+Na]⁺) in tetrahydrofuran. This was dissolved in N,N-dimethylformamide (50 ml). After then adding 1-(4-fluorophenylcarbamoyl)cyclopropanecarboxylic acid (1.58 g), benzotriazol-1-yloxytris(dimethylamino)phosphonium hexafluorophosphate (3.13 g) and triethylamine (0.987 ml), the mixture was stirred at room temperature for 13.5 hours. The reaction mixture was partitioned between ethyl acetate and brine. The organic layer was washed with a 1N aqueous solution of sodium hydroxide and brine in that order and dried over anhydrous sodium sulfate. It was then concentrated and the residue was purified by silica gel column chromatography (heptane:ethyl acetate=3:2, 1:1 and 1:2) to give the title compound as a colorless foam (940 mg, 40.0%).
¹H-NMR Spectrum (CDCl₃) δ (ppm): 1.68-1.76 (4H, m), 6.90 (1H, dd, J=2.4, 5.6 Hz), 6.95 (1H, m), 6.98 (1H, m), 7.03-7.07 (3H, m), 7.18 (4H, d, J=8.4 Hz), 7.25 (2H, m), 7.38 (4H, m), 7.48 (2H, m), 8.27 (1H, m), 8.46 (1H, d, J=5.6 Hz), 8.75 (1H, s), 9.40 (1H, s).
ESI-MS (m/z): 687 [M+Na]⁺.

Production Example 1

N-(2-Fluoro-4-{[2-{[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (Compound 1)

To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added 1-methyl-4-(piperidin-4-yl)piperazine (68.7 mg) and the mixture was stirred at room temperature for 12 hours. The reaction mixture was partitioned between ethyl acetate and a 1N aqueous solution of sodium hydroxide. The organic layer was washed with brine and dried over anhydrous sodium sulfate. The solvent was distilled off and the residue was purified by silica gel column chromatography (FUJI SILYSIA NH, ethyl acetate, ethyl acetate:methanol=20:1 to 10:1). The fractions containing the target compound were concentrated. Diethyl ether:hexane =1:3 was added to the residue and the deposited precipitate was collected by filtration. It was then washed with hexane and dried under aeration to give the title compound as white powder (34.6 mg, 72.8%).
¹H-NMR Spectrum (CDCl₃) δ (ppm): 1.44 (2H, m), 1.68 (2H, m), 1.75 (2H, m), 1.90 (2H, m), 2.32 (3H, s), 2.39-2.71 (9H, m), 2.906 (2H, m), 4.11 (2H, m), 6.55 (1H, dd, J=2.0, 5.6 Hz), 6.92 (2H, m), 7.04 (2H, m), 7.26 (1H, covered by CDCl₃), 7.50 (2H, dd, J=4.8, 9.2 Hz), 7.62 (1H, d, J=2.0 Hz), 8.06 (1H, d, J=5.6 Hz), 8.20 (1H, m), 8.84 (1H, s), 9.20 (1H, s).
ESI-MS (m/z): 634 [M+H]⁺, 656 [M+Na]⁺.

Production Example 1'-1

1-(Benzyloxycarbonyl)cyclopropanecarboxylic acid (Method 1)
1,1-Cyclopropanedicarboxylic acid (5.02 g) was dissolved in tetrahydrofuran (50 ml) under a nitrogen atmosphere, and triethylamine (5.38 ml) was added dropwise with stirring and cooling in an ice water bath. After stirring at the same temperature for 30 minutes, thionyl chloride (2.82 ml) was added dropwise with cooling in ice water bath. After stirring at the same temperature for 30 minutes, a solution of benzyl alcohol (4.39 ml) in tetrahydrofuran (25 ml) was added with cooling in an ice water bath, and the reaction mixture was gradually brought to room temperature and stirred overnight. A 2N aqueous solution of sodium hydroxide (100 ml) was added to the reaction mixture, and tetrahydrofuran was distilled off under reduced pressure. tert-Butyl methyl ether (25 ml) was added to the resultant aqueous solution, followed by stirring.

The organic layer and the aqueous layer were separated. The aqueous layer was cooled in an ice water bath, and 2N hydrochloric acid (50 ml) was added to adjust pH 4. Ethyl acetate (150 ml) was added, and the reaction mixture was stirred for a while. The organic layer was separated, washed with brine, and dried over anhydrous sodium sulfate. The residue obtained by distilling off the solvent was dried under reduced pressure to give the title compound (6.29 g, 74%) as a pale yellow oil.

$^1$H-NMR Spectrum (DMSO-$d_6$) δ (ppm): 1.30-1.40 (4H, m), 5.15 (2H, s), 7.30-7.38 (5H, m).

ESI-MS (m/z): 243 [M+Na]$^+$.

(Method 2)

1,1-Cyclopropanedicarboxylic acid (50 g) was dissolved in acetonitrile (500 ml) under a nitrogen atmosphere, and N-methylimidazole (31 ml) was added dropwise with stirring and cooling in an ice water bath. After stirring at the same temperature for 30 minutes, thionyl chloride (29 ml) was added dropwise. After stirring at the same temperature for 30 minutes, a mixed solution of benzyl alcohol (45.7 g) and N-methylimidazole (31 ml) was added with cooling in an ice water bath, and the reaction mixture was stirred at the same temperature for 6 hours. A 2N aqueous solution of sodium hydroxide (900 ml) was added to adjust pH 8. tert-Butyl methyl ether (500 ml) was added to the resultant solution, and the mixture was stirred. The organic layer and the aqueous layer were separated, and the organic layer was extracted with a 5% aqueous solution of sodium hydrogencarbonate (200 ml). The aqueous layers were combined, cooled in an ice water bath, and 5N hydrochloric acid (300 ml) was added to adjust pH 4. Ethyl acetate (1000 ml) was added, and the mixture was stirred for a while. The organic layer was separated, washed with brine, and dried over anhydrous sodium sulfate. The residue obtained by distilling off the solvent was dissolved in methanol (120 ml), and water (120 ml) was added dropwise with stirring at room temperature. After stirring at room temperature for 30 minutes, and with cooling in an ice water bath for 2 hours, the precipitated solid was suction filtered, and washed with water (60 ml, twice). The resultant solid was dried under reduced pressure at 40° C. to give the title compound (59 g, 69%).

Production Example
1'-2)4-(4-Amino-3-fluorophenoxy)pyridine

-2-carboxamide (Method 1)

4-Amino-3-fluorophenol (5.7 g) was dissolved in dimethyl sulfoxide (57 ml) under a nitrogen stream, potassium tert-butoxide (5.6 g) was added at room temperature, and the reaction mixture was stirred for 15 minutes. 4-Chloropyridine-2-carboxamide (5.0 g) was added to the reaction mixture, followed by stirring in an oil bath at 80° C. (external temperature) under a nitrogen stream for 50 minutes. The reaction mixture was allowed to cool down to room temperature. A 1N aqueous solution of sodium hydroxide (85.5 ml) was added to the reaction mixture, followed by stirring. The precipitated solid was collected by filtration and washed with water. The residue was dried under aeration and then dried by hot air at 100° C. to give the title compound (5.88 g, 74.3%) as pale brown powder.

$^1$H-NMR Spectrum (DMSO-$d_6$) δ (ppm): 5.18-5.30 (2H, m), 6.80 (1H, dd, J=2.4, 8.4 Hz), 6.81-6.90 (1H, m), 7.02 (1H, dd, J=2.4, 11.6 Hz), 6.99-7.14 (1H, m), 7.32-7.39 (1H, m), 7.69 (1H, brs), 8.10 (1H, brs), 8.48 (1H, m).

(Method 2)

Potassium tert-butoxide (214 g) was dissolved in dimethyl sulfoxide (750 ml) and tetrahydrofuran (250 ml) under a nitrogen stream, and a solution of 4-amino-3-fluorophenol ½ naphthalene-2,6-disulfonate (242 g) and 4-chloropyridine-2-carboxamide (100 g) in dimethyl sulfoxide (1000 ml) was added dropwise to the solution with stirring and cooling on ice. The reaction mixture was stirred at room temperature for 30 minutes, then in an oil bath at 90° C. (external temperature) for 2 hours. The reaction mixture was allowed to cool down to room temperature, and water (3000 ml) was added, and the reaction mixture was stirred for 2 hours. The precipitated solid was collected by filtration, and washed with water (500 ml, twice). The residue was suspended in water (2000 ml), stirred for 30 minutes, collected by filtration again, and washed with water (500 ml, twice). Drying by hot air at 60° C. gave the title compound (119 g, 75.3%).

Production Example 1'-3)1-[4-(2-Carbamoylpyridin-4-yloxy)-2

-fluorophenylcarbamoyl]cyclopropanecarboxylic acid benzyl ester (Method 1)

A mixture of 1-(benzyloxycarbonyl)cyclopropanecarboxylic acid (11.5 g), tetrahydrofuran (148 ml) and N-methylmorpholine (10.9 g) was stirred with cooling on ice. Thionyl chloride (6.19 g) was added dropwise at the internal temperature between 4.4° C. and 25.2° C., and the reaction mixture was stirred for 47 minutes. 4-(4-Amino-3-fluorophenoxy)pyridine-2-carboxamide (9.89 g) was added over 2 minutes at the internal temperature between 1.9° C. and 13.4° C., and the reaction mixture was stirred for 4 hours and 40 minutes with keeping the internal temperature between 3° C. and 6° C. The reaction mixture was partitioned after the addition of ethyl acetate (346 ml), a 2N aqueous solution of sodium hydroxide (100 ml), tetrahydrofuran (49 ml) and water (20 ml). The organic layer was washed twice with a 5% aqueous solution of sodium chloride (49 ml). The organic layer was concentrated under reduced pressure, and the precipitated crystals were triturated with a mixed solvent of ethyl acetate (15 ml) and heptane (15 ml). This was filtered and washed with a mixed solvent of ethyl acetate (5 ml) and heptane (5 ml) to give the title compound (13.44 g).

$^1$H-NMR Spectrum (DMSO-$d_6$) δ (ppm): 1.58 (4H, s), 5.20 (2H, s), 7.06-7.11 (1H, m), 7.19-7.23 (1H, m), 7.31-7.44 (7H, m), 7.72 (1H, s), 8.13 (1H, s), 8.51-8.56 (1H, m), 8.75 (1H, t, J=8.4 Hz), 10.71 (1H, s).

(Method 2)

N-Methylmorpholine (12.8 g) was added to a solution of 2-chloro-4,6-dimethoxy-1,3,5-triazine (24.5 g) in tetrahydrofuran (625 ml) with stirring at room temperature, at the internal temperature between 25.0° C. and 27.5° C. After stirring at room temperature for 50 minutes, 1-(benzyloxycarbonyl)cyclopropanecarboxylic acid (24.5 g) was added at the same temperature. After 10 minutes, 4-(4-amino-3-fluorophenoxy)pyridine-2-carboxamide (25.5 g) was added with stirring at room temperature. The reaction mixture was stirred at room temperature for 12 hours and 50 minutes. A 5% aqueous solution of sodium hydrogencarbonate (1250 ml) was added to the reaction mixture, followed by stirring at room temperature for 3 hours. The mixture was filtered, and the collected crystals were washed with water (100 ml). The crystals were dried at 60° C. for 13 hours to give the target title compound (45.4 g).

Production Example 1'-4) 1-[4-(2-Aminopyridin-4-yloxy)-2-fluorophenylcarbamoyl]cyclopropanecarboxylic acid benzyl ester (Method 1)

1-[4-(2-Carbamoylpyridin-4-yloxy)-2-fluorophenylcarbamoyl]-cyclopropanecarboxylic acid benzyl ester (2 g) was dissolved in N,N-dimethylformamide (20 ml) at room temperature, and water (0.481 ml) was added. Iodobenzene diacetate (2.87 g) was added at room temperature with stirring, and the reaction mixture was stirred for 2.5 hours. Water (40 ml) was added to the reaction mixture, and the reaction was quenched by the addition of a 2N aqueous solution of sodium hydroxide until pH became 11, and ethyl acetate was added and the layers were separated. The organic layer was washed with water and a 5% aqueous solution of sodium chloride, dried over magnesium sulfate, filtered, and concentrated. The resultant crude brown oil was purified by silica gel column chromatography (eluent; heptane:ethyl acetate=1:1, to 1:2) to give the title compound (819 mg) as cream crystals.

$^1$H-NMR Spectrum (DMSO-$d_6$) δ (ppm): 1.50-1.60 (4H, brs), 3.30 (2H, s), 5.19 (2H, s), 5.85 (1H, d, J=2.4 Hz), 5.96 (1H, m), 6.15 (1H, dd, J=2.4 Hz, 6.4 Hz), 6.96 (1H, m), 7.20 (1H, dd, J=2.4 Hz, 11.2 Hz), 7.30-7.42 (4H, m), 7.81 (1H, d, J=5.6 Hz), 7.96 (1H, m), 10.62 (1H, s).

(Method 2)

1-[4-(2-Carbamoylpyridin-4-yloxy)-2-fluorophenylcarbamoyl]cyclopropanecarboxylic acid benzyl ester (10 g) was dissolved in N,N-dimethylformamide (100 ml) at room temperature, and water (2.41 ml) was added. Iodobenzene diacetate (7.91 g) was added with stirring at room temperature, the reaction mixture was stirred for 3 hours, iodobenzene diacetate (360 mg) was further added, and the reaction mixture was stirred for 2 hours. Ethyl acetate (100 ml) and a 5% aqueous solution of sodium hydrogencarbonate (100 g) were added to the reaction mixture, and layers were separated. The organic layer was washed with water, dried over magnesium sulfate, filtered, and concentrated. Ethyl acetate (30 ml) was added to the resultant crude crystals, and the mixture was heated and stirred at 60° C. After confirming the crystals were dissolved, the mixture was allowed to cool down to room temperature. Seed crystals obtained in Method 1 (50 mg) were added, and the mixture was stirred for 30 minutes. After confirming the precipitation of the crystals, heptane (100 ml) was added, and the mixture was further stirred for 30 minutes. The crystals were collected by filtration and dried to give the title compound (6.84 g).

(Method 3)

1-[4-(2-Carbamoylpyridin-4-yloxy)-2-fluorophenylcarbamoyl]cyclopropanecarboxylic acid benzyl ester (17.9 g) was dissolved in N-methyl-2-pyrrolidone (125 ml) at room temperature, and water (7.2 ml) was added. Iodobenzene diacetate (14.1 g) was added with stirring at room temperature, followed by stirring for 4 hours and 7 minutes. Ethyl acetate (268 ml) and a 1N aqueous solution of sodium hydroxide (179 ml) were added to the reaction mixture, and the layers were separated. The organic layer was washed with a 5% aqueous solution of sodium chloride (179 ml) three times and water (179 ml) once, dried over magnesium sulfate, filtered, and concentrated. Toluene (72 ml) was added to the resultant crystals, and the mixture was heated and stirred at 90° C. After confirming the crystals were dissolved, the mixture was allowed to cool down to room temperature. The precipitated crystals were collected by filtration, washed with toluene (18 ml), and dried under reduced pressure at 50° C. for 4 hours to give the title compound (11.9 g) as pale orange crystals.

Production Example 1'-5) 1-[2-Fluoro-4-(2-phenoxycarbonylaminopyridin-4-yloxy)phenylcarbamoyl]cyclopropanecarboxylic acid benzyl ester Tetrahydrofuran (41 ml), acetonitrile (41 ml) and pyridine (2.07 g) was added to 1-[4-(2-aminopyridin-4-yloxy)-2-fluorophenylcarbamoyl]cyclopropanecarboxylic acid benzyl ester (6.0 g, content 5.51 g), which was dissolved by stirring. Phenyl chloroformate (4.1 g) was added dropwise to this solution with cooling on ice at the internal temperature between 8.8° C. and 14.9° C. The reaction mixture was stirred at the same temperature for 2 hours and 9 minutes, then at room temperature for 3 hours and 5 minutes. The precipitate was collected by filtration, washed with a mixed solvent of tetrahydrofuran and acetonitrile (2:1, 16 ml), and dried under aeration to give the target title compound (6.39 g).

Production Example 1'-6) 1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester (Method 1)

Potassium carbonate (772 mg) was added to a mixture of 1-[2-fluoro-4-(2-phenoxycarbonylaminopyridin-4-yloxy)phenylcarbamoyl]cyclopropanecarboxylic acid benzyl ester (2.75 g) and N,N-dimethylformamide (13.8 ml) was added, followed by stirring. 1-Methyl-4-(piperidin-4-yl)piperazine (1.02 g) was added, followed by stirring for 6 hours. The reaction mixture was partitioned after the addition of ethyl acetate (41 ml) and water (27.5 ml). The resultant organic layer was washed with water (13.8 ml, three times), dried over sodium sulfate, and filtered, and the filtrate was concentrated. The resultant residue was purified by silica gel column chromatography (Fuji Silysia NH, eluent; ethyl acetate:methanol=30:1). The eluate was concentrated under reduced pressure, and the precipitate appeared by the addition of tert-butyl methyl ether (3 ml) and the application of a stimulus. tert-Butyl methyl ether (40 ml) was further added, followed by stirring overnight. The resultant precipitate was collected by filtration, washed with tert-butyl methyl ether (3 ml), and dried under aeration to give the target title compound (1.61 g).

$^1$H-NMR Spectrum (DMSO-$d_6$) δ (ppm): 1.20-1.34 (2H, m), 1.57 (4H, s), 1.72 (2H, d, J=10.8 Hz), 2.12 (3H, s), 2.18-2.40 (4H, m), 2.45 (3H, brs), 2.74 (2H, t, J=11.6 Hz), 3.30 (2H, s), 4.10 (2H, d, J=13.6 Hz), 5.20 (2H, s), 6.43-6.55 (1H, m), 6.97-7.10 (1H, m), 7.22-7.29 (1H, m), 7.30-7.44 (6H, m), 7.98-8.08 (1H, m), 8.13 (1H, d, J=6.0 Hz), 9.21 (1H, s), 10.67 (1H, s).

(Method 2)

1-Methyl-4-(piperidin-4-yl)piperazine (1.46 g) was added to a mixture of 1-[2-fluoro-4-(2-phenoxycarbonylaminopyridin-4-yloxy)phenylcarbamoyl]cyclopropanecarboxylic acid benzyl ester (3.60 g) and N-methyl-2-pyrrolidone (25 ml), followed by stirring with heating at 40° C. for 1 hour and 51 minutes. The reaction mixture was partitioned after the addition of ethyl acetate (180 mL) and water (90 mL). The resultant organic layer was washed with water (36 ml, twice) and a 10% aqueous solution of sodium chloride (36 ml), dried over anhydrous magnesium sulfate (10 g), and filtered, and the filtrate was concentrated. The resultant residue was purified by silica gel column chromatography (Fuji Silysia NH, eluent; heptane:ethyl acetate=1:1, ethyl acetate, ethyl acetate: isopropyl alcohol=9:1). The eluate was concentrated under reduced pressure, and the precipitate appeared after the addition of tert-butyl methyl ether (60 ml) and seed crystals obtained in (Method 1). The resultant precipitate was collected by filtration, washed with tert-butyl methyl ether (10 ml), and dried under reduced pressure at 40° C. for 2 hours to give the target title compound (2.57 g).

Production Example 1'-7)1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester trihydrochloride (Method 1)
1-[2-Fluoro-4-(2-{[4-(4-methylpiperazin-1-yl)piperidine-1-carbonyl]amino}piperidin-4-yloxy)phenylcarbamoyl]cyclopropanecarboxylic acid benzyl ester (189 mg) was dissolved in ethyl acetate (6 ml), and 4N hydrochloric acid in ethyl acetate (0.3 ml) was added. The resultant mixture was concentrated under reduced pressure, and methanol (0.5 ml) and ethyl acetate (4 ml) was added. The precipitate obtained by filtration was hygroscopic, thus it was collected using methanol (10 ml). The collected solution was again concentrated under reduced pressure, and methanol (0.5 ml) and tert-butyl methyl ether (4 ml) was added. The precipitate was filtered to give the title compound (102 mg).
$^1$H-NMR Spectrum (DMSO-$d_6$) δ (ppm): 1.58 (4H, s), 1.60-1.74 (2H, m), 2.17 (2H, d, J=10.4 Hz), 2.83 (3H, s), 2.91 (2H, t, J=12.4 Hz), 3.50-3.57 (9H, m), 4.39 (2H, d, J=12.8 Hz), 5.20 (2H, s), 7.03-7.09 (1H, m), 7.13-7.19 (1H, m), 7.30-7.42 (6H, m), 7.46 (1H, dd, J=2.4, 8.8 Hz), 8.14 (1H, t, J=8.8 Hz), 8.30 (1H, d, J=7.2 Hz), 10.78 (1H, s), 10.93 (1H, brs).
(Method 2)
1-Methyl-4-(piperidin-4-yl)piperazine (812 mg) was added to a mixture of 1-[2-fluoro-4-(2-phenoxycarbonylaminopyridin-4-yloxy)phenylcarbamoyl]cyclopropanecarboxylic acid benzyl ester (2.0 g) and N-methyl-2-pyrrolidone (14 ml), followed by stirring at 40° C. for 2 hours and 31 minutes. The reaction mixture was partitioned after the addition of ethyl acetate (60 ml) and water (40 ml). The organic layer was washed with a 5% aqueous solution of sodium chloride (10 ml, three times) and water (10 ml). 4N Hydrochloric acid in ethyl acetate (0.5 ml) was added to a portion (10 ml) of the resultant organic layer, and seed crystals obtained in (Method 1) were added. Isopropyl alcohol (1 ml) was added, and the precipitate appeared after sonication. The resultant precipitate was filtered, and washed with ethyl acetate (2 ml) to give the title compound (322 mg).
(Method 3)
1-Methyl-4-(piperidin-4-yl)piperazine (2.68 g) was added to a mixture of 1-[2-fluoro-4-(2-phenoxycarbonylaminopyridin-4-yloxy)phenylcarbamoyl]cyclopropanecarboxylic acid benzyl ester (6.63 g) and N-methyl-2-pyrrolidone (33 ml), followed by stirring at 40° C. for 2 hours and 10 minutes. The reaction mixture was partitioned after the addition of ethyl acetate (132 ml) and water (99 ml). The organic layer was washed with a 5% aqueous solution of sodium chloride (33 ml, twice) and water (33 ml). 4N hydrochloric acid in ethyl acetate (10 ml) was added to isopropyl alcohol (13 ml), then the above washed organic layer (8 ml) was added dropwise thereto, the seed crystals obtained in (Method 2) was added, and the organic layer was father added dropwise. During the addition, isopropyl, alcohol (13 ml) was added, and the mixture was treated with sonication, and the drop continued. After the completion of the addition, the mixture was stirred for 5 hours and 38 minutes. The precipitate was filtered, washed with a mixed solvent of ethyl acetate and isopropyl alcohol (5:1, 20 ml), and the solvent was replaced by ethyl acetate (20 ml). Drying under aeration under a nitrogen stream and drying under reduced pressure at 40° C. for 2 hours gave the target title compound (6.12 g).
(Method 4)
A solution of 1-methyl-4-(piperidin-4-yl)piperazine in N-methyl-2-pyrrolidone (24.8%, 26.3 g) was added to a mixture of 1-[2-fluoro-4-(2-phenoxycarbonylaminopyridin-4-yloxy)phenylcarbamoyl]cyclopropanecarboxylic acid benzyl ester (16.1 g) and N-methyl-2-pyrrolidone (46 ml), washing with N-methyl-2-pyrrolidone (15 ml) was performed. The mixture was stirred at 37° C. for 1 hour and 52 minutes. The reaction mixture was partitioned after the addition of ethyl acetate (242 ml) and water (242 ml). The organic layer was washed with 1N hydrochloric acid (81 ml). The aqueous layer was separated, ethyl acetate (161 ml) was added, and a 2N aqueous solution of sodium hydroxide (81 mL) was added, and the partition was performed. The organic layer was separated and washed with a 1% aqueous solution of sodium chloride (81 g), and the organic layer (151.3 g) was collected. A portion (104.2 g) of the above organic layer was added to ethanol (48 ml), and concentrated hydrochloric acid (7.41 ml) was added to the mixture with stirring on ice. A portion (ca. 15 ml) of the rest of the organic layer was added and seed crystals (48.3 mg) were added, and the mixture was stirred at room temperature for 1 hour and 14 minutes. The whole amount of the rest of the organic layer was added dropwise over 29 minutes, followed by stirring for 16 hours and 19 minutes. The precipitate was collected by filtration, washed with a mixed solvent of ethyl acetate and ethanol (3:1, 32.4 ml), and the solvent was replaced by ethyl acetate (32.2 ml). Drying under aeration under a nitrogen stream and drying under reduced pressure at 40° C. for 2 hours and 20 minutes gave the title compound (15.0 g).

Production Example 1'-8-1)1-[2-Fluoro-4-(2-{[4-(4-methylpiperazin-1-yl)piperidine-1-carbonyl]amino}pyridin-4-yloxy)phenylcarbamoyl]cyclopropanecarboxylic acid (Method 1)
1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester (800 mg) was dissolved in a mixed solvent of tetrahydrofuran (4 ml) and ethanol (4 ml), palladium on carbon (400 mg) was added, and the mixture was stirred at room temperature under a hydrogen atmosphere (0.15 MPa) for 4 hours. Water (4 ml) was added to the reaction mixture, which was filtered, and the residue was washed with a 50% aqueous ethanol (8 ml) and water (4 ml), and the filtrate was concentrated. Tetrahydrofuran (8 ml) and ethanol (8 ml) was added to the residue, which was concentrated. Tetrahydrofuran (8 ml), ethyl acetate (8 ml) and ethanol (2 ml) were added to the residue, which was concentrated. Tetrahydrofuran (8 ml) and ethanol (16 ml) were added to the residue, which was concentrated to precipitate crystals. The crystals were suspended in tetrahydrofuran (16 ml), stirred at room temperature for 40 minutes, filtered, and dried to give the title compound (550 mg) as white crystals.
$^1$H-NMR Spectrum (DMSO-$d_6$) δ (ppm): 1.1.5-1.23 (2H, m), 1.24-1.38 (4H, m), 1.70-1.80 (2H, m). 2.41-2.50 (2H, brs), 2.50 (3H, s), 2.60-2.90 (9H, m), 4.10-4.18 (2H, m), 6.60 (1H, dd, J=2.4 Hz, 5.6 Hz), 6.93 (1H, d, J=8.8 Hz), 7.17 (1H, dd, J=2.4 Hz, 11.6 Hz), 7.33 (1H, d, J=2.4 Hz), 8.10 (1H, d, J=5.6 Hz), 8.35 (1H, t, J=8.8 Hz), 9.21 (1H, s).

(Method 2)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester (500 mg) was dissolved in a mixed solvent of tetrahydrofuran (2.5 ml), ethanol (2.5 ml) and water (1.5 ml), palladium on carbon (100 mg) was added, and the mixture was stirred at room temperature under a hydrogen atmosphere (0.15 MPa) for 3 hours. The reaction mixture was filtered, and the residue was washed with a 90% aqueous ethanol (1 ml), and the filtrate was concentrated. Addition of ethanol to the residue and subsequent concentration were repeated three times. Ethanol (2.5 ml), tetrahydrofuran (2.5 ml) and the seed crystals obtained in (Method 1) were added to the residue, and the mixture was stirred at room temperature for 1 hour. Ethyl acetate (5 ml) was added, and the mixture was further stirred for 1 hour. The crystals were filtered and dried to give the title compound (420 mg) as white crystals.

(Method 3)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester hydrochloride (2 g) was dissolved in water (20 ml) and ethyl acetate (20 ml), and a 2N aqueous solution of sodium hydroxide (4 ml) was added, and the layers were separated. The organic layer was washed with water and concentrated. Addition of tetrahydrofuran and subsequent concentration was repeated three times. The residue was dissolved in a mixed solvent of tetrahydrofuran (8 ml) and water (1.6 ml), and palladium on carbon (200 mg) was added, and the mixture was stirred at room temperature under a hydrogen atmosphere (0.2 MPa) for 5 hours. Tetrahydrofuran (4 ml) and methanol (6 ml) were added to the reaction mixture, which was filtered. The residue was washed with 90% aqueous methanol (3 ml). Tetrahydrofuran (12 ml) and the seed crystals obtained in (Method 1) were added to the filtrate, and the mixture was stirred at room temperature for 1 hour. Ethyl acetate (32 ml) was added, and the mixture was stirred for 14 hours. The crystals were filtered and dried to give the title compound (1.2 g) as white crystals.

Production Example 1'-8-2)1-[2-Fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride (Method 1)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester trihydrochloride (2 g) was dissolved in a mixed solvent of water (4 ml) and ethanol (8 ml), palladium on carbon (100 mg) was added, and the mixture was stirred at room temperature under a hydrogen atmosphere (ca. 1 atmospheric pressure) for 5 hours and 10 minutes. The reaction mixture was filtered, and the residue was washed with a mixed solvent of water (1 ml) and ethanol (2 ml). Ethanol (20 ml) was added to the filtrate, which was concentrated. Addition of ethanol (10 ml) to the residue and subsequent concentrate were repeated four times. The mixture was filtered with heating and ethyl acetate (40 ml) was added dropwise with stirring at the same time. After stirring at room temperature for 25 hours and 30 minutes, the crystals were filtered with washing with a mixed solvent of ethanol (2 ml) and ethyl acetate (2 ml) and dried to give the title compound (1.56 g) as a white solid.

$^1$H-NMR Spectrum (DMSO-$d_6$) δ (ppm): 1.50-1.78 (8H, m), 2.04-2.22 (2H, m), 2.46 (3H, s), 2.80-3.90 (9H, m), 4.22-4.40 (2H, m), 7.01 (1H, brs), 7.13 (1H, d, J=9.6 Hz), 7.22 (1H, s), 7.43 (1H, d, J=12.4 Hz), 8.22-8.32 (2H, m), 11.30 (1H, s).

(Method 2)

1-[2-Fluoro-4-(2-{[4-(4-methylpiperazin-1-yl)piperidine-1-carbonyl]amino}pyridin-4-yloxy)phenylcarbamoyl]cyclopropanecarboxylic acid benzyl ester trihydrochloride (5 g) was dissolved in a mixed solvent of water (10 ml) and ethanol (20 ml), and palladium on carbon (250 mg) was added, and the mixture was stirred at room temperature under a hydrogen atmosphere (0.2 MPa) for 7 hours and 50 minutes. The reaction mixture was filtered, and the residue was washed with a mixed solvent of water (6 ml) and ethanol (10 ml). Ethanol (50 ml) was added to the filtrate, which was azeotropically distilled off and concentrated, and water (0.6 g) and ethanol (8.3 ml) were added. 2-Propanol (10 ml) was added to the solution, followed by stirring at room temperature for 5 minutes. 1-[2-Fluoro-4-(2-{[4-(4-methylpiperazin-1-yl)piperidine-1-carbonyl]amino}pyridin-4-yloxy)phenylcarbamoyl]cyclopropanecarboxylic acid trihydrochloride (150 mg) was added, followed by stirring for 13 hours and 45 minutes. 2-Propanol (50 ml) was further added, and the mixture was stirred at room temperature for 24 hours and 35 minutes. The crystals were filtered and dried to give the title compound (4.26 g) as a white solid.

Production Example 1')N-(2-Fluoro-4-{[2-{[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide (Compound 1)

(Method 1)

4-(4,6-Dimethoxy[1,3,5]triazin-2-yl)-4-methylmorpholinium chloride hydrate (164 mg) was added to a suspension of 1-[2-fluoro-4-(2-{[4-(4-methylpiperazin-1-yl)piperidine-1-carbonyl]amino}pyridin-4-yloxy)phenylcarbamoyl]cyclopropanecarboxylic acid (100 mg) in mixture of tetrahydrofuran (1 ml), N,N-dimethylformamide (0.2 ml) and 4-fluoroaniline (0.0526 ml), followed by stirring at room temperature for 2.5 hours. A 5% aqueous solution of sodium hydrogencarbonate was added to the reaction mixture to quench the reaction, and ethyl acetate was added and the layers were separated. The organic layer was washed with water and concentrated. The residue was purified by silica gel column chromatography (Fuji Silysia NH, eluent; ethyl acetate, ethyl acetate:methanol=95:5). The eluate was concentrated. Ethyl acetate (2 ml) was added to the resultant residue, followed by stirring at room temperature for 30 minutes. Heptane (2 ml) was added, and the mixture was stirred for 30 minutes. The crystals were collected by filtration and dried to give the title compound (74 mg) as white crystals.

$^1$H-NMR Spectrum (DMSO-$d_6$) δ (ppm): 1.22-1.33 (2H, m), 1.54-1.63 (4H, m), 1.68-1.78 (2H, m), 2.12 (3H, s), 2.12-2.40 (5H, m), 2.40-2.60 (4H, m), 2.68-2.78 (2H, m), 4.06-4.14 (2H, m), 6.60 (1H, dd, J=2.4 Hz, 5.6 Hz), 7.00 (1H, m), 7.19 (2H, t, J=8 Hz), 7.22 (1H, dd, J=2.4 Hz, 11.2 Hz), 7.40 (1H, s), 7.61 (2H, dd, J=5.2 Hz, 8 Hz), 7.93 (1H, t, J=8.8 Hz), 8.13 (1H, d, J=5.6 Hz), 9.21 (1H, s), 9.90 (1H, brs), 10.55 (1H, brs).

(Method 2)

4-(4,6-Dimethoxy[1,3,5]triazin-2-yl)-4-methylmorpholinium chloride hydrate (409 mg) was added to a suspension of 1-[2-fluoro-4-(2-{[4-(4-methylpiperazin-1-yl)-piperidine-1-carbonyl]-amino}-pyridin-4-yloxy)phenylcarbamoyl]-cyclopropanecarboxylic acid (500 mg, 0.925 mmol) in a mixture of tetrahydrofuran (4.5 ml), N,N-dimethylformamide (1 ml) and 4-fluoroaniline (0.131 ml), followed by stirring at room temperature for 16 hours. Ethyl acetate (7.5 ml) was added to the reaction mixture, and a 5% aqueous solution of sodium hydrogencarbonate (7.5 ml) was added to quench the reaction, and the layers were separated. 1N Hydrochloric acid (5 ml) was added to the organic layer, and the layers were separated. Tetrahydrofuran (7.5 ml) was added to the aqueous layer, and a 2N aqueous solution of sodium hydroxide (3 ml) was added to effect neutralization, and ethyl acetate (7.5 ml) was added and the layers were separated. The organic layer was washed with water and concentrated. Addition of ethyl acetate to the residue and subsequent concentration were repeated three times.

To the residue was added ethyl acetate until the whole weight reached to 2.34 g, and the seed crystals obtained in (Method 1) was added, and the mixture was stirred at room temperature for 30 minutes. Ethyl acetate (2.5 ml) was added, and the mixture was stirred for 1 hour, heptane (5 ml) was added and the mixture was stirred for 2 hours. The crystals were collected by filtration and dried to give the title compound (427 mg) as white crystals.
(Method 3)

N-Methylmorpholine (419 g) was added to a solution of 2-chloro-4,6-dimethoxy-1,3,5-triazine (238 g) in a mixture of tetrahydrofuran (4400 g) and 2-propanol (2159 g) with stirring, and tetrahydrofuran (122 g) was used for washing, and the mixture was stirred at 25° C. for 33 minutes. 1-[2-Fluoro-4-(2-{[4-(4-methylpiperazin-1-ly)piperidine-1-carbonyl] amino}piperidin -4-yloxy)phenylcarbamoyl]-cyclopropaneearboxylic acid trihydrochloride (550 g) was added to the reaction mixture, tetrahydrofuran (245 g) was used for washing, 4-fluoroaniline (132 g) was added, tetrahydrofuran (122 g) was used for washing, and the mixture was stirred at 25° C. for 4 hours and 20 minutes. Isopropyl acetate (7194 g) and a 1N aqueous solution of hydrochloric acid (5593 g) were added to the reaction mixture, and the layers were separated. Tetrahydrofuran (1147 g) and isopropyl acetate (7194 g) were added to the aqueous layer, a 2N aqueous solution of sodium hydroxide (5401 g) was added to effect neutralization, and the layers were separated. The organic layer was washed with a 5% aqueous solution of sodium chloride (1650 g) twice, and water (1650 g) once, and concentrated until the liquid volume became ca. 3 L. Isopropyl acetate (1440 g) was added to the concentrated solution, and the mixture was stirred at 25° C. for 1 hour and 20 minutes. Isopropyl acetate (959 g) was added, and the mixture was stirred at the same temperature for 3 hours and 7 minutes. Isopropyl acetate (2398 g) was added, and the mixture was stirred at the same temperature for 16 hours and 28 minutes. The precipitated crystals were collected by filtration and dried to give the title compound (408 g) as white crystals.

Example 1-1)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide hydrochloride After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (63.4 mg) in acetone (0.634 ml), 5N hydrochloric acid (0.020 ml) and water (0.0117 ml) were added at room temperature to form a solution. The solution was stirred overnight at room temperature. The precipitate was collected by filtration and washed with acetone (0.317 ml, 2 times). It was then dried under aeration at room temperature for 30 minutes, and then dried with warm air at 60° C. for 1 day to give the title compound (43.3 mg) as white powder.

$^1$H-NMR Spectrum (DMSO-$d_6$) δ (ppm): 1.40-1.80 (6H, m), 2.00-3.80 (16H, m), 4.20-4.40 (2H, m), 6.93 (1H, m), 7.12 (1H, m), 7.18 (2H, m), 7.25 (1H, m), 7.37 (1H, m), 7.59-7.63 (2H, m), 8.04 (1H, m), 8.13 (1H, d, J=6.4 Hz), 9.24 (1H, s), 9.91 (1H, brs), 10.76 (1H, brs).

Example 1-2)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide hydrobromide (Method 1)

After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (55.7 mg) in acetone (0.557 ml)-48% aqueous hydrobromic acid (0.010 ml) and water (0.0178 ml) were added at room temperature to form a solution. The solution was stirred overnight at room temperature. The precipitate was collected by filtration and washed with acetone (0.557 ml, 2 times). It was then dried under aeration at room temperature for 30 minutes, and then dried with warm air at 0.60° C. for 2 days to give the title compound (62.9 mg) as white powder.

(Method 2)

After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (55.7 mg) in water (1.67 ml), 48% aqueous hydrobromic acid (0.010 ml) was added at room temperature to form an aqueous solution. A dry ice/ethanol bath was used to freeze the aqueous solution, after which it was lyophilized under reduced pressure for 27 hours to give the title compound (70.7 mg) as white powder.

$^1$H-NMR Spectrum (DMSO-$d_6$) δ (ppm): 1.40-1.80 (6H, m), 2.00-3.80 (16H, m), 4.10-4.30 (2H, m), 7.02 (1H, m), 7.07 (1H, m), 7.10-7.20 (4H, m), 7.40 (1H, m), 7.58-7.62 (2H, m), 8.08 (1H, m), 8.26 (1H, d, J=6.4 Hz), 9.86 (1H, s), 10.81 (1H, brs).

Example 1-3)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide sulfate After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (31.7 mg) in ethanol (0.317 ml)-water (0.0058 ml), 2.5 M sulfuric acid (0.010 ml) was added at room temperature to form a solution. The solution was stirred overnight at room temperature. The precipitate was collected by filtration and washed with ethanol (0.158 ml, 2 times). It was then dried under aeration at room temperature for 30 minutes, and then dried with warm air at 60° C. for 1 day to give the title compound (26.5 mg) as white powder.

$^1$H-NMR Spectrum (DMSO-$d_6$) δ (ppm): 1.35 (2H, m), 1.50-1.70 (4H, m), 1.82 (2H, m), 2.20-4.00 (14H, m), 4.15 (2H, m), 6.73 (1H, m), 7.00-7.30 (6H, m), 7.59-7.63 (2H, m), 7.98 (1H, m), 8.17 (1H, m), 9.92 (1H, s), 10.65 (1H, brs).

Example 1-4)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide fumarate

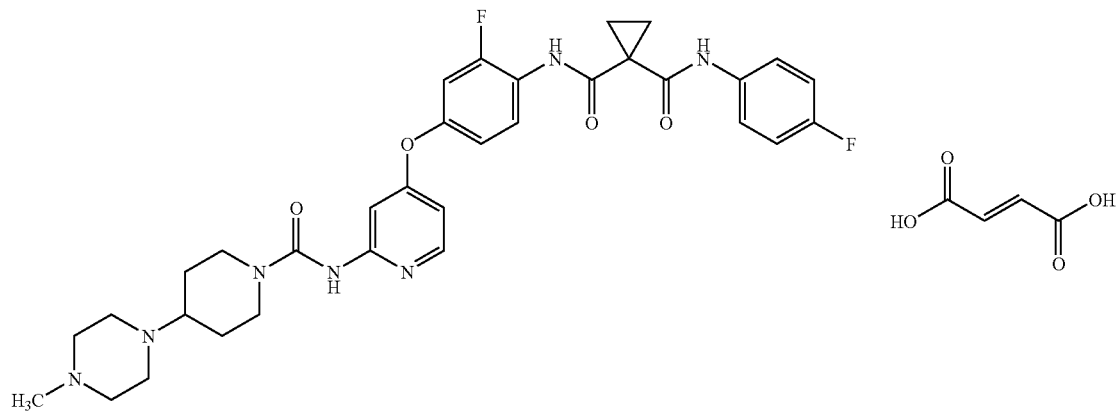 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1 ; O=C(O)/C=C/C(=O)O]

After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (65.3 mg) in 2-propanol (0.653 ml), fumaric acid (6.0 mg) was added. The suspension was sonicated and then stirred at 50° C. for 5 minutes. Water (0.0327 ml) was added and stirring was continued at the same temperature. 2-Propanol (0.653 ml) and water (0.0327 ml) were added and stirring was continued at the same temperature. Fumaric acid (6.0 mg) was added, and after stirring at the same temperature to form a solution, the mixture was further stirred overnight at room temperature. The precipitate was collected by filtration under a nitrogen atmosphere. They were then dried under aeration for 2 hours to give the title compound (26.0 mg, 34%) as white powder.

$^1$H-NMR Spectrum (DMSO-$d_6$) δ (ppm): 1.28 (2H, m), 1.58 (4H, m), 1.73 (2H, m), 2.25 (3H, s), 2.26-2.63 (9H, m), 2.74 (2H, m), 4.10 (2H, m), 6.59 (2H, s), 6.60 (1H, m), 7.01 (1H, m), 7.17 (2H, m), 7.23 (1H, m), 7.40 (1H, d, J=2.0 Hz), 7.59-7.63 (2H, m), 7.93 (1H, m), 8.13 (1H, d, J=5.6 Hz), 9.23 (1H, s), 9.97 (1H, m), 10.55 (1H, m).

Example 1-5)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide succinate

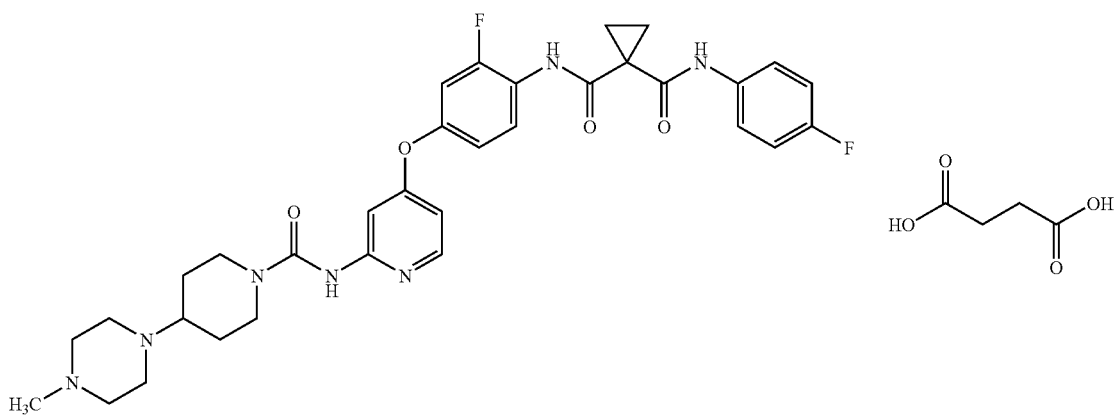 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1 ; O=C(O)CCC(=O)O]

After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (31.7 mg) in ethanol (0.317 ml), succinic acid (5.7 mg) was added at room temperature and the mixture was stirred at room temperature for 3 days. The precipitate was collected by filtration and washed with ethanol (0.158 ml). It was then dried under aeration at room temperature for 30 minutes and further dried with warm air at 60° C. for 4 hours to give the title compound (12.0 mg, 32%) as white powder.

$^1$H-NMR Spectrum (DMSO-$d_6$) δ (ppm): 1.27 (2H, m), 1.50-1.70 (4H, m), 1.72 (2H, m), 2.20 (4H, s), 2.30-2.80 (14H, m), 4.10 (2H, m), 6.61 (1H, m), 7.01 (1H, m), 7.14-7.25 (3H, m), 7.39 (1H, m), 7.59-7.64 (2H, m), 7.93 (1H, m), 8.1.3 (1H, d, J=5.6 Hz), 9.22 (1H, s), 9.96 (1H, m), 10.53 (1H, s).

Example 1-6)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide maleate C. for 4 days. The precipitate was collected by filtration under a nitrogen stream. After washing with acetone (0.020 ml), it was dried under aeration at room temperature for 2 hours to give the title compound (15.1 mg, 20%) as white powder.

$^1$H-NMR Spectrum (DMSO-$d_6$) δ (ppm); 1.30 (2H, m), 1.69 (4H, m), 1.74 (2H, m), 2.14-3.50 (14H, m), 4.34 (2H, m), 6.04 (2H, s), 6.62 (1H, d, J=5.6 Hz), 7.01 (1H, m), 7.17 (2H, m), 7.23 (1H, m), 7.40 (1H, s), 7.61 (2H, m), 7.94 (1H, m), 8.14 (1H, d, J=5.6 Hz), 9.28 (1H, brs), 9.94 (1H, m), 10.58 (1H, m).

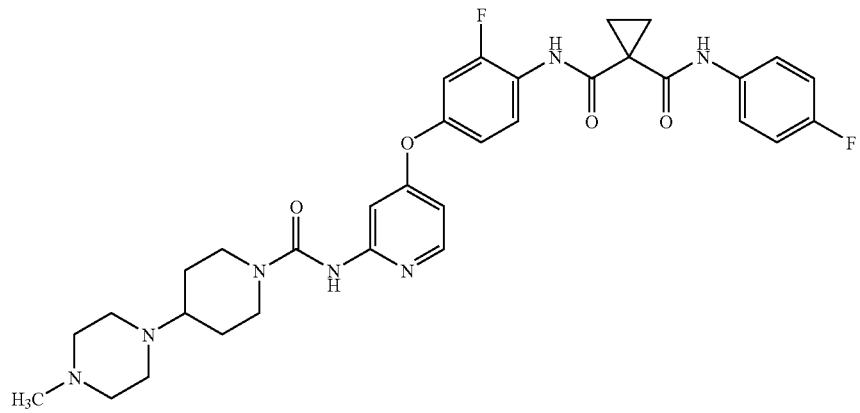

After suspending N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (65.3 mg) in acetone (1.306 ml), maleic acid (12.0 mg) was added. The suspension was sonicated and then stirred at 50° C. for 5 minutes to form a solution. The solution was stirred at room temperature for 16 hours and stirred at 4°

Example 1-7)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2S)-malate

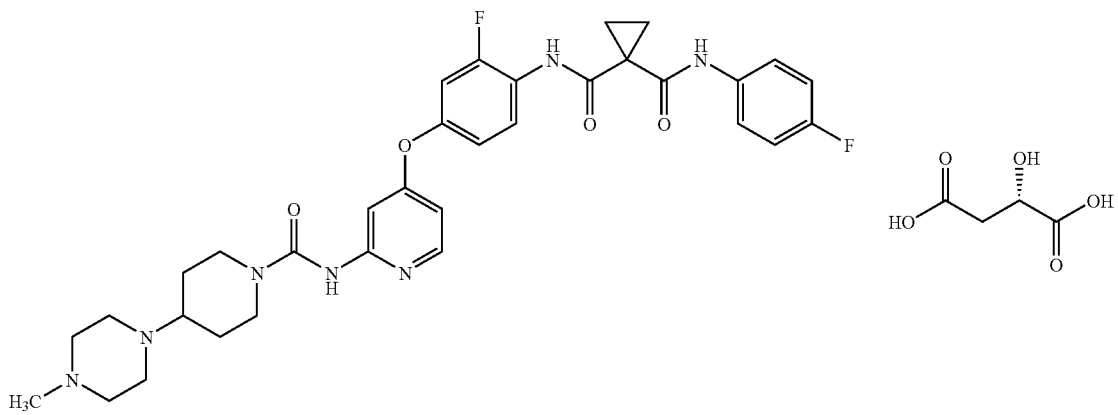 [SMILES: CN1CCN(C2CCN(C(=O)Nc3cc(Oc4ccc(NC(=O)C5(C(=O)Nc6ccc(F)cc6)CC5)c(F)c4)ccn3)CC2)CC1 ; O=C(O)C[C@H](O)C(=O)O]

(Method 1)

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (31.4 mg) was suspended in ethanol (0.317 ml). (2S)-Malic acid (5.7 mg) was added to the suspension at room temperature, and the mixture was stirred at 50° C. to form a solution. The reaction mixture was stirred at room temperature for 18 hours. The precipitate was collected by filtration and washed with ethanol (0.158 ml, 2 times). It was then dried under aeration at room temperature for 30 minutes, and dried with warm air at 60° C. for 1 day to give the title compound (26.0 mg, 68%) as white crystals.

(Method 2)

Crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2S)-malate (36.9 mg) were dissolved in water (0.740 ml). A dry ice/ethanol bath was used to freeze the aqueous solution, after which it was lyophilized under reduced pressure for 67 hours to give the title compound (34.2 mg, 93%) as a white amorphous substance.

$^{1}$H-NMR Spectrum (DMSO-$d_6$) δ (ppm): 1.29 (2H, m), 1.50-1.70 (4H, m), 1.74 (2H, m), 2.20-2.80 (16H, m), 4.03 (1H, m), 4.12 (2H, m), 6.61 (1H, dd, J=2.4, 6.0 Hz), 7.01 (1H, m), 7.17 (2H, m), 7.23 (1H, m), 7.40 (1H, d, J=2.4 Hz), 7.59-7.63 (2H, m), 7.93 (1H, m), 8.13 (1H, d, J=6.0 Hz), 9.24 (1H, s), 9.95 (1H, m), 10.55 (1H, s).

Example 1-8) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2R,3R)-tartrate (Method 2)

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (634 mg) was suspended in ethanol (11.7 ml), and a 1 M solution of L-(+)-tartaric acid in ethanol (1.0 ml) was added to the suspension. It was then heated to 50° C., water (1.27 ml) was added and the mixture was stirred at 50° C. for 10 minutes to form a solution. The solution was stirred for 16 hours while cooling to room temperature. The precipitate was collected by filtration and washed with ethanol (2.0 ml). It was then dried under aeration at room temperature to give the title compound (550 mg, 70%) as colorless crystals.

(Method 3)

Water (1.20 ml) was charged into a mixture of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (600 mg) and L-(+)-tartaric acid (142 mg), and the mixture was stirred. Upon confirming dissolution, acetone (3.6 ml) was added. Seed crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2R,3R)-tartrate were then added, the mixture was stirred for 1 hour and 30 minutes and acetone (2.4 ml) was further added. After stirring at room temperature for 13 hours and 28 minutes, acetone (2.4 ml) was added, stirring was continued for 1 hour and 30 minutes, acetone (2.4 ml) was further added and stirring was continued for 5 hours and 32 minutes. The precipitate was collected by filtration and washed with a mixed solvent of acetone and water (9:1, 2 ml). It was then dried under aeration at room temperature to give the title compound (673 mg, 90%) as colorless crystals.

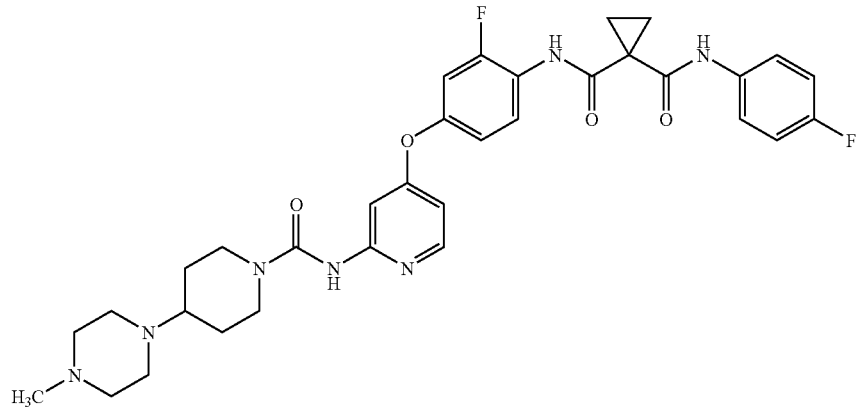

(Method 1)

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (63.4 mg) was suspended in acetone (1.268 ml), and water (0.1268 ml) and L-(+)-tartaric acid (15 mg) were added to the suspension. It was then stirred at 40° C. for 5 minutes to form a solution, which was further stirred at room temperature for 23.5 hours. The precipitate was collected by filtration and washed with acetone (1.0 ml). It was then dried for 6.5 hours at room temperature to give the title compound as colorless crystals (69.1 mg, 88%).

(Method 4)

Water (2.4 ml) was added to L-(+)-tartaric acid (472 mg) and the mixture was stirred at room temperature. After adding acetone (8 ml) to the solution, N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2 g) was added and the mixture was stirred at room temperature to dissolution. Water (0.5 ml) and acetone (1.5 ml) were added to the solution, and after adding additional acetone (8 ml), seed crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2R,3R)-tartrate (2 mg) were added and the mixture was stirred at room temperature for 19 hours. After then adding acetone (14 ml) and stirring at room temperature for 2 hours, the crystals were filtered and dried to give the title compound (2.22 g) as colorless crystals.
(Method 5)

Crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2R,3R)-tartrate (50 mg) were dissolved in water (2.5 ml). A dry ice/ethanol bath was used to freeze the aqueous solution, after which it was lyophilized under reduced pressure for 30 hours to give the title compound (44.2 mg, 88%) as a white amorphous substance.

$^1$H-NMR Spectrum (DMSO-$d_6$) δ (ppm): 1.29 (2H, m), 1.68 (4H, m), 1.74 (2H, m), 2.35 (3H, s), 2.40-2.70 (9H, m), 2.77 (2H, m), 4.07 (2H, s), 4.12 (2H, m), 6.61 (1H, dd, J=2.4, 6.0 Hz), 7.01 (1H, m), 7.17 (2H, m), 7.23 (1H, m), 7.40 (1H, d, J=2.4 Hz), 7.59-7.63 (2H, m), 7.92 (1H, m), 8.14 (1H, d, J=6.0 Hz), 9.24 (1H, s), 9.96 (1H, m), 10.56 (1H, s).

Example 1-9)N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2S,3S)-tartrate

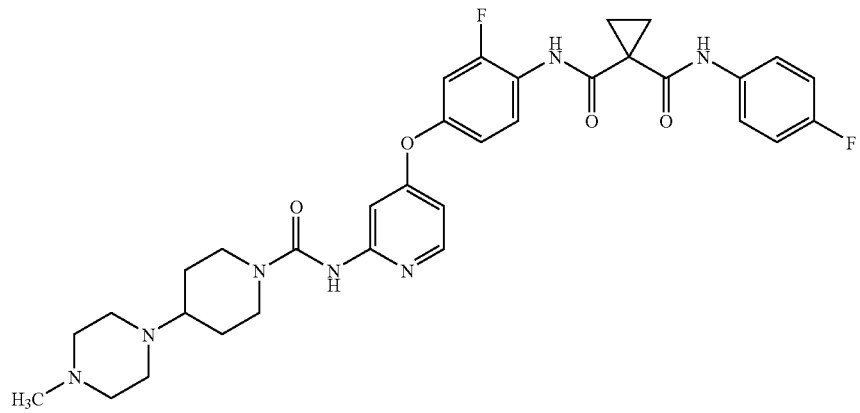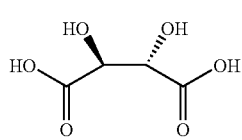

Water (1.44 ml) was added to D-(−)-tartaric acid (284 mg) and the mixture was dissolved at room temperature. Acetone (4.8 ml) and N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (1220 mg) were then added while stirring at room temperature to dissolution, and stirring was continued at room temperature for 6 minutes. Water (0.3 ml) and acetone (5.7 ml) were added to the solution and the mixture was stirred at room temperature for 1 hour. It was then further stirred for 1 hour while cooling on ice and for 15 hours at 4° C. Water (1.5 ml) was added and the reaction mixture was concentrated under reduced pressure. Acetone (5 ml) was added to the obtained residue and concentration under reduced pressure was carried out twice. Acetone (9.6 ml) was then further added, and the mixture was stirred at 4° C. for 24 hours. The precipitated crystals were collected by filtration and washed with acetone (2.4 ml). They were then dried to give the title compound (1.36 g, 92%) as colorless crystals.

Production Example
2-1)1-(Benzyloxy)-2,5-difluoro-4-nitrobenzene

To a solution of 2,4,5-trifluoronitrobenzene (9.48 g) and benzyl alcohol (5.54 ml) in N,N-dimethylformamide (40 ml) was added potassium carbonate (11.1 g), and the mixture was stirred at room temperature for 60 hours. Water (120 ml) was added to the reaction mixture at 0° C. and the mixture was stirred at 4° C. for 24 hours. The precipitated crystals were collected by filtration and washed with water. The crystals were dried under reduced pressure to give the title compound (11.5 g, 81%) as pale yellow crystals.

$^1$H-NMR Spectrum (DMSO-$d_6$) δ (ppm): 5.35 (2H, s), 7.40-7.50 (5H, m), 7.64 (1H, dd, J=7.2, 13.2 Hz), 8.20 (1H, dd, J=7.2, 10.8 Hz).

Production Example
2-2)4-Amino-2,5-difluorophenol

To a solution of 1-(benzyloxy)-2,5-difluoro-4-nitrobenzene (9.21 g) in methanol (300 ml) was added 10% palladium on carbon (921 mg), and the mixture was stirred at room temperature for 24 hours and 20 minutes under a hydrogen atmosphere. After terminating the reaction by substituting the atmosphere in the flask with nitrogen, the catalyst was filtered using Celite. The filtrate was distilled off under reduced pressure to give the title compound (4.96 g, 99%) as a brown solid.

$^1$H-NMR Spectrum (DMSO-$d_6$) δ (ppm): 4.67 (1H, s), 6.53-6.64 (1H, m), 9.03 (1H, s).

Production Example 2-3)4-(4-Amino-2,5-difluorophenoxy)pyridine-2-carboxyamide

After dissolving 4-amino-2,5-difluorophenol (4.95 g) in dimethyl sulfoxide (50 ml) under a nitrogen stream, potassium tert-butoxide (4.05 g) was added at room temperature and the mixture was stirred for 25 minutes. After adding 4-chloropyridine-2-carboxyamide (2.70 g) to the mixture, stirring was continued at 80° C. for 2.5 hours. After cooling the reaction mixture to room temperature, a 1N aqueous solution of sodium hydroxide (74.25 ml) was added and stirring was continued for 10 hours. The precipitated solid was collected by filtration and washed with water. The solid was dried with warm air at 100° C. for 24 hours to give the title compound (3.38 g, 74%) as purple powder.

$^1$H-NMR Spectrum (DMSO-$d_6$) δ (ppm): 5.57 (2H, d, J=6.0 Hz), 6.75-6.80 (1H, m), 7.17-7.20 (1H, m), 7.26 (1H, dd, J=7.2, 10.8 Hz), 7.38 (1H, m), 7.73 (1H, s), 8.14 (1H, s), 8.52 (1H, d, J=5.6 Hz).

ESI-MS (m/z): 288 [M+Na]$^+$.

Production Example 2-4)N-(4-{[2-(Aminocarbonyl)pyridin-4-yl]oxy}-2,5-difluorophenyl)-N'-(4-fluorophenyl)cyclopropane-1,1-dicarboxyamide After dissolving 1-(4-fluorophenylaminocarbonyl)cyclopropanecarboxylic acid (1.35 g) in tetrahydrofuran (25.0 ml) under a nitrogen atmosphere, triethylamine (1.06 ml) was added dropwise while cooling in an ice water bath, and the mixture was stirred for 15 minutes. Thionyl chloride (0.439 ml) was then added at the same temperature and stirring was continued for 1.5 hours. A mixture of 4-(4-amino-2,5-difluorophenoxy)pyridine-2-carboxyamide (1.0 g), tetrahydrofuran (12 ml) and triethylamine (1.06 ml) was then added dropwise to the reaction mixture at the same temperature, and stirring was continued at 0° C. for 24 hours and 45 minutes. The reaction mixture was partitioned between ethyl acetate (70 ml) and a 2N aqueous solution of sodium hydroxide (15 ml). The organic layer was washed twice with a 2N aqueous solution of sodium hydroxide (15 ml), three times with a 1N aqueous solution of hydrochloric acid (15 ml) and once with a saturated aqueous solution of sodium hydrogencarbonate (10 ml) in that order, and then dried over anhydrous sodium sulfate. The solvent was distilled off under reduced pressure. The obtained residue was purified by silica gel column chromatography (Fuji Silysia NH, eluent: heptane:ethyl acetate=1:1 to 1:2, then ethyl acetate) and the fractions containing the target compound were concentrated under reduced pressure. The residue was then dried under reduced pressure to give the title compound (372.8 mg, 21%) as a white solid.

$^1$H-NMR Spectrum (DMSO-$d_6$) δ (ppm): 1.28-1.33 (4H, m), 7.12-7.22 (2H, m), 7.22-7.28 (1H, m), 7.41 (1H, d, J=2.4 Hz), 7.59-7.67 (3H, m), 7.75 (1H, m), 8.10-8.17 (2H, m), 8.56 (1H, d, J=5.6 Hz), 9.80 (1H, m), 11.02 (1H, m).

Production Example 2-5)N-(4-{[2-(Aminopyridin-4-yl)oxy]-2,5-difluorophenyl}-N'-(4-fluorophenyl)cyclopropane-1,1-dicarboxyamide N-(4-{[2-(Aminocarbonyl)pyridin-4-yl]oxy}-2,5-difluorophenyl)-N'-(4-fluorophenyl)cyclopropane-1,1-dicarboxyamide (372.8 mg) was dissolved in N,N-dimethylformamide (5.0 ml). Water (0.0713 ml), [bis(trifluoroacetoxy)iodo]benzene (679 mg) and pyridine (0.384 ml) were added in that order at room temperature and the mixture was stirred for 3 hours. The reaction mixture was partitioned between ethyl acetate (30 ml) and a 1N aqueous solution of sodium hydroxide (9 ml). The organic layer was separated, washed with brine and dried over anhydrous sodium sulfate. The solvent was concentrated under reduced pressure and the residue was purified by silica gel column chromatography (Fuji Silysia NH, eluent: heptane:ethyl acetate 1:3, then ethyl acetate). The fractions containing the target compound were concentrated under reduced pressure and the residue was dried under reduced pressure to give the title compound (301.0 mg, 86%) as white powder.

$^1$H-NMR Spectrum (DMSO-$d_6$) δ (ppm): 1.54-1.68 (4H, m), 5.83 (1H, d, J=2.4 Hz), 5.99 (2H, d, J=5.2 Hz), 6.17 (1H, dd, J=2.4, 5.6 Hz), 7.16-7.20 (2H, m), 7.47-7.53 (1H, m), 7.57-7.62 (2H, m) 7.81 (1H, d, J=5.6 Hz), 8.02-8.10 (1H, m), 9.77 (1H, m), 10.99 (1H, m).

ESI-MS (m/z): 443 [M+H]$^+$.

Production Example 2)N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide After dissolving N-{4-[(2-aminopyridin-4-yl)oxy]-2,5-difluorophenyl}-N'-(4-fluorophenyl)cyclopropane-1,1-dicarboxyamide (100.0 mg) in tetrahydrofuran (1 ml) under a nitrogen atmosphere, triethylamine (0.0630 ml) and phenyl chloroformate (0.0624 ml) were added dropwise in that order at 0° C. and the mixture was stirred for 30 minutes. Ethyl acetate (5 ml) and a saturated aqueous solution of sodium hydrogencarbonate (5 ml) were then added to the reaction mixture which was then stirred. The organic layer was separated, washed with brine and dried over anhydrous sodium sulfate. The solvent was concentrated under reduced pressure. The residue was then dissolved in N,N-dimethylformamide (1.0 ml). After adding 3-hydroxyazetidine hydrochloride (99.0 mg) and triethylamine (0.315 ml) at room temperature, the mixture was stirred for 22 hours and 5 minutes. The reaction mixture was partitioned between ethyl acetate (10 ml) and a saturated aqueous solution of sodium hydrogencarbonate (5 ml). The organic layer was washed with brine and dried over anhydrous sodium sulfate. The solvent was concentrated under reduced pressure. Ethyl acetate (1 ml) and heptane (1 ml) were then added to the obtained residue to precipitate a solid, and the solid was collected by filtration. The obtained solid was purified by silica gel column chromatography (Fuji Silysia NH, eluent: ethyl acetate, then ethyl acetate:methanol=10:1) and the fractions containing the target compound were concentrated under reduced pressure to give the title compound (71.1 mg, 58%) as white powder.

$^1$H-NMR Spectrum (DMSO-$d_6$) δ (ppm): 1.55-1.68 (4H, m), 3.68 (2H, dd, J=4.4, 8.4 Hz), 4.10-4.14 (2H, m), 4.34-4.40 (1H, m), 5.60 (1H, d, J=6.4 Hz), 6.64 (1H, dd, J=2.4, 5.6 Hz), 7.15-7.20 (2H, m), 7.50 (1H, d, J=2.4 Hz), 7.52-7.62 (3H, m), 8.05-8.14 (1H, m), 8.13 (1H, d, J=5.6 Hz), 9.20 (1H, s), 9.81 (1H, m), 10.99 (1H, m).

ESI-MS (neg.) (m/z): 540 [M−H]$^-$.

Production Example 2'-1)4-(4-Amino-2,5-difluorophenyl)pyridine-2-carboxamide 4-Amino-2,5-difluorophenol (4.95 g) was dissolved in dimethyl sulfoxide (50 ml) under a nitrogen stream, and potassium tert-butoxide (4.05 g) was added at room temperature, and the mixture was stirred for 25 minutes. 4-Chloropyridine-2-carboxamide (2.70 g) was added to the mixture, which was stirred at 80° C. for 2.5 hours. The reaction mixture was allowed to cool down to room temperature, and a 1N aqueous solution of sodium hydroxide (74.25 ml) was added, and the mixture was stirred for 10 hours. The precipitated solid was collected by filtration, and the resultant solid was washed with water. The solid was dried by hot air at 100° C. for 24 hours to give the title compound (3.38 g, 74%) as purple powder.

$^1$H-NMR Spectrum (DMSO-$d_6$) δ (ppm): 5.57 (2H, d, J=6.0 Hz), 6.75-6.80 (1H, m), 7.17-7.20 (1H, m), 7.26 (1H, dd, J=7.2, 10.8 Hz). 7.38 (1H, m), 7.73 (1H, s), 8.14 (1H, s), 8.52 (OH, d, J=5.6 Hz).

ESI-MS (m/z): 288 [M+Na]$^+$.

Production Example 2'-2)Benzyl 1-{[(4-{[2-(aminocarbonyl)pyridin-4-yl]oxy}-2,5-difluorophenyl)amino]carbonyl}cyclopropanecarboxylate 1-[(Benzyloxy)carbonyl]cyclopropanecarboxylic acid (1.04 g) was dissolved in tetrahydrofuran (15 ml) under a nitrogen atmosphere. N-Methylmorpholine (0.520 ml) was added at 0° C., and the mixture was stirred for 15 minutes. Thionyl chloride (0.345 ml) was added to the mixture at 0° C., and the mixture was stirred at the same temperature for 30 minutes; 4-(4-Amino-2,5-difluorophenoxy)pyridine-2-carboxamide (500 mg) and N-methylmorpholine (0.520 ml) were added, and the mixture was stirred at room temperature for 2 hours and 50 minutes. The reaction mixture was partitioned after the addition of a 1N aqueous solution of sodium hydroxide (15 ml) and ethyl acetate (20 ml). The organic layer was washed with a 1N aqueous solution of sodium hydroxide (15 ml), water (15 ml) and brine (15 ml), and dried over anhydrous magnesium sulfate. The desiccant was removed by filtration, and the filtrate was concentrated under reduced pressure. The resultant residue was purified by silica gel column chromatography (Fuji Silysia NH, eluent; heptane: ethyl acetate=1:1, to 1:2). The fractions containing the target compound was concentrated under reduced pressure to give the title compound (822.7 mg, 93%) as white powder.

$^1$H-NMR Spectrum (DMSO-$d_6$) δ (ppm): 1.58-1.63 (4H, m), 5.20 (2H, s), 7.24-7.27 (1H, m), 7.30-7.42 (5H, m), 7.43 (1H, d, J=2.8 Hz), 7.63-7.71 (1H, m), 7.72-7.78 (1H, m), 8.13-8.22 (2H, m) 8.56 (1H, d, J=5.6 Hz), 10.93 (1H, brs).

ESI-MS (m/z): 490[M+Na]$^+$.

Production Example 2'-3) Benzyl 1-[({4-[(2-aminopyridin-4-yl)oxy]-2,5-difluorophenyl}amino)carbonyl]cyclopropanecarboxylate Benzyl 1-{[(4-{[2-(aminocarbonyl)pyridin-4-yl]oxy}-2,5-difluorophenyl)amino]carbonyl}cyclopropanecarboxylate (1.55 g) was dissolved in N,N-dimethylformamide (33 ml). Water (0.299 ml) and iodobenzene diacetate (1.18 g) were added at room temperature, and the mixture was stirred for 15 hours and 20 minutes. Iodobenzene diacetate (215 mg) was added again and the mixture was stirred for 2 hours and 20 minutes. Water (150 ml) was added to the mixture, and the mixture was stirred for 1 hour, and partitioned after the addition of a saturated aqueous solution of sodium hydrogencarbonate (200 ml) and ethyl acetate (300 ml). The organic layer was washed with water (200 ml, twice) and brine (150 ml), and dried over anhydrous magnesium sulfate. The desiccant was removed by filtration, and the filtrate was concentrated under reduced pressure. The resultant residue was purified by silica gel column chromatography (Fuji Silysia NH, eluent; heptane:ethyl acetate=1:2). The fractions containing the target compound were concentrated under reduced pressure to give the title compound (1.217 g, 83%) as a pale yellow solid.

$^1$H-NMR Spectrum (DMSO-$d_6$) δ (ppm): 1.54-1.65 (4H, m), 5.19 (2H, s), 5.83 (1H, d, J=2.0 Hz): 5.99 (2H, brs), 6.18 (1H, dd, J=2.4, 5.6 Hz), 7.30-7.45 (5H, m), 7.52 (1H, dd, J=7.2, 10.8 Hz), 7.82 (1H, d, J=5.6 Hz), 8.05-8.20 (1H, m), 10.86 (1H, brs).

ESI-MS (m/z): 440[M+H]$^+$.

Production Example 2'-4) Benzyl 1-({[4-({2-[(phenoxycarbonyl)amino]pyridin-4-yl}oxy)-2,5-difluorophenyl]amino}carbonyl)cyclopropanecarboxylate Benzyl 1-[({4-[(2-aminopyridin-4-yl)oxy]-2,5-difluorophenyl}amino)carbonyl]cyclopropanecarboxylate (1.15 g) was dissolved in tetrahydrofuran (12 ml) under a nitrogen atmosphere. Pyridine (0.424 ml) and phenyl chloroformate (0.657 ml) were added at room temperature, and the mixture was stirred for 20 minutes. A saturated aqueous solution of sodium hydrogencarbonate (36 ml) and hexane (36 ml) were added to the mixture, and the mixture was stirred for 55 minutes. The precipitated solid was collected by filtration. The resultant solid was washed with hexane and dried under aeration and dried by hot air (60° C.) for 5 hours. Water (150 ml) was added to the solid, and the mixture was stirred for 2 hours, and the solid was collected by filtration, and the resultant solid was washed with water. The solid was dried by hot air (60° C.) for 3 days to give the title compound (1.117 g, 76%) as a white solid.

$^1$H-NMR Spectrum (CDCl$_3$) δ (ppm): 1.69-1.90 (4H, m), 5.19 (2H, s), 6.62 (1H, dd, J=2.4, 6.0 Hz), 6.95-7.04 (1H, m), 7.12-7.21 (1H, m), 7.28-7.45 (9H, m), 7.56 (1H, d, J=2.4 Hz), 8.19 (1H, d, J=6.0 Hz), 8.34 (1H, dd, J=7.2, 12.0 Hz), 8.49 (1H, brs), 11.27 (1H, brs).

Production Example 2'-5

Benzyl 1-[({2,5-difluoro-4-[(2-{[(3-hydroxyazetidin-1-yl)carbonyl]amino}pyridin-4-yl)oxy]phenyl}amino)carbonyl]cyclopropanecarboxylate Triethylamine (0.100 ml) was added to a mixture of benzyl 1-({[4-({2-[(phenoxycarbonyl)amino]pyridin-4-yl}oxy)-2,5-difluorophenyl]amino}carbonyl)cyclopropanecarboxylate (200 mg), 3-hydroxyazetidine hydrochloride (39.1 mg) and N,N-dimethylformamide (4.0 ml) at room temperature under a nitrogen atmosphere, and the mixture was stirred for 6 hours and 10 minutes. 3-Hydroxyazetidine hydrochloride (10.0 mg) and triethylamine (0.025 ml) were added at room temperature, and the mixture was stirred for 1 hour and 20 minutes. A saturated aqueous solution of sodium hydrogencarbonate (16 ml) and hexane (5 ml) were added to the mixture, and the precipitated solid was collected by filtration. The solid was washed with water (2 ml, three times), and dried under aeration. The resultant solid was purified by silica gel column chromatography (Fuji Silysia NH, eluent; ethyl acetate, then ethyl acetate:methanol=10:1). The fractions containing the target compound was concentrated under reduced pressure to give the title compound (86.7 mg, 45%) as a white solid.

$^1$H-NMR Spectrum (CDCl$_3$) δ (ppm): 1.72-1.86 (4H, m), 3.93 (2H, dd, J=4.4, 10.0 Hz), 4.26-4.32 (2H, m), 4.66-4.73 (1H, m), 5.20 (2H, s), 6.54 (1H, dd, J=2.0, 6.0 Hz), 6.89 (1H, brs), 7.00 (1H, dd, J=7.2, 10.4 Hz), 7.30-7.43 (5H, m), 7.65 (1H, d, J=2.0 Hz), 8.04 (1H, d, J=6.0 Hz), 8.34 (1H, dd, J=7.2, 12.0 Hz), 11.27 (1H, brs).

ESI-MS (m/z): 537[M−H]$^−$.

Production Example 2'-6) 1-[({2,5-Difluoro-4-[(2-{[(3-hydroxyazetidin-1-yl)carbonyl]amino}pyridin-4-yl)oxy]phenyl}amino)carbonyl]cyclopropanecarboxylic acid triethylamine salt Benzyl 1-[({2,5-difluoro-4-[(2-{[(3-hydroxyazetidin-1-yl)carbonyl]amino}pyridin-4-yl)oxy]phenyl}amino)carbonyl]cyclopropanecarboxylate (84.2 mg) was dissolved in tetrahydrofuran and methanol (1:1) (2 ml) under a nitrogen atmosphere. 10% palladium on carbon (33.2 mg) was added and the air in the reaction vessel was replaced by hydrogen, and the mixture was stirred at room temperature for 20 hours. The air in the reaction vessel was replaced by nitrogen, and triethylamine (0.0435 ml) was added, and the mixture was stirred for 30 minutes. The catalyst was removed by filtration, and washed with methanol. The filtrate was concentrated under reduced pressure to give the title compound (75.3 mg, 88%) as a white solid.

ESI-MS (m/z): 447[M−H]$^−$.

Production Example 2')N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide (Compound 2)

4-(4,6-Dimethoxy[1,3,5]triazin-2-yl)-4-methylmorpholinium chloride hydrate (80.8 mg) was added to a mixture of 1-[({2,5-difluoro-4-[(2-{[(3-hydroxyazetidin-1-yl)carbonyl]amino}pyridin-4-yl)oxy]phenyl}amino)carbonyl]cyclopropanecarboxylic acid triethylamine salt (75.3 mg), 4-fluoroaniline (0.026 ml) and tetrahydrofuran (1.0 ml) at room temperature under a nitrogen atmosphere, and the mixture was stirred for 5 hours. 4-(4,6-Dimethoxy[1,3,5]triazin-2-yl)-4-methylmorpholinium chloride hydrate (80.8 mg) was added again at room temperature, and the mixture was stirred for 87 hours. A saturated aqueous solution of sodium hydrogencarbonate (5 ml) was added to the reaction mixture and stirred, and the mixture was partitioned after the addition of ethyl acetate (20 ml) and water (20 ml). The organic layer was washed with brine (10 ml), and dried over anhydrous magnesium sulfate. The desiccant was removed by filtration, and the filtrate was concentrated under reduced pressure. The resultant residue was purified by silica gel column chromatography (Fuji Silysia NH, eluent; ethyl acetate, ethyl acetate:methanol=10:1). The fractions containing the target compound was concentrated under reduced pressure to give the title compound (68.1 mg, 92%) as a white solid.

$^1$H-NMR Spectrum (DMSO-$d_6$) δ (ppm): 1.54-1.68 (4H, m), 3.65-3.72 (2H, m), 4.09-4.15 (2H, m), 4.33-4.41 (1H, m), 5.60 (1H, d, J=6.4 Hz), 6.62-6.66 (1H, m), 7.14-7.22 (2H, m), 7.50-7.65 (4H, m), 8.05-8.15 (1H, m), 8.13 (1H, d, J=5.6 Hz), 9.19 (1H, brs), 9.79-9.84 (1H, m), 10.95-11.02 (1H, m).

ESI-MS (m/z): 540[M−H]$^-$.

Example 2-1) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide hydrochloride

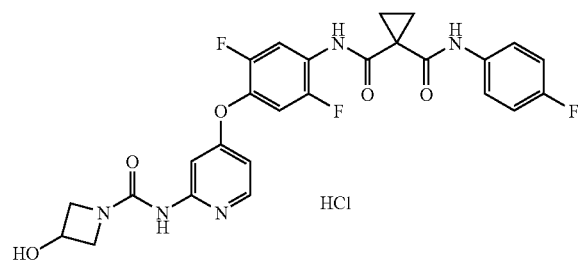 [SMILES: O=C(Nc1cc(Oc2cc(F)c(NC(=O)C3(C(=O)Nc4ccc(F)cc4)CC3)cc2F)ccn1)N1CC(O)C1 ; Cl]

N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (32.5 mg) was suspended in acetone (0.325 ml). 5N hydrochloric acid (0.012 ml) was added at room temperature. After adding water (0.151 ml), the mixture was heated and stirred at 50° C. for 5 minutes to form a solution. The solution was stirred at room temperature for 30 minutes, acetone (0.325 ml) was added, and stirring was continued for 26 hours. The precipitate was collected by filtration and washed with acetone (0.163 ml, twice). It was then dried under aeration at room temperature for 1 hour and then dried with warm air at 60° C. for 12 hours to give the title compound (27.6 mg, 80%) as white crystals.

$^1$H-NMR Spectrum (DMSO-$d_6$) δ (ppm): 1.50-1.80 (4H, m), 3.50-4.30 (4H, m), 4.45 (1H, m), 7.02 (1H, m), 7.10-7.25 (3H, m), 7.55-7.65 (2H, m), 7.68 (1H, m), 8.18 (1H, dd, J=7.2, 12.0 Hz), 8.25 (1H, d, J=6.4 Hz), 9.78 (1H, s), 10.29 (1H, br), 11.20 (1H, brs).

Example 2-2) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide hydrobromide

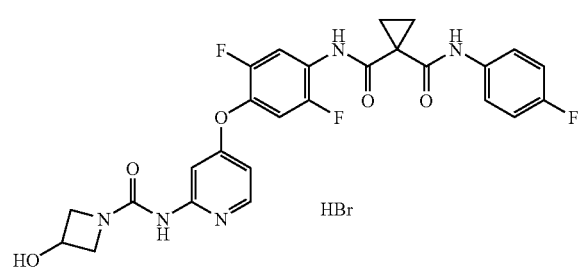 [SMILES: O=C(Nc1cc(Oc2cc(F)c(NC(=O)C3(C(=O)Nc4ccc(F)cc4)CC3)cc2F)ccn1)N1CC(O)C1 ; Br]

N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (32.5 mg) was suspended in ethanol (0.325 ml). After adding 48% aqueous hydrobromic acid (0.010 ml) at room temperature to form a solution, it was stirred at room temperature, for 23 hours. The precipitate was collected by filtration and washed with ethanol (0.163 ml, twice). It was then dried under aeration at room temperature for 1 hour and then dried with warm air at 60° C. for 12 hours to give the title compound (30.7 mg, 82%) as white crystals.

$^1$H-NMR Spectrum (DMSO-$d_6$) δ (ppm): 1.50-1.75 (4H, m), 3.50-4.30 (4H, m), 4.45 (1H, m), 7.00 (1H, m), 7.08 (1H, m), 7.16-7.21 (2H, m), 7.55-7.65 (2H, m), 7.68 (1H, m), 8.17 (1H, dd, J=7.2, 12.0 Hz), 8.23 (1H, d, J=6.8 Hz), 9.76 (1H, s), 10.02 (1H, br), 11.17 (1H, brs).

Example 2-3) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide ½ sulfate N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (32.5 mg) was suspended in ethanol (0.325 ml). After adding 2.5 M sulfuric acid (0.012 ml) at room temperature to form a solution, it was stirred at room temperature for 24 hours. The precipitate was collected by filtration and washed with ethanol (0.163 ml, twice). It was then dried under aeration at room temperature for 1 hour and then dried with warm air at 60° C. for 12 hours to give the title compound (31.2 mg, 88%) as white crystals.

$^1$H-NMR Spectrum (DMSO-$d_6$) δ (ppm): 1.50-1.75 (4H, m), 3.50-4.25 (4H, m), 4.43 (1H, m), 6.92 (UH, m), 7.10-7.30 (3H, m), 7.50-7.70 (3H, m), 8.15 (1H, dd, J=6.8, 12.0 Hz), 8.21 (1H, d, J=6.4 Hz), 9.77 (1H, s), 11.13 (1H, brs).

Example 2-4) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide methanesulfonate (Method 1)
N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (30.0 mg) was suspended in ethanol (0.300 ml). After adding methanesulfonic acid (0.004 ml) at room temperature to form a solution, it was stirred at room temperature for 90 hours and 50 minutes. Ethanol (1 ml) was added, and then the precipitate was collected by filtration and washed with tert-butyl methyl ether (1 ml, three times). It was then dried under aeration at room temperature for 1 hour to give the title compound (26.3 mg, 75%) as white crystals.

(Method 2)

Water (1.0 ml) and tert-butanol (1.0 ml) were added to crystals of N-{2,5-difluoro-4-[(2-{[(3-hydroxyazetidin-1-yl)carbonyl]amino}pyridin -4-yl)oxy]phenyl}-N'-(4-fluorophenyl)cyclopropane-1,1-dicarboxyamide methanesulfonate (50.0 mg) at room temperature for dissolution. A dry ice/ethanol bath was used to freeze the solution, after which it was lyophilized under reduced pressure for 6 days to give the title compound (47.1 mg, 94%) as a white amorphous substance.

$^1$H-NMR Spectrum (DMSO-$d_6$) δ (ppm): 1.52-1.76 (4H, m), 2.31 (3H, s), 3.70-3.84 (2H, m), 4.15-4.30 (2H, m), 4.41-4.50 (1H, m), 6.96-7.12 (2H, m), 7.14-7.25 (2H, m), 7.55-7.63 (2H, m), 7.64-7.76 (1H, m), 8.18 (1H, dd, J=7.2, 12.0 Hz), 8.26 (1H, d, J=6.8 Hz), 9.75 (1H, s), 10.12 (1H, brs), 11.19 (1H, brs).

Example 2-5) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide ethanesulfonate N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (32.5 mg) was suspended in ethanol (0.325 ml). After adding ethanesulfonic acid (0.006 ml) at room temperature to form a solution, it was stirred at room temperature for 25 hours. The precipitate was collected by filtration and washed with ethanol (0.163 ml, 2 times). It was then dried under aeration at room temperature for 1 hour and dried with warm air at 60° C. for 12 hours to give the title compound (25.5 mg, 65%) as white crystals.

$^1$H-NMR Spectrum (DMSO-$d_6$) δ (ppm): 1.05 (3H, t, J=7.2 Hz), 1.50-1.75 (4H, m), 2.37 (2H, q, J=7.2 Hz), 3.70-4.30 (4H, m), 4.44 (1H, m), 6.99 (1H, m), 7.11 (1H, m), 7.15-7.25 (2H, m), 7.55-7.63 (2H, m), 7.67 (1H, m), 8.17 (1H, dd, J=7.2, 12.0 Hz), 8.24 (1H, d, J=6.8 Hz), 9.76 (1H, s), 9.96 (1H, br), 11.16 (1H, brs).

Example 2-6) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide benzenesulfonate N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (31.6 mg) was suspended in ethanol (0.316 ml). After adding benzenesulfonic acid (10.2 mg) at room temperature to form a solution, it was stirred at room temperature for 17 hours and 50 minutes. Ethanol (0.5 ml) was added, and then the precipitate was collected by filtration and washed with tert-butyl methyl ether (1 ml, three times). It was then dried under aeration at room temperature for 1 hour to give the title compound (30.4 mg, 74%) as white crystals.

$^1$H-NMR Spectrum (DMSO-$d_6$) δ (ppm): 1.55-1.72 (4H, m), 3.70-3.81 (2H, m), 4.15-4.26 (2H, m), 4.40-4.49 (1H, m), 7.00 (1H, m), 7.08 (1H, m), 7.14-7.23 (2H, m), 7.28-7.35 (3H, m), 7.55-7.63 (4H, m), 7.67 (1H, dd, J=7.2, 10.0 Hz), 8.13-8.22 (1H, m), 8.24 (1H, d, J=6.4 Hz), 9.75 (1H, s), 10.01 (1H, brs), 11.17 (1H, brs).

Example 2-7) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide 4-methylbenzenesulfonate (Method 1)

N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide (34.2 mg) was suspended in ethanol (0.342 ml). p-Toluenesulfonic acid monohydrate (13.2 mg) was added at room temperature to form a solution, which was then stirred at room temperature for 90 hours and 25 minutes. Ethanol (1 ml) was added, and the precipitate was collected by filtration and washed with tert-butyl methyl ether (1 ml, three times). It was then dried under aeration at room temperature for 1 hour to give the title compound (33.0 mg, 73%) as white crystals.

(Method 2)

Water (6.0 ml) and tert-butanol (6.0 ml) were added to crystals of N-{2,5-difluoro-4-[(2-{[(3-hydroxyazetidin-1-yl)carbonyl]amino}pyridin -4-yl)oxy]phenyl}-N'-(4-fluorophenyl)cyclopropane-1,1-dicarboxyamide 4-methylbenzenesulfonate (50.0 mg) for dissolution. A dry ice/ethanol bath was used to freeze the solution, after which it was lyophilized under reduced pressure for 6 days to give the title compound (45.1 mg, 90%) as a white amorphous substance.

$^1$H-NMR Spectrum (DMSO-$d_6$) δ (ppm): 1.55-1.72 (4H, m), 2.29 (3H, s), 3.70-3.84 (2H, m), 4.14-4.26 (2H, m), 4.40-4.49 (1H, m), 7.01 (1H, m), 7.07 (1H, m), 7.11 (2H, d, J=8.0 Hz), 7.15-7.24 (2H, m), 7.47 (2H, d, J=8.0 Hz), 7.55-7.64 (2H, m), 7.64-7.72 (1H, m), 8.13-8.21 (1H, m), 8.24 (1H, d, J=6.8 Hz), 9.75 (1H, s), 10.04 (1H, brs), 11.17 (1H, brs).

(X-Ray Powder Diffraction Measurement)

The crystals obtained in Examples 1-7 (Method 1), 1-8 (Method 1), 2-1, 2-2, 2-3, 2-4 (Method 1), 2-5, 2-6 and 2-7 (Method 1) and the amorphous substances obtained in Examples 1-7 (Method 2), 1-8 (Method 5), 2-4 (Method 2) and 2-7 (Method 2) in sample amounts of about 5 mg were ground in a mortar and then placed on an aluminum measuring pan for measurement under the following conditions.

X-rays: DSC System TTR-III (Rigaku, Kapan)
Target: CuKα ray
Goniometer: TTR-III horizontal goniometer
Counter: Scintillation counter
Tube voltage: 50 kV
Tube current: 300 mA
Scan speed: 5/min
Scan axis: 2θ/θ
Scan range: 2θ=5° to 35°
Divergence slit: 0.5°
Vertical divergence limited slit: 2 mm
Scattering slit: open
Receiving slit: open
Sampling width: 0.02°
Repeat count: 1

The X-ray powder diffraction patterns for the crystals obtained in Examples 1-7 (Method 1), 1-8 (Method 1), 2-1, 2-2, 2-3, 2-4 (Method 1), 2-5, 2-6 and 2-7 (Method 1) and the amorphous substances obtained in Examples 1-7 (Method 2), 1-8 (Method 5), 2-4 (Method 2) and 2-7 (Method 2) are shown in FIGS. 1 to 13, and the representative peaks at diffraction angles (2θ) and the relative intensities for each of the crystals are shown in Tables 1 to 9.

TABLE 1

| 2θ | Relative intensity |
|---|---|
| 10.8 | 37 |
| 12.3 | 57 |
| 14.3 | 49 |
| 17.7 | 100 |
| 19.0 | 90 |
| 19.7 | 61 |
| 21.7 | 54 |
| 22.0 | 35 |
| 23.5 | 69 |
| 24.7 | 40 |

TABLE 2

| 2θ | Relative intensity |
|---|---|
| 10.7 | 36 |
| 12.2 | 59 |
| 14.3 | 39 |
| 17.7 | 100 |
| 19.0 | 84 |
| 19.6 | 55 |
| 21.4 | 45 |
| 22.1 | 43 |
| 23.4 | 60 |
| 24.8 | 46 |

TABLE 3

| 2θ | Relative intensity |
|---|---|
| 7.4 | 29 |
| 10.3 | 100 |
| 12.0 | 38 |
| 13.9 | 37 |
| 15.0 | 40 |
| 16.5 | 37 |
| 24.7 | 69 |
| 25.1 | 78 |
| 25.9 | 50 |
| 26.6 | 39 |

TABLE 4

| 2θ | Relative intensity |
|---|---|
| 8.3 | 21 |
| 10.4 | 75 |
| 12.2 | 22 |
| 14.0 | 34 |
| 16.2 | 37 |
| 17.7 | 30 |
| 19.5 | 63 |
| 20.4 | 35 |
| 25.3 | 100 |
| 28.0 | 34 |

TABLE 5

| 2θ | Relative intensity |
|---|---|
| 6.5 | 98 |
| 6.9 | 73 |
| 9.3 | 100 |
| 16.0 | 54 |
| 18.7 | 46 |
| 19.5 | 68 |
| 22.0 | 71 |
| 22.9 | 45 |

TABLE 5-continued

| 2θ | Relative intensity |
|---|---|
| 23.9 | 55 |
| 26.7 | 40 |

TABLE 6

| 2θ | Relative intensity |
|---|---|
| 7.9 | 34 |
| 9.9 | 41 |
| 13.9 | 53 |
| 17.7 | 69 |
| 19.1 | 55 |
| 20.4 | 85 |
| 21.7 | 82 |
| 22.4 | 48 |
| 23.3 | 100 |
| 25.8 | 41 |

TABLE 7

| 2θ | Relative intensity |
|---|---|
| 6.7 | 100 |
| 10.1 | 41 |
| 12.7 | 17 |
| 13.7 | 15 |
| 16.9 | 38 |
| 18.5 | 42 |
| 19.4 | 27 |
| 21.5 | 34 |
| 22.1 | 35 |
| 23.4 | 15 |

TABLE 8

| 2θ | Relative intensity |
|---|---|
| 7.8 | 100 |
| 8.3 | 87 |
| 8.8 | 58 |
| 13.7 | 36 |
| 17.4 | 63 |
| 18.5 | 74 |
| 19.7 | 63 |
| 20.8 | 51 |
| 24.3 | 36 |
| 24.6 | 38 |

TABLE 9

| 2θ | Relative intensity |
|---|---|
| 7.2 | 86 |
| 13.4 | 43 |
| 17.3 | 59 |
| 18.8 | 29 |
| 19.3 | 37 |
| 20.6 | 53 |
| 21.1 | 42 |
| 23.6 | 100 |
| 24.6 | 58 |
| 26.1 | 51 |

($^{13}$C Solid NMR Spectral Analysis)

$^{13}$C solid NMR spectral analysis of the crystals obtained in Example 1-8 (Method 4) was carried out under the following conditions.
Measuring apparatus: AVANCE 400 MHz (Bruker)
Probe: 7 mm—CP/MAS (Bruker)

NMR cell diameter: 7 mm
Cell spinning rate: 5000 rotations/sec
Measuring method: CPTOSS
Observed nucleus: $^{13}$C (Resonance frequency: 100.6248425 MHz)
Latency time: 3 seconds
Contact time: 1000 microseconds
Number of integration: 5910
External standard: The chemical shift for the carbonyl carbon of glycine was set as 176.03 ppm.

Figure 14:
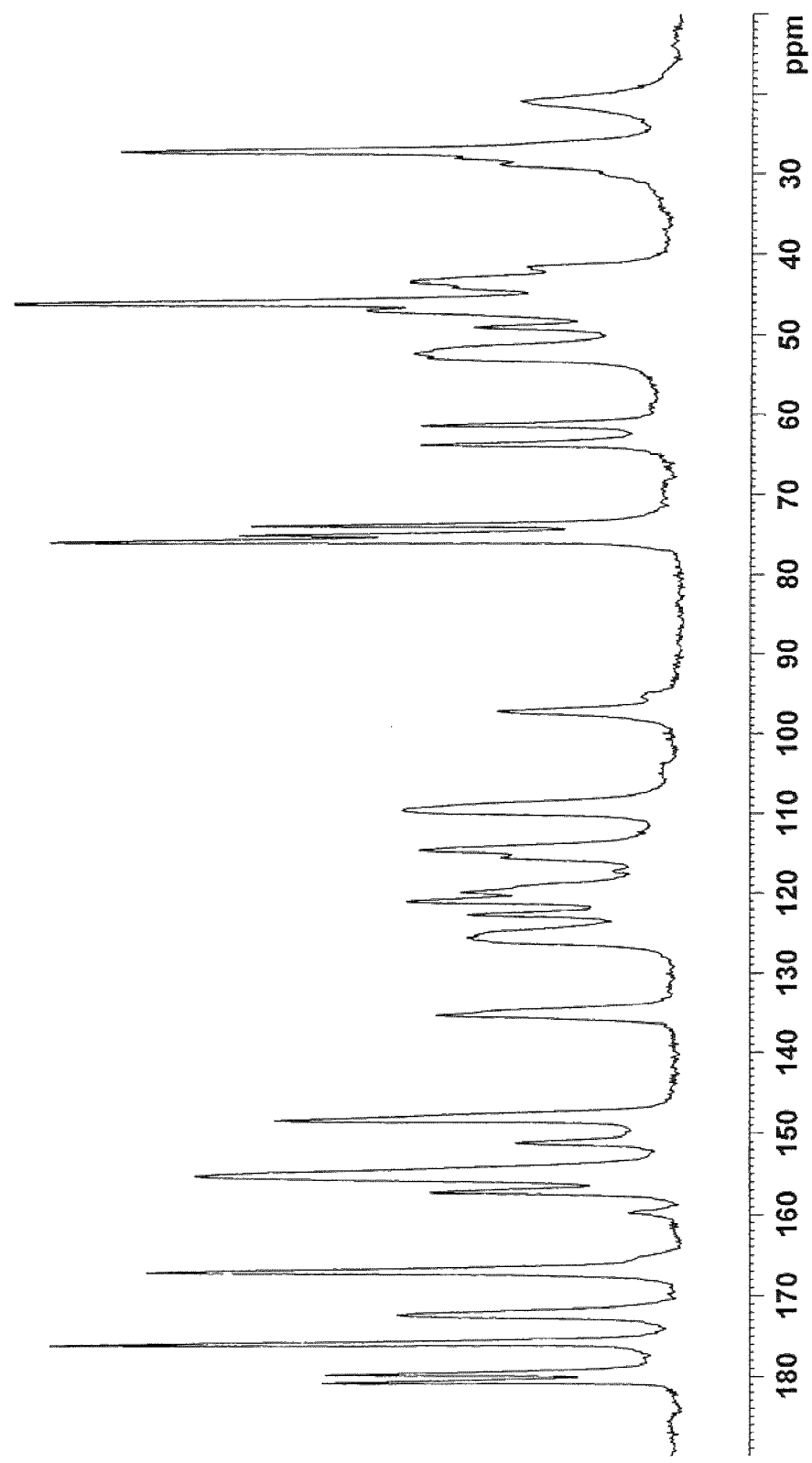
FIG. 14 shows a $^{13}C$ solid NMR spectrum for crystals of the tartarate of Compound 1 obtained in Example 1-8 (Method 4).

FIG. 14 shows the $^{13}$C solid NMR spectrum for the crystals obtained in Example 1-8 (Method 4), and Table 10 shows the chemical shifts.

TABLE 10

| Chemical shift (ppm) | | |
|---|---|---|
| 180.5 | 122.5 | 61.2 |
| 179.5 | 120.8 | 52.1 |
| 175.7 | 119.7 | 49.0 |
| 172.1 | 115.4 | 46.8 |
| 166.7 | 114.4 | 45.7 |
| 157.1 | 109.4 | 43.3 |
| 154.9 | 97.1 | 41.5 |
| 151.1 | 75.6 | 28.7 |
| 148.1 | 74.8 | 28.0 |
| 135.2 | 73.6 | 26.9 |
| 125.4 | 63.6 | 20.8 |

Pharmacological Test Examples

The biological activity and pharmaceutical effect (inhibitory activity for hepatocyte growth factor receptor, anti-tumor activity, inhibitory activity for angiogenesis, and inhibitory activity for cancer metastasis) of the compounds 1 and 2 were evaluated by methods described below.

Abbreviations and terms used in the following Pharmacological Test Examples are listed as follows:

Abbreviation List

HGFR (Hepatocyte growth factor receptor)
DNA (Deoxyribonucleic acid)
Human placenta (Human placenta)
PCR (Polymerase chain reaction)
VEGFR2 (Vascular endothelial growth factor receptor 2)
FGFR1 (Fibroblast growth factor receptor 1)
PDGFRβ (Platelet derived growth factor β)
EGFR (Epidermal growth factor receptor)
FBS (Fetal bovine serum)
PBS (Phosphate buffered saline)
Tris (Tris(hydroxymethyl)aminomethane, Tris(buffer))
PMSF (Phenylmethylsulfonyl fluoride)
NP-40 (Nonidet. P-40)
EGTA (O,O-Bis(2-aminoethyleneglycol)-N,N,N',N'-tetraacetic acid)
SDS (Sodium dodecyl sulfate)
BSA (Bovine, serum albumin)
Hepes (N-[2-hydroxyethyl]piperazine-N'-[2-ethanesulfonic acid], Hepes(buffer))
ATP (Adenosine 5'-triphosphate)
EDTA (Ethylenediamine tetraacetic acid)
HTRF (Homogenous Time-Resolved Fluorescence)
HRP (Horseradish peroxidase)
ELISA (Enzyme-linked immunosorbent assay)

Pharmacological Test Example 1:Inhibitory Activity Against Receptor Tyrosine Kinase Activity 1. Cloning of Receptor Tyrosine Kinases, and Preparation of the Recombinant Baculovirus Solutions The cytoplasmic domain of HGFR (GenBank Accession No. J02958) is a 1.3 kb DNA fragment beginning with Lys974 and including a stop codon, and described by Park et al. (Proc. Natl. Acad. Sci. U.S.A. 84(18), 6379-6383, 1987). The DNA fragment was isolated from the human placental cDNA library (purchased from Clontech) by PCR (TaKaRa Ex Taq™ Kit, purchased from TaKaRa) using two: kinds of primers (SEQ ID NO: 1, 5'-CCGGCCGGATCCAAAAA-GAGAAAGCAAATTAAA-3' and SEQ ID NO: 2, 5'-TTAATTCTGCAGCTATGATGTCTCCCAGAAGGA-3', purchased from Invitrogen). The DNA fragment was cloned into a baculovirus transplace vector (pFastBac™-HT (purchased from GIBCO BRL)) to produce a recombinant construct. The construct was transfected into insect cells (Spodoptera frugiperda 9(Sf9)) to produce a solution of HGFR transfected baculovirus (preparation of a recombinant baculovirus can be found in the standard text (Bac-to-Bac Baculovirus Expression System (GIBCO BRL)). The cloning of the other receptor tyrosine kinases and preparation of the recombinant baculovirus solutions were prepared using a cytoplasmic fragment starting from Lys791 (VEGFR2, GenBank Accession No. L04947), a cytoplasmic fragment starting from Lys398 (FGFR1, GenBank Accession No. X52833) and a cytoplasmic fragment starting from Lys558 (PDGFRβ, GenBank Accession No. M21616) in stead of HGFR in the above method. EGFR was purchased from Sigma (Production No. E-2645).

2. Expression and Purification of Receptor Tyrosine Kinases

To the suspension of Sf9 cells ($3 \times 10^8$ cells) in SF-900 II medium (purchased from Invitrogen) containing 2% FBS was added a solution of HGFR transfected baculovirus above (4 ml), followed by a shaking culture at 27° C. for 48 hrs. The cells infected with the HGFR transfected baculovirus were centrifuged at 1,000 rpm, 4° C. for 5 min to remove the supernatant. The precipitated infected cells were suspended in 80 ml of ice-cold PBS, and centrifuged at 1,000 rpm, 4° C. for 5 min to remove the supernatant. The precipitated infected cells were suspended in 40 ml of ice-cold Lysis Buffer (50 mM Tris-HCl (pH 8.5), 5 mM 2-mercaptoethanol, 100 mM KCl, 1 mM PMSF and 1% (v/v) NP-40). The suspension was centrifuged at 12,000 rpm, 4° C. for 30 min to provide a supernatant.

The supernatant was loaded onto an Ni-NTA agarose column (3 ml, purchased from Qiagen) equilibrated with 30 ml of Buffer A (20 mM Tris-HCl (pH 8.5), 5 mM 2-mercaptoethanol, 500 mM KCl, 20 mM imidazole and 10% (v/v) glycerol). The column was washed with 30 ml of Buffer A, 6 ml of Buffer B (20 mM Tris-HCl (pH 8.5), 5 mM 2-mercaptoethanol, 1 M KCl, and 10% (v/v) glycerol) and 6 ml of Buffer A in this order. Then, the column was eluted with 6 ml of Buffer C (20 mM Tris-HCl (pH 8.5), 5 mM 2-mercaptoethanol, 100 mM KCl, 100 mM imidazole, and 10% (v/v) glycerol) to provide a fraction. The fraction was entrapped in a dialysis membrane (purchased from Spectrum Laboratories), dialyzed at 4° C. overnight with 1 L of dialysis buffer (20 mM Tris-HCl (pH 7.5), 10% (v/v) glycerol, 1 mM dithiothreitol, 0.1 mM Na$_3$VO$_4$ and 0.1 mM EGTA), and stored at −80° C. until used. An aliquot of the dialyzed fraction was subjected to SDS electrophoresis, and then a recombinant protein (His6-HGFR, the HGFR cytoplasmic domain fused with six histidine at the N terminus) detected at a molecular weight of about 60 kDa when stained with Coomassie Brilliant Blue, was determined with regard to protein content using BSA (purchased from Sigma) as a standard. The VEGFR2 cytoplasmic domain, the FGFR1 cytoplasmic domain, and the PDGFRβ cytoplasmic domain were fused with six histidine at the N terminus by the similar method to produce respective recombinant proteins (His6-VEGFR2, His6-FGFR1, and His6-PDGFRβ).

3. Assay for the Inhibitory Activity Against HGFR Tyrosine Kinase Activity

To each well of a 96-well round plate (purchased from NUNC. Production No. 163320) were added 10 µl of a solution for kinase reaction (200 mM Hepes (pH 7.4), 80 mM $MgCl_2$, 16 mM $MnCl_2$ and 2 mM $Na_3VO_4$), 250 ng of biotinylated poly(Glu4: Tyr1) (biotin-poly(GT), purchased from Japan Schering) (6 µl, 15-fold diluted with distilled water), 30 ng of His6-HGFR (10 µl, 60-fold diluted with 0.4% BSA) and a test substance dissolved in dimethyl sulfoxide (4 µl, 100-fold diluted with 0.1% BSA) to mess up to 30 µl. To the well was added 10 µl of 4 µM ATP (purchased from Sigma) diluted with distilled water to incubate at 30° C. for 10 min, followed by adding 10 µl of 500 mM EDTA (pH 8.0) (purchased from Wako Pure Chemicals) to provide a kinase reaction solution.

The tyrosine-phosphorylated biotin-poly(GT) was detected using the Homogenous Time-Resolved Fluorescence (HTRF) method (Analytical Biochemistry, 269, 94-104, 1999). That is, to each well of a 96-well half-area black plate (purchased from COSTAR, Production No. 3694) were added 20 µl of the above kinase reaction solution and 30 µl of a dilution solution (50 mM Hepes (pH 7.4), 20 mM $MgCl_2$, 4 mM $MnCl_2$, 0.5 mM $Na_3VO_4$, 0.1% BSA and 100 mM EDTA). To the well was added 7.5 ng of an europium cryptate-labelled anti-phosphotyrosine antibody (Eu(K)—PY20, purchased from Japan Schering) (25 µl, 250-fold diluted with 20 mM Hepes (pH 7.0), 0.5 M KF and 0.1% BSA) and 250 ng of XL665-labelled streptavidin (XL665-SA, purchased from Japan Schering) (25 µl, 62.5-fold diluted with 20 mM Hepes (pH 7.0), 0.5 M KF and 0.1% BSA), and using a discovery HTRF microplate analyzer (Packard), the well was instantly irradiated at an excitation wavelength of 337 nm to determine fluorescence intensities at 665 nm and 620 nm. The tyrosine phosphorylation rate of a biotin-poly (GT) was calculated using a delta F % value described in the text of a HTRF standard experiment method by Japan Schering. While defining the delta F % value of a well added with His6-HGFR and no test substance as 100% and the delta F % value of a well added with no His6-HGFR and no test substance as 0%, ratio (%) of the delta F % value of each well added with the test substance was calculated. The ratio (%) was used to calculate the concentration ($IC_{50}$) of the test substance necessary to inhibit HGFR kinase activity by 50%.

$IC_{50}$ of the compound 1 was 0.053 µM and $IC_{50}$ of the compound 2 was 0.004 µM.

4. Assay for the Inhibitory Activity Against Receptor Tyrosine Kinase Activities Other than HGFR The inhibitory activity against tyrosine kinase activities of VEGFR2, FGFR1, and EGFR were determined by the similar manner as in the assay for the inhibitory activity against HGFR tyrosine kinase activity described above, using 15 ng of His6-VEGFR2, 15 ng of His6-FGFR1 or 23 ng of EGFR, respectively instead of HGFR.

The inhibitory activity against PDGFRβ tyrosine kinase activity was evaluated by obtaining a kinase reaction solution by the above method using 50 ng of His6-PDGFRβ, followed by detecting the tyrosine phosphorylated biotin-poly(GT) by a method described below.

To each well of a 96-well streptavidin-coated plate (purchased from PIERCE, Production No. 15129) were added 34 µl of the kinase reaction solution and 16 µl of a dilution solution, followed by incubation at room temperature for 30 min. Then, the well was washed three times with 150 µl of a washing solution (20 mM Tris-HCl (pH 7.6), 137 mM NaCl, 0.05% Tween-20 and 0.1% BSA), and to the well was added 701 of anti-phosphotyrosine (PY20)-HRP conjugate (purchased from Transduction Laboratories, Production No. P-11625) (2,000-fold diluted with 20 mM Tris-HCl (pH 7.6), 137 mM NaCl, 0.05% Tween-20 and 1% BSA), followed by incubation at room temperature for 1 hr. Then, each well was washed three times with 150 µl of the washing solution, and supplied with 100 µl of TMB Membrane Peroxidase Substrate (purchased from Funakoshi, Production No. 50-5077-03). After incubating the same at room temperature for 10 min, 100 µl of 1 M phosphoric acid was added to each well, and using a Plate Reader MTP-500 (Corona Electric), the absorbance of the well was instantly determined at 450 nm. While defining the absorbance of a well supplied with His6-PDGFRβ and no test substance as 100% and the absorbance of a well supplied with no His6-PDGFRβ and no test substance as 0%, the absorbance ratio (%) of each well supplied with the test substance was calculated. The absorbance ratio (%) was used to calculate the concentration ($IC_{50}$) of the test substance necessary to inhibit PDGFRβ kinase activity by 50%.

Pharmacological Test Example 2:Inhibitory Activity Against the Proliferation of Human Gastric Cancer Cells (MKN-45)

Human gastric cancer cells (MKN-45) were suspended in a 1% FBS-containing RPMI1640 medium (purchased from Sigma). The cell suspension ($1\times10^4$ cells/ml) was added in a 96-well plate for cell culture (purchased from NUNC, Production No. 167008) at 0.1 ml/well, and then cultured in a 5% $CO_2$ incubator (37° C.) overnight. After the culture, each well was supplied with 0.1 ml of a test substance diluted with a 1% FBS-containing RPMI1640 medium, followed by culturing in a 5% $CO_2$ incubator (37° C.) for 3 days. After the culture, each well was supplied with 10 µl of Cell Counting Kit-8 (purchased from DOJINDO, Production No. 343-07623), followed by incubation in a 5% $CO_2$ incubator (37° C.) for about 1.5 hrs. After the incubation, using the Plate Reader MTP-500 (Corona Electric), the absorbance of each well was determined at a measurement wavelength of 450 nm and a reference wavelength of 660 nm. The ratio (%) of absorbance of each well supplied with a test substance to absorbance of the well supplied with no test substance was calculated, and the ratio was used to calculate the concentration ($IC_{50}$) of the test substance necessary to inhibit the cell proliferation by 50%.

$IC_{50}$ of the compound 1 was 0.017 µM and $IC_{50}$ of compound 2 was 0.005 µM.

Pharmacological Test Example 3:Inhibitory Activity Against the HGFR Autophosphorylation Using ELISA 1. Preparation of Cell Extract Human gastric cancer cells (MKN-45) were suspended in a 1% FBS-containing RPMI1640 medium (purchased from Sigma). The cell suspension ($1\times10^5$ cells/ml) was put in a 96-well plate for cell culture (purchased from NUNC, Production No. 167008) at 0.1 ml/well, and then cultured in a 5% $CO_2$ incubator (37° C.) overnight. After the culture, from each well was removed the supernatant solution, followed by adding 0.05 ml of a 1% FBS-containing RPMI1640 medium. Then, the well was supplied with 0.05 ml of the test substance dissolved in dimethyl sulfoxide (diluted with a 1% FBS-containing RPMI1640 medium), followed by culturing in a 5% $CO_2$ incubator (37° C.) for 1 hr. From each well was removed the supernatant, and each well was washed with 150 µl of PBS, followed by adding 100 µl of a lysis buffer (50 mM Hepes (pH 7.4), 150 mM NaCl, 10% (v/v) glycerol, 1% Triton X-100, 1.5 mM $MgCl_2$, 1 mM EDTA (pH 8.0), 100 mM NaF, 1 mM PMSF, 10 µg/ml Aprotinin, 50 µg/ml Leupeptin, 1 µg/ml Pepstatin A and 1 mM $Na_3VO_4$). The plate was shaken at 4° C. for 1 hr to prepare the cell extract.

2. Preparation of an Anti-Phosphotyrosine Antibody-Immobilized Plate

To a 96-well plate for ELISA (purchased from COSTAR, Production No. 3369) was added 50 µl of 60 mM bicarbonate buffer (pH 9.6) containing 50 µg/ml of an anti-phosphotyrosine antibody (PY20, purchased from Transduction Laboratory, Production No. P-11120). The plate was incubated at 4° C. overnight.

3. Assay for Inhibitory Activity Against HGFR Autophosphorylation

Each well of the plate prepared in 2. was washed three times with 200 µl of PBS, and supplied with 150 µl of 3% BSA/PBS, followed by incubating at room temperature for 2 hrs. Each well was washed three times with 200 µl of PBS, and supplied with 50 µl of the above cell extract, followed by incubating at 4° C. overnight. After the incubation, each well was washed three times with 250 µl of a washing solution (0.1% BSA, 20 mM Tris-HCl (pH 7.6), 137 mM NaCl, and 0.05% Tween-20), and supplied with 70 µl of anti-HGFR antibody (h-Met(C-12), purchased from Santa Cruz, Production No. sc-10) 2,000-fold diluted with a reaction solution (1% BSA, 20 mM Tris-HCl (pH 7.6), 137 mM NaCl and 0.05% Tween-20), followed by incubating at room temperature for 1 hr. The well was washed three times with 250 µl of the washing solution, and supplied with 70 µl of peroxidase-labelled anti-rabbit IgG antibody (purchased from Cell Signaling, Production No. 7074) 2,000-fold diluted with the reaction solution, followed by incubating at room temperature for 1 hr. Each well was washed three times with 250 µl of the washing solution, and supplied with 70 µl of TMB Membrane Peroxidase Substrate (purchased from Funakoshi, Production No. 50-5077-03), followed by incubating at room temperature for 10 min. Each well was supplied with 70 µl of 1 M phosphoric acid, and using the Plate Reader MTP-500 (Corona Electric), the absorbance of the well was instantly determined at a measurement wavelength of 450 nm. While defining the absorbance of a well supplied with the cell extract having no test substance as 100% HGFR autophosphorylation activity, and the absorbance, of a well supplied with 50 µl of the lysis buffer as 0% HGFR autophosphorylation activity, the HGFR autophosphorylation activity (%) was calculated for each well. The concentration of the test substance was changed by several levels to calculate. HGFR autophosphorylation activities (%) in respective cases, and to calculate the concentration ($IC_{50}$) of the test substance necessary to inhibit HGFR autophosphorylation activity by 50%.

$IC_{50}$ of the compound 1 was 0.016 µM and $IC_{50}$ of the compound 2 was 0.0084 µM.

Production Example 1 for Pharmaceutical Composition: Film Coated Tablets (10 mg)

(1) 92.6 g of crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide (2R,3R)-tartrate, 2070.4 g of D-mannitol (Mannit Towa, trade name of Towa-Kasei Co., Ltd.) and 250.0 g of low-substituted hydroxypropylcellulose (L-HPC, trade name of Nippon Soda Co., Ltd.) were placed and mixed in a high-speed fluidizing mixer (Kawata Mfg. Co., Ltd.). A solution obtained by dissolving 50.0 g of hydroxypropylcellulose (HPC-SL, trade name of Shin-Etsu Chemical Co., Ltd.) in 325.0 g of absolute ethanol was then added thereto to give wet pellets.

(2) The obtained pellets were dried at 60° C. and a pulverizing granulator (Dalton Co., Ltd.) was used for size adjustment to give granules.

(3) To the obtained granules was added 37.0 g of magnesium stearate (Taihei Chemical Industrial Co., Ltd.), and a mixer was used for mixing to give a lubricious mixture.

(4) The obtained lubricious mixture was tableted using a tableting machine (Hata Iron Works Co., Ltd.) to produce tablets (uncoated tablets).

(5) The obtained uncoated tablets were coated with a solution containing 8.0% (w/w) of Opadry mixture (92.6 g, containing hydroxypropylcellulose 2910, macrogol 8000, titanium oxide, talc and red iron oxide) using a tablet coating machine (product of Powrex Corp.) to produce 10 mg coated tablets (total weight: 2592.6 g).

INDUSTRIAL APPLICABILITY

The salts of phenoxypyridine derivatives and their crystals according to the invention have excellent physical properties and are useful as antitumor agents, angiogenesis inhibitors and inhibitors for metastasis for various types of tumors including a pancreatic cancer, a gastric cancer, a colorectal cancer, a breast cancer, a prostate cancer, a lung cancer, a kidney cancer, a brain tumor, an ovarian cancer and an esophageal cancer.

What is claimed is:

1. An acid addition salt of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, wherein the acid is selected from the group consisting of hydrochloric acid, hydrobromic acid, sulfuric acid, fumaric acid, succinic acid, malic acid, and maleic acid.

2. Crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide malate.

3. Crystals according to claim 2, which have diffraction peaks at diffraction angles (2θ±0.2°) of 17.7°, 19.0° and 23.5° in an X-ray powder diffraction.

4. An acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, wherein the acid is selected from the group consisting of hydrochloric acid, hydrobromic acid, sulfuric acid, methanesulfonic acid, ethanesulfonic acid, benzenesulfonic acid and 4-methylbenzenesulfonic acid.

5. Crystals of an acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, wherein the acid is selected from the group consisting of hydrochloric acid, hydrobromic acid, sulfuric acid, ethanesulfonic acid and benzenesulfonic acid.

6. Crystals of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide methanesulfonate.

7. Crystals according to claim 6, which have diffraction peaks at diffraction angles (2θ±0.2°) of 17.7°, 20.4° and 21.7° in an X-ray powder diffraction.

8. Crystals of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide4-methylbenzenesulfonate.

9. Crystals according to claim 8, which have diffraction peaks at diffraction angles (2θ±0.2°) of 7.2°, 17.3° and 23.6° in an X-ray powder diffraction.

10. A process for preparing crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenypcyclopropane-1,1-dicarboxyamide malate, characterized by mixing N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, a solvent selected from the group consisting of acetone, ethanol, 1-propanol, and 2-propanol, and malic acid to form a solution, and then depositing crystals.

11. A process for preparing crystals of N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide tartrate, characterized by mixing N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxyamide, water and tartaric acid to form a solution, and then adding a solvent selected from the group consisting of acetone, ethanol, 1-propanol, and 2-propanol and depositing crystals.

12. A process for preparing crystals of an acid addition salt of N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, characterized by mixing N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxyamide, a solvent selected from the group consisting of acetone, ethanol, 1-propanol, and 2-propanol and an acid selected from the group consisting of hydrochloric acid, hydrobromic acid, sulfuric acid, methanesulfonic acid, ethanesulfonic acid, benzenesulfonic acid and 4-methylbenzenesulfonic acid to form a solution, and then depositing crystals.

13. A pharmaceutical composition comprising crystals according to claim 2 and one or more pharmaceutically acceptable carriers.

14. A method for treating cancer in which HGFR is overexpressed comprising administering to a patient, a pharmacologically effective dose of crystals according to claim 2, wherein the cancer is gastric cancer or lung cancer.

15. A method for inhibiting cancer metastasis in which HGFR is overexpressed comprising administering to a patient, a pharmacologically effective dose of crystals according to claim 2, wherein the cancer is gastric cancer or lung cancer.

16. A pharmaceutical composition comprising crystals according to claim 6 and one or more pharmaceutically acceptable carriers.

17. A pharmaceutical composition comprising crystals according to claim 8 and one or more pharmaceutically acceptable carriers.

18. A method for treating cancer in which HGFR is overexpressed comprising administering to a patient, a pharmacologically effective dose of crystals according to claim 6, wherein the cancer is gastric cancer or lung cancer.

19. A method for treating cancer in which HGFR is overexpressed comprising administering to a patient, a pharmacologically effective dose of crystals according to claim 8, wherein the cancer is gastric cancer or lung cancer.

20. A method for inhibiting cancer metastasis in which HGFR is overexpressed comprising administering to a patient, a pharmacologically effective dose of crystals according to claim 6, wherein the cancer is gastric cancer or lung cancer.

21. A method for inhibiting cancer metastasis in which HGFR is overexpressed comprising administering to a patient, a pharmacologically effective dose of crystals according to claim 8, wherein the cancer is gastric cancer or lung cancer.

\* \* \* \* \*

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 1
ccggccggat ccaaaaagag aaagcaaatt aaa        33

```
<210> SEQ ID NO 2
<211> LENGTH: 33
<212> TYPE: DNA
<213> ORGANISM: Artificial Sequence
<220> FEATURE:
<223> OTHER INFORMATION: an artificially synthesized primer sequence

<400> SEQUENCE: 2
ttaattctgc agctatgatg tctcccagaa gga                              33
```